US009833420B2

(12) United States Patent
McLaurin

(10) Patent No.: US 9,833,420 B2
(45) Date of Patent: *Dec. 5, 2017

(54) METHODS OF PREVENTING, TREATING, AND DIAGNOSING DISORDERS OF PROTEIN AGGREGATION

(71) Applicant: JoAnne McLaurin, East York (CA)

(72) Inventor: JoAnne McLaurin, East York (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/608,617

(22) Filed: Jan. 29, 2015

(65) Prior Publication Data

US 2015/0164821 A1    Jun. 18, 2015

Related U.S. Application Data

(63) Continuation of application No. 14/016,733, filed on Sep. 3, 2013, now abandoned, which is a continuation of application No. 13/408,337, filed on Feb. 29, 2012, now abandoned, which is a continuation of application No. 12/396,515, filed on Mar. 3, 2009, now abandoned, which is a continuation of application No. 10/787,621, filed on Feb. 26, 2004, now Pat. No. 7,521,481.

(60) Provisional application No. 60/451,363, filed on Feb. 27, 2003, provisional application No. 60/520,958, filed on Nov. 17, 2003, provisional application No. 60/523,534, filed on Nov. 19, 2003.

(51) Int. Cl.
| | |
|---|---|
| *A61K 31/047* | (2006.01) |
| *A61K 45/06* | (2006.01) |
| *A61K 31/70* | (2006.01) |
| *A61K 51/04* | (2006.01) |
| *G01N 33/60* | (2006.01) |
| *G01N 33/68* | (2006.01) |

(52) U.S. Cl.
CPC ............ *A61K 31/047* (2013.01); *A61K 31/70* (2013.01); *A61K 45/06* (2013.01); *A61K 51/04* (2013.01); *A61K 51/0491* (2013.01); *G01N 33/60* (2013.01); *G01N 33/6896* (2013.01)

(58) Field of Classification Search
CPC ...... A61K 31/047; A61K 31/70; A61K 45/06; A61K 51/04; A61K 51/0491; G01N 33/60; G01N 33/6896
USPC ......................................................... 514/729
See application file for complete search history.

(56) References Cited

U.S. PATENT DOCUMENTS

| | | | |
|---|---|---|---|
| 4,201,706 A | 5/1980 | Green et al. | |
| 4,454,151 A | 6/1984 | Waterbury | |
| 4,474,806 A | 10/1984 | Beattie | |
| 4,515,722 A | 5/1985 | Yang et al. | |
| 4,522,752 A | 6/1985 | Sisto et al. | |
| 4,734,283 A | 3/1988 | Siren | |
| 4,735,902 A | 4/1988 | Siren | |
| 4,735,936 A | 4/1988 | Siren | |
| 4,758,420 A | 7/1988 | Knowles et al. | |
| 4,758,430 A | 7/1988 | Sabin | |
| 4,777,134 A | 10/1988 | Siren | |
| 4,793,945 A | 12/1988 | Siren | |
| 4,794,014 A | 12/1988 | Siren | |
| 4,797,390 A | 1/1989 | Siren | |
| 4,847,082 A | 7/1989 | Sabin | |
| 4,851,560 A | 7/1989 | Siren | |
| 4,895,841 A | 1/1990 | Sugimoto et al. | |
| 4,948,807 A | 8/1990 | Rosin et al. | |
| 4,952,396 A | 8/1990 | Sabin et al. | |
| 5,003,098 A | 3/1991 | Siren | |
| 5,019,566 A | 5/1991 | Siren | |
| 5,023,248 A | 6/1991 | Siren | |
| 5,057,507 A | 10/1991 | Siren | |
| 5,112,814 A | 5/1992 | Sabin | |
| 5,128,332 A | 7/1992 | Siren | |
| 5,135,923 A | 8/1992 | Siren | |
| 5,217,959 A | 6/1993 | Sabin | |
| 5,306,841 A | 4/1994 | Bundgaard et al. | |
| 5,330,979 A | 7/1994 | Siren | |
| 5,342,832 A | 8/1994 | Siren | |
| 5,407,924 A | 4/1995 | Siren | |
| 5,412,080 A | 5/1995 | Kishi et al. | |
| 5,545,632 A | 8/1996 | Siren | |
| 5,554,399 A | 9/1996 | Vanderbeke | |
| 5,602,176 A | 2/1997 | Enz | |
| 5,614,510 A | 3/1997 | Persson | |
| 5,633,412 A | 5/1997 | Hudlicky et al. | |
| 5,643,562 A | 7/1997 | Kisilevsky et al. | |
| 5,714,643 A | 2/1998 | Sato | |

(Continued)

FOREIGN PATENT DOCUMENTS

| | | |
|---|---|---|
| CA | 2 105 530 | 3/1994 |
| CA | 2214635 | 9/1996 |

(Continued)

OTHER PUBLICATIONS

McGuire et al. (A bimonthly Mental Health/Mental Retardation Publication, Jan./Feb. 1996, vol. 15, No. 1).*
Abulkalam, M.,"Inositol phosphates have novel anticancer function." Journal of Nutrition 125 725S-732S 1995.
Agam, R.,et al. "High-dose peripheral inositol raises brain inositol levels and reverses behavioural effects of inositol depletion by lithium," Pharmaol. Biochem. Behay. 49, 341-343, 1994.
Alexakis, A., et al., "A practical, solvent free, one-pot synthesis of C2-symmetrical secondary amines," Tet. Letters, 2004, vol. 45, pp. 1449-1451.
Allan, SJR, et al., "The effect of inositol supplements on the psoriasis of patients taking lithium: a randomized, placebo-controlled trial," British Journal of Dermatology 150(5): 966-969 (2004).

(Continued)

*Primary Examiner* — Uma Ramachandran
(74) *Attorney, Agent, or Firm* — Millen, White, Zelano, Branigan, P.C.

(57) ABSTRACT

Disclosed are methods of preventing, treating, or diagnosing in a subject a disorder in protein folding or aggregation, or amyloid formation, deposition, accumulation, or persistence consisting of administering to said subject a pharmaceutically effective amount of inositol stereoisomers, enantiomers or derivatives thereof.

7 Claims, 17 Drawing Sheets

(56) References Cited

U.S. PATENT DOCUMENTS

| | | |
|---|---|---|
| 5,728,375 A | 3/1998 | Kisilevsky et al. |
| 5,760,022 A | 6/1998 | Persson et al. |
| 5,840,294 A | 11/1998 | Kisilevsky et al. |
| 5,858,326 A | 1/1999 | Kisilevsky et al. |
| 5,880,099 A | 3/1999 | Traynor-Kaplan et al. |
| 5,972,328 A | 10/1999 | Kisilevsky et al. |
| 5,977,078 A | 11/1999 | Traynor-Kaplan et al. |
| 5,981,168 A | 11/1999 | Reiner et al. |
| 5,985,864 A | 11/1999 | Imai et al. |
| 5,998,485 A | 12/1999 | Tyan et al. |
| 6,099,863 A | 8/2000 | Gilis et al. |
| 6,140,321 A | 10/2000 | Imai et al. |
| 6,153,603 A | 11/2000 | Siren |
| 6,218,506 B1 | 4/2001 | Krafft et al. |
| 6,232,486 B1 | 5/2001 | Aneja |
| 6,310,073 B1 | 10/2001 | Kisilevsky et al. |
| 6,329,256 B1 | 12/2001 | Ibok |
| 6,358,527 B1 | 3/2002 | Gillis et al. |
| 6,384,260 B1 | 5/2002 | Aneja |
| 6,448,229 B2 | 9/2002 | Teall |
| 6,599,891 B2 | 7/2003 | North et al. |
| 6,627,739 B1 | 9/2003 | Anderson et al. |
| 6,683,091 B2 | 1/2004 | Asberom et al. |
| 6,720,190 B1 | 4/2004 | Hindsgaul et al. |
| 6,737,420 B2 | 5/2004 | Hom et al. |
| 6,756,511 B2 | 6/2004 | Castro Pineiro et al. |
| 6,852,482 B1 | 2/2005 | Chrysler et al. |
| 6,890,956 B2 | 5/2005 | Churcher et al. |
| 6,906,104 B2 | 6/2005 | Schostarez et al. |
| 6,960,664 B2 | 11/2005 | Schostarez et al. |
| 6,962,934 B2 | 11/2005 | Warpehoski et al. |
| 7,015,240 B2 | 3/2006 | North et al. |
| 7,157,268 B2 | 1/2007 | Takahashi |
| 7,282,513 B2 | 10/2007 | Collins et al. |
| 7,521,481 B2 | 4/2009 | McLaurin |
| 2001/0041677 A1 | 11/2001 | Martin-Lomas et al. |
| 2001/0048941 A1 | 12/2001 | Kisilevsky et al. |
| 2001/0053767 A1 | 12/2001 | Martin-Lomas et al. |
| 2002/0013315 A1 | 1/2002 | Teall et al. |
| 2002/0019403 A1 | 2/2002 | Hom et al. |
| 2002/0052311 A1 | 5/2002 | Solomon et al. |
| 2002/0115616 A1 | 8/2002 | Boyd et al. |
| 2002/0128255 A1 | 9/2002 | Beck et al. |
| 2002/0143177 A1 | 10/2002 | Beck et al. |
| 2002/0193395 A1 | 12/2002 | Kisilevsky et al. |
| 2003/0055005 A1 | 3/2003 | Pineiro et al. |
| 2003/0068316 A1 | 4/2003 | Klein et al. |
| 2003/0087889 A1 | 5/2003 | Strong et al. |
| 2003/0100512 A1 | 5/2003 | Nadin et al. |
| 2003/0108595 A1 | 6/2003 | Kisilevsky et al. |
| 2003/0114387 A1 | 6/2003 | Pineiro et al. |
| 2003/0153512 A1 | 8/2003 | Hergenhahn et al. |
| 2003/0181531 A1 | 9/2003 | Sherris et al. |
| 2003/0216380 A1 | 11/2003 | Josien et al. |
| 2004/0019032 A1 | 1/2004 | North et al. |
| 2004/0028673 A1 | 2/2004 | Netzer |
| 2004/0048848 A1 | 3/2004 | Pissarnitski et al. |
| 2004/0058313 A1 | 3/2004 | Abreu |
| 2004/0171614 A1 | 9/2004 | Pissarnitski et al. |
| 2004/0204387 A1 | 10/2004 | McLaurin |
| 2004/0214307 A1 | 10/2004 | Takahasi et al. |
| 2004/0229902 A1 | 11/2004 | Josien |
| 2004/0234626 A1 | 11/2004 | Gardiner et al. |
| 2005/0075320 A1 | 4/2005 | Nadin et al. |
| 2005/0085506 A1 | 4/2005 | Pissarnitski et al. |
| 2005/0119227 A1 | 6/2005 | Cumming et al. |
| 2005/0143369 A1 | 6/2005 | Pineiro et al. |
| 2005/0171112 A1 | 8/2005 | Schulz et al. |
| 2005/0182138 A1 | 8/2005 | John et al. |
| 2006/0004096 A1 | 1/2006 | Larner |
| 2006/0135624 A1 | 6/2006 | Liang et al. |
| 2006/0148905 A1 | 7/2006 | Kim et al. |
| 2006/0189582 A1 | 8/2006 | McLaurin |
| 2006/0240534 A1 | 10/2006 | Yamaguchi et al. |
| 2007/0078099 A1 | 4/2007 | McLaurin |
| 2007/0111970 A1 | 5/2007 | Cruz et al. |
| 2007/0197452 A1 | 8/2007 | McLaurin |
| 2007/0197453 A1 | 8/2007 | McLaurin |
| 2007/0254958 A1 | 11/2007 | Coburn et al. |
| 2007/0259898 A1 | 11/2007 | Baxter et al. |
| 2007/0265331 A1 | 11/2007 | Dicecco et al. |
| 2008/0200437 A1 | 8/2008 | Lehn et al. |
| 2008/0306166 A1 | 12/2008 | McLaurin |
| 2009/0062403 A1 | 3/2009 | McLaurin |
| 2009/0170957 A1 | 7/2009 | Cruz et al. |
| 2009/0227686 A1 | 9/2009 | McLaurin |
| 2010/0093648 A1 | 4/2010 | Cruz |
| 2010/0105631 A1 | 4/2010 | Cruz |
| 2010/0113613 A1 | 5/2010 | Cruz et al. |
| 2010/0144891 A1 | 6/2010 | McLaurin |
| 2010/0152305 A1 | 6/2010 | Cedarbaum |
| 2010/0168250 A1 | 7/2010 | Cruz |
| 2010/0173960 A1 | 7/2010 | Cruz et al. |
| 2010/0292157 A1 | 11/2010 | Cruz et al. |
| 2010/0331267 A1 | 12/2010 | McLaurin |
| 2011/0028719 A1 | 2/2011 | Slon-Usakiewicz |
| 2011/0105626 A1 | 5/2011 | McLaurin |
| 2011/0201694 A1 | 8/2011 | McLaurin |
| 2012/0157549 A1 | 6/2012 | McLaurin |

FOREIGN PATENT DOCUMENTS

| | | |
|---|---|---|
| CA | 2283255 | 9/1998 |
| CA | 2406383 | 10/2001 |
| CA | 2 427 742 | 1/2002 |
| CA | 2486663 | 12/2003 |
| CA | 2 516 563 | 9/2004 |
| CA | 2 588 423 | 5/2006 |
| CA | 2 579 188 | 8/2007 |
| DE | 3 405 663 | 8/1985 |
| EP | 1608350 | 9/2004 |
| EP | 1824496 | 5/2006 |
| EP | 1 674 578 | 6/2006 |
| EP | 1996175 | 9/2007 |
| EP | 1940373 | 10/2007 |
| EP | 1993523 | 11/2007 |
| EP | 1865056 | 12/2007 |
| EP | 2091566 | 5/2008 |
| EP | 2148667 | 10/2008 |
| EP | 2153829 | 2/2010 |
| EP | 2349280 | 3/2010 |
| EP | 2349233 | 4/2010 |
| EP | 2186518 | 5/2010 |
| EP | 2311445 | 4/2011 |
| EP | 0792556.4 | 8/2011 |
| GB | 2385124 | 8/2003 |
| GB | 2389113 | 4/2004 |
| JP | 04 126075 | 4/1992 |
| JP | 05 192163 | 8/1993 |
| JP | 2009-140388 | 3/1997 |
| JP | 2003 102492 | 4/2003 |
| JP | 2003-102492 | 8/2003 |
| JP | 06 007158 | 1/2004 |
| JP | 2006-007158 | 1/2004 |
| JP | 2006-501433 | 2/2004 |
| JP | 2007-541601 | 11/2005 |
| JP | 2008-535136 | 10/2006 |
| JP | 2008-554886 | 2/2007 |
| JP | 2008-557568 | 3/2007 |
| JP | 2009-537460 | 11/2007 |
| JP | 2010-502395 | 11/2008 |
| JP | 2011-530339 | 9/2009 |
| JP | 2010-294145 | 12/2010 |
| WO | WO-91 09601 | 7/1991 |
| WO | WO-93 12093 | 6/1993 |
| WO | WO 94-05275 | 3/1994 |
| WO | WO-94 05275 | 3/1994 |
| WO | WO-98 57620 | 12/1998 |
| WO | WO-99 38516 | 8/1999 |
| WO | WO-00 15254 | 3/2000 |
| WO | WO 00-17369 | 3/2000 |
| WO | WO-00 24406 | 5/2000 |
| WO | WO-00 45634 | 8/2000 |
| WO | WO 00-50391 | 8/2000 |

(56) References Cited

FOREIGN PATENT DOCUMENTS

| | | |
|---|---|---|
| WO | WO-00 75355 | 12/2000 |
| WO | WO 00-77030 | 12/2000 |
| WO | WO-01 03680 | 1/2001 |
| WO | WO-01 23337 | 4/2001 |
| WO | WO-01 28356 | 4/2001 |
| WO | WO 01-34571 | 5/2001 |
| WO | WO 01-34639 | 5/2001 |
| WO | WO 01-53255 | 7/2001 |
| WO | WO-01 66096 | 9/2001 |
| WO | WO 01-66564 | 9/2001 |
| WO | WO 01-70672 | 9/2001 |
| WO | WO 01-70677 | 9/2001 |
| WO | WO 01-77144 | 10/2001 |
| WO | WO 01-87293 | 11/2001 |
| WO | WO 02-02505 | 1/2002 |
| WO | WO 02-02506 | 1/2002 |
| WO | WO 02-02512 | 1/2002 |
| WO | WO 02-02518 | 1/2002 |
| WO | WO 02-02520 | 1/2002 |
| WO | WO-02 02582 | 1/2002 |
| WO | WO 02-36555 | 5/2002 |
| WO | WO 02-48150 | 6/2002 |
| WO | WO-02 055715 | 7/2002 |
| WO | WO-02 076440 | 10/2002 |
| WO | WO 02-088101 | 11/2002 |
| WO | WO 02-094768 | 11/2002 |
| WO | WO 02-094985 | 11/2002 |
| WO | WO 02-098849 | 12/2002 |
| WO | WO 02-100399 | 12/2002 |
| WO | WO 02-100410 | 12/2002 |
| WO | WO 02-100818 | 12/2002 |
| WO | WO 02-100820 | 12/2002 |
| WO | WO 02-100856 | 12/2002 |
| WO | WO 03-000261 | 1/2003 |
| WO | WO 03-002122 | 1/2003 |
| WO | WO 03-006013 | 1/2003 |
| WO | WO 03-006021 | 1/2003 |
| WO | WO 03-006453 | 1/2003 |
| WO | WO 03-013527 | 1/2003 |
| WO | WO 03-014075 | 2/2003 |
| WO | WO 03-020370 | 3/2003 |
| WO | WO 03-027068 | 4/2003 |
| WO | WO 03-029169 | 4/2003 |
| WO | WO 03-030886 | 4/2003 |
| WO | WO 03-037325 | 5/2003 |
| WO | WO 03-039454 | 5/2003 |
| WO | WO 03-040096 | 5/2003 |
| WO | WO 03-043987 | 5/2003 |
| WO | WO 03-045378 | 6/2003 |
| WO | WO 03-047576 | 6/2003 |
| WO | WO 03-050073 | 6/2003 |
| WO | WO 03-057165 | 7/2003 |
| WO | WO 03-057721 | 7/2003 |
| WO | WO 03-059346 | 7/2003 |
| WO | WO 03-064396 | 8/2003 |
| WO | WO 03-066592 | 8/2003 |
| WO | WO 03-091278 | 11/2003 |
| WO | WO 03-094854 | 11/2003 |
| WO | WO 03-103652 | 12/2003 |
| WO | WO 03-103653 | 12/2003 |
| WO | WO 03-104437 | 12/2003 |
| WO | WO 2004-002478 | 1/2004 |
| WO | WO 2004-013090 | 2/2004 |
| WO | WO 2004-013098 | 2/2004 |
| WO | WO 2004-013400 | 2/2004 |
| WO | WO 2004-022523 | 3/2004 |
| WO | WO 2004-024081 | 3/2004 |
| WO | WO 2004-029019 | 4/2004 |
| WO | WO 2004-031137 | 4/2004 |
| WO | WO 2004-031139 | 4/2004 |
| WO | WO 2004-052348 | 6/2004 |
| WO | WO 2004-062652 | 7/2004 |
| WO | WO 2004-069826 | 8/2004 |
| WO | WO 2004-071431 | 8/2004 |
| WO | WO 2004-075882 | 10/2004 |
| WO | WO 2004-089911 | 10/2004 |
| WO | WO 2004-094384 | 11/2004 |
| WO | WO 2004-094413 | 11/2004 |
| WO | WO 2004-100958 | 11/2004 |
| WO | WO 2004-101538 | 11/2004 |
| WO | WO 2004-101562 | 11/2004 |
| WO | WO 2004-050609 | 12/2004 |
| WO | WO 2005-004802 | 1/2005 |
| WO | WO 2005-004803 | 1/2005 |
| WO | WO 2005-008250 | 1/2005 |
| WO | WO 2005-009344 | 2/2005 |
| WO | WO 2005-014553 | 2/2005 |
| WO | WO 2005-016876 | 2/2005 |
| WO | WO 2005-018545 | 3/2005 |
| WO | WO 2005-028440 | 3/2005 |
| WO | WO 2005-030709 | 4/2005 |
| WO | WO 2005-030731 | 4/2005 |
| WO | WO 2005-032471 | 4/2005 |
| WO | WO-2005 035774 | 4/2005 |
| WO | WO 2005-040126 | 5/2005 |
| WO | WO-2005 044278 | 5/2005 |
| WO | WO 2005-044830 | 5/2005 |
| WO | WO 2005-051914 | 6/2005 |
| WO | WO 2005-058857 | 6/2005 |
| WO | WO 2005-063796 | 7/2005 |
| WO | WO 2005-065195 | 7/2005 |
| WO | WO 2005-074971 | 8/2005 |
| WO | WO 2005-074980 | 8/2005 |
| WO | WO 2005-075632 | 8/2005 |
| WO | WO 2005-095326 | 10/2005 |
| WO | WO 2005-097767 | 10/2005 |
| WO | WO 2005-097768 | 10/2005 |
| WO | WO 2005-103020 | 11/2005 |
| WO | WO 2005-103043 | 11/2005 |
| WO | WO-2006 047544 | 5/2006 |
| WO | WO 2006-053428 | 5/2006 |
| WO | WO 2006-088705 | 8/2006 |
| WO | WO 2006-109479 | 10/2006 |
| WO | WO 2007-002220 | 1/2007 |
| WO | WO 2007-011833 | 1/2007 |
| WO | WO 2007-019080 | 2/2007 |
| WO | WO 2007-021793 | 2/2007 |
| WO | WO 2007-041855 | 4/2007 |
| WO | WO 2007-101353 | 9/2007 |
| WO | WO 2007-119108 | 10/2007 |
| WO | WO 2007-129221 | 11/2007 |
| WO | WO 2007-134449 | 11/2007 |
| WO | WO 2008-034244 | 3/2008 |
| WO | WO-2008 061373 | 5/2008 |
| WO | WO-2008 098371 | 8/2008 |
| WO | WO-2008 1 24930 | 10/2008 |
| WO | WO-2008 014931 | 10/2008 |
| WO | WO-2008 024930 | 10/2008 |
| WO | WO-2008 124929 | 10/2008 |
| WO | WO-2008 124931 | 10/2008 |
| WO | WO-2008 124940 | 10/2008 |
| WO | WO 2010-031051 | 3/2010 |
| WO | WO 2010-031061 | 3/2010 |
| WO | WO 2010-040232 | 4/2010 |
| WO | WO 2012-173808 | 6/2012 |

OTHER PUBLICATIONS

Alzheimer Society of Canada, Research Program, Research Grants & Training Awards 2002, Alzheimer's disease: Inositol and Amyloid-β Interactions, May/Jun. 2002.

Anderson, R.C., "The Catalytic Hydrogenation of Polyhydric Phenols. I. The synthesis of meso-Inositol, Scyllitol and a New Isomeric Cyclitol.," Sep. 1948, pp. 2931-2935.

Antai-Otong, D., "Acetylcholinesterase Inhibitors in Dementia," Perspectives in Psychiatric Care, vol. 39, No. 2, Apr.-Jun. 2003, pp. 83-85.

Apostol, B. L. et al., "A cell-based assay for aggregation inhibitiors as theraopeutics of polyglutamine-repeat disease and validation in *Drosophila*," PNAS, 2003, vol. 100, pp. 5950-5955.

(56) References Cited

OTHER PUBLICATIONS

Asai, M. et al., "The novel Beta-secretase inhibitor KMI-429 reduces amyloid Beta peptide Production in amyloid precursor protein transgenic and wild-type mice," Journal of Neurochem., 2006, vol. 96, No. 2, pp. 533-540.
Asberom, T. et al., "Tetrahydroquinoline sulfonates as γ-secretase inhibitors," Bioorganic & Medicinal Chemistry Letters, 2007, vol. 17, No. 1, pp. 205-207.
Bakewell, S., "Phytic acid: A phytochemical with complementary and alternative benefits," Cancer Biol. Ther., 2006, vol. 5, No. 9, pp. 1134-1135.
Barak, Y., et al., "Effects of inositol on lithium-induced EEG abnormalities," Eur. N-Psypharmacol. 4(3): 419 (1994).
Barak, Y., et al., "Inositol treatment of Alzheimer's disease: A double-blind, cross-over placebo controlled trial," Prog. Neuro-Psychopharmacol. & Biol. Psychiatry. 20: 729-735 (1996).
Bard, F., et al., "Peripherally administered antibodies against amyloid β-peptide enter the central nervous system and reduce pathology in a mouse model of Alzheimer disease," Nature medicine 6(8): 916-919 (2000).
Barkai, IA., et al., "Reduced myo-inositol levels in cerebrospinal fluid from patients with affective disorder," Biol Psychiat 13: 65-72 (1978).
Beal, M.F., et al., "Experimental Therapeutics in Transgenic Mouse Models of Huntington's Disease," Nature Rev. Neuroscience, 2004, vol. 5, pp. 373-384.
Benjamin J, et al., "Double-blind, placebo-controlled, crossover trial of inositol treatment for panic disorder," Am J Psychiatry. 152: 1084-6 (1995).
Benjamin, J., et al., "Acute inositol does not attenuate m-CPP-induced anxiety, mydriasis and endocrine effects in panic disorder," J. Psychiatry. Res. 31(4): 489-495 (1997).
Benson, M.D., et al., "Serum amyloid a protein in amyloidosis, rheumatic, and neoplastic diseases," Arth. Rheum, 1979, vol. 22, pp. 36-43.
Berry, Gerard T. et al., "Loss of Murine Na+/myo-Inositol Cotransporter Leads to Brain myo-Inositol Depletion and Central Apnea," The Journal of Biological Chemistry. vol. 278, No. 20, Issue of May 16:18297-18302 (2003).
Bersudsky, Y., et al., "The effect of inositol on Li-induced polyuria polydipsia in rats and humans," Human Psychoparm. 7: 403-407 (1992).
Bersudsky, Y., et al., Epi-Inositol and Inositol Depletion: Two New Treatment Approaches to Affective Disorder. Current Psychiatry Reports 1999 I:141-147 (1999).
Best, J.D., et al., "Quantitive Measurement of Changes in Amyloid-beta(40) in the Rat Brain and Cerebrospinal Fluid Following Treatment with the beta-secretase inhibitors L Y-411575 [N2-[(2S)-2-(3,5-Diflurorphenyl)-2-hydroxyethanoyl]-N1-[(7S0-5-methyl-6-oxo-6,7-dihydro-5H-dibenzo[b,d]asepin-7-yl) L alaninamide]" J. Pharmacol Exp. Ther., 2005, vol. 313, No. 2, pp. 902-908.
Boncristiano, S., et al., "Cholinergic changes in the APP23 Transgenic Mouse Model of Cerebral Amyloidosis," The Journal of Neuroscience, 2002, vol. 22, pp. 3234-3243.
Bornemann, et al., "Transgenic mouse models of Alzheimer's disease," NY Acad. Sci. 908, Jun. 2000, pp. 260-266.
Braak, H., et al., "Frequency of stages of Alzheimer-related lesions in different age categories," Neurobiology of Aging 18: 351-357 (1997).
Brief Communication from European Patent Office for related EP 06 850 456 dated Aug. 5, 2009.
Campbell, W.W., et al., "Pinitol supplementation does not affect insulin-mediated glucose metabolism and muscle insulin receptor content and phosphorylation in older humans," J. Nutr. 134: 2998-3003 (2004).
Candy, D.J., "Occurrence and metamolism of scylloInositol in the Locust," *Biochem.J.* 1967, 103, pp. 666-671.
Cannon, M.J et al., "Kinetic Analysis of β-amyloid fibril elongation," Anal Biochem., 2004, 328(1):67-75.

Carey, P., et al., Single Photon Emission Computed Tomography (SPECT) in Obsessive-Complusive Disorder Before and After Treatment with Inositol. Metabolic Brain Disease vol. 19, Nos. 1/2, Jun. 2004 125-134 (2004).
Chalifour, R.J., et al., "Stereoselective Interactions of Peptide Inhibitors with the Beta Amyloid Peptide," J. Biol. Chem 2003 278(37) 34874-34881.
Chantal, Sophie, et al., "Correlation of Regional Proton Magnetic Resonance Spectroscopic Metabolic Changes With Cognitive Deficits in Mild Alzheimer Disease," Arch Neurol. 59: 955-962 (Jun. 2002).
Chartier-Harlin, M.C., et al., "Alpha-Synuclein locus duplication as a cause of familial Parkinson's Disease," Lancet, 2004, vol. 364, pp. 1167-1169.
Chen, X., et al., "The Human NACP/α-Synuclein Gene:Chromosome Assignment to 4q21.3-q22 and Taql RFLP Analysis", Genomics, 1995, vol. 26, No. 2, pp. 425-427.
Chen, Y.L., et al., "Thiazole-diamides as potent c-secretase inhibitors", Bioorganic & Medicinal Chemistry Letters, 2007, vol. 17, No. 20, pp. 5518-5522.
Chengappa. K.N., et al., "Inositol as an add-on treatment for bipolar depression," Bipolar Disorder 2(1): 47-55 (2000).
Chishti, M., et al., "Early-onset amyloid deposition and cognitive deficits in transgenic mice expressing a double mutant form of amyloid precursor protein 695," J. Biol Chem. 276: 21562-21570 (2001).
Choo-Smith, L.P., et al., "The interaction between Alzheimer amyloid beta(1-40) peptide and ganglioside GM1-containing membranes," *FEBS Lett* 402, 95-98 (1997).
Chopdar, A., et al "Age related macular degeneration", BMJ, 2003, vol. 326, pp. 485-488.
Chou. S., et al., "CGS21680 attenuates symptoms of Huntington's disease in a transgenic mouse model", J. Neurochem, 2002, vol. 93, No. 2, pp. 310-320.
Chung, S-K., "Synthesis of all possible regioisomers of scyllo-Inositol phosphate, " *Bioorganic & Medicinal Chemistry*, (1999) pp. 2577-2589.
Citron, M., "Strategies for disease modification in Alzheimer's disease," Nature Reviews 5: 677-685 (2004).
Cleary, J., et al., "Natural oligomers of the amyloid-β protein specifically disrupt cognitive function," Nat. Neurosci. 8: 79-84 (2005).
Clements, R.S., Jr., et al., "The metabolism of myo-inositol by the human kidney," J. Lab. Clin. Med. 93(2): 210-219 (1979).
Clements R.S., Jr., et al., Myoinositol metabolism in diabetes mellitus. Effects of insulin treatment. Diabetes 26: 215-221, Mar. 1997.
Coady MJ, Wallendorff B, Gagnon DG, Lapointe J-Y. (2002). Identification of a novel Na+/myo-inositol cotransporter. J. Biol. Chem. 277: 35219-35224 (1977).
Cogram, P., et al., "D-Chiro-inositol is more effective than myo-inositol in preventing folate-resistant mouse neural tube defects," Human Reproduction. 17: 2451-2458 (2002).
Cohen, H., et al., "Inositol has behavioural effects with adaptation after chronic administration," J Neural Transm. 104:299-305 (1997).
Cohen, H., et al., "Acute Inositol Induces Anxiety in Rats," Biol Psychiatry. 40:426-427 (1996).
Colodny, L., "Inositol-clinical applications for exogenous use," Altern. Med Rev. 3 (6): 432 447, 1998.
Communication from the Examining Division for related European Application No. 07710726 dated Aug. 3, 2009.
Communication from the Examination Division for related European Patent Application No. 04715226 dated Feb. 28, 2007.
Communication from the Examination Division for related European Patent Application No. 04715226 dated May 4, 2006.
Communication from the Examining Division for related European Application No. 05808109 dated Oct. 6, 2008.
Communication from the Examining Division for related European Application No. 07789484 dated Sep. 11, 2009.
Communication pursuant to Article 94(3) EPC for related EP 06 850 456 dated Jan. 31, 2012.

(56) References Cited

OTHER PUBLICATIONS

Communication pursuant to Article 94(3) EPC for related EP 06 850 456 dated Jul. 29, 2009.
Communication pursuant to Article 94(3) EPC for related EP 07 710 726 dated Aug. 22, 2011.
Communication pursuant to Article 94(3) EPC for related EP 09 005 295 dated Jan. 19, 2012.
Communication pursuant to Article 94(3) EPC for related EP 09 005 295 dated Sep. 1, 2010.
Communication pursuant to Article 94(3) EPC for related EP 10 010 477 dated Jan. 19, 2012.
Communication regarding the transmission of the European Search Report for related European Application No. 06850456 dated Jul. 28, 2009.
Communication regarding the transmission of the European Search Report for related European Application No. 05808109 dated Jun. 17, 2008.
Communication regarding the transmission of the European Search Report for related European Application No. 09005295 dated Jan. 14, 2010.
Communication regarding the transmission of the European Search Report for related European Applicatio No. 07789484 dated May 12, 2009.
Communication regarding the transmission of the European Search Report for related European Application No. 07710726 dated May 11, 2009.
Communication regarding the transmission of the European Search Report for related European Application No. 08733752 dated May 4, 2010.
Communication regarding the transmission of the European Search Report for related European Application No. 10000985 dated Mar. 16, 2010.
Consulatation by telephone with applicant/ representative for related European Patent Application No. 04715226 dated Sep. 2, 2008.
D'Alarcao Declaration of Nov. 28, 2007 from U.S. Appl. No. 10/787,621, filed Dec. 13, 2007.
D'Andrea MR, et al (2004). The microglial phagocytic role with specific plaque types in the Alzheimer's disease brain. Neurobiology of Aging 25: 675-683.
Davis, A, et al., "Effect of pinitol treatment on insulin action in subjects with insulin resistance," Diabetes Care 23: 1000-1005 (2000).
Day, G.M., et al., "Polymorphism of Scyllo-Inositol: Joining Crystal Structure Prediction with Experiment to Elucidate the Structures of Two Polymorphs", Crystal Growth & Design, 2006, vol. 6, pp. 2301-2307.
Demattos, R.B., et al., "Clusterin Promotes amyloid plaque formation and is critical for neuritic toxicity in a mouse model of Alzheimer's disease", PNAS, 2002, vol. 99, No. 16, pp. 10843-10848.
Ding, J.D., et al., "Targeting age-related macular degeneration with Alzheimer's disease based immunotherapies: Anti-amyloid-β antibody attenuates pathologies in an age-related macular degeneration mouse model", Vision Res, 2002, vol. 48, No. 3, pp. 339-345.
Dodart J., et al., "Immunization reverses memory deficits without reducing brain Aβ burden in Alzheimer's disease model," Nature Neuroscience 5(5): 452-457 (2002).
Dovey H.F., et al., "Functional gamma-secretase inhibitors reduce beta-amyloid peptide levels in brain," Journal of Neurochemistry 76: 173-181 (2001).
Dworsky, P., English Abstract of : Die Uberfuhrung von myo-Inosit in chinoide Substanzen in Pseudomonas beiherinckii, 1. Mitt., Monatshefte fur Chemie, 1. 1327, (1969).
Egido-Gabás, M., et al., "New Aminocyclitols as modulators of glucosylceramide metabolism", Org. Biomol. Chem, 3:1195-1201 (2005.).
Einat, H., et al., "Inositol reduces depressive-like behaviors in two different animal models of depression.," Psychopharmacology (Berl). 144: 158-62 (1999).

Einat, H., et al., "Chronic inositol treatment reduces depression-like immobility of Flinders Sensitive Line rats in the forced swim test," Depress Anxiety. 15: 148-51 (2002).
Esch, F et al., "Cleavage of amyloid β peptide during constitutive processing of its precursor," Science 248: 1122-1124 (1990).
European Search Report and European Search Opinion for EP 10 01 0477 dated Mar. 8, 2011.
Extended European Search Report for related EP 10010477 dated Mar. 15, 2011.
Fassbender, K., et al., "The LPS receptor (CD14) links innate immunity with Alzheimer's disease," FASEB J 18: 203-5 (2004).
Ferrer, I., et al., "Neuropathology and pathogenesis of encephalitis following amyloid-β immunization in Alzheimer's disease," Brain Pathol 24: 11-20 (2004).
Fisher, S.K., et al. , "Inositol and higher inositol phosphates in neural tissues: homeostasis, metabolism and functional significance," Journal of Neurochemistry, 2002, 82, 736-754.
Fox, N.C., et al., Effects of Aβ immunization (AN1792) on MRI measures of cerebral volume in Alzheimer disease, Neurology 2005, 64: 1563-1572.
Frahm, J., et al., "Localized proton NMR spectroscopy of brain tumors using short-echo time STEAM sequences", J Comput Assist Tomogr, 1991, vol. 15, No. 6, pp. 915-922.
Frey, R., et al., "Myo-inositol in depressive and healthy subjects determined by frontal 1H-magnetic resonance spectroscopy at 1.5 tesla," J Psychiatr Res. 32: 411-20 (1998).
Fujiwara, H., et al., "Alpha-Synuclein is phosphorylated in synucleinopathy lesions", Nat Cell Biol, 2002, vol. 4, No. 2, pp. 160-162.
Fux, M., et al., "Inositol treatment of obsessive-compulsive disorder," Am. J. Psychiatry 153: 1219-1221 (1996).
Fux, M, et al., "Inositol versus placebo augmentation of serotonin reuptake inhibitors in the treatment of obsessive-compulsive disorder: a double-blind cross-over study," Int J Neuropsychopharmacol. 2: 193-195 1999).
Gamblin, T.C., et al., Proc Natl Acad Sci 100: 10032-7 (2003).
Gani, D., et al., Lithium and myo-inositol homeostasis. Biochimica et Biophysica Acta. 1177: 253-269 (1993).
Geerts, H., NC-531. Curr Opin in Investigational Drugs 5(1): 95-100 (2004).
Gelber, D., et al., Effect of inositol on bulimia nervosa and binge eating. Int. J. Eat. Disord. 29(3): 345-348 (2001).
Geldmacher, M.D., D.S., "Long-Term Cholinesterase Inhibitor Therapy for Alzheimer's Disease: Practical Considerations for the Primary Care Physician," Primary Care Companion, J. Clin. Psych., 2003; 5(6), pp. 251-259.
Gerli, S., et al., "Effects of inositol on ovarian function and metabolic factors in women with PCOS: a randomized double blind placebo-controlled trial," Eur Rev Med Pharmacol Sci. 7: 151-9 (2003).
Ghosh, A.K., et al., "E-Secretase as a Therapeutic Target for Inhibitor Drugs" Current Medicinal Chemistry, 2002, vol. 9, pp. 1135-1144.
Ghosh, A.K., et al., "Structure-Based Design: Potent Inhibitors of Human Brain Memapsin 2 (β-Secretase)" J. Med Chem, 2001, vol. 44, No. 18, pp. 2865-2868.
Gilman, S., et al., AN1792(OS-21)-201 Study Team. (2005). Clinical effects of Abeta immunization (AN1792) in patients with AD in an interrupted trial. Neurology 64: 1553-62.
Goedert, M., et al., "Alpha-synuclein and neurodegenerative diseases," Nat Rev Neurosci, 2001, vol. 2, pp. 492-501.
Golde, T.E., Alzheimer disease therapy: Can the amyloid cascade be halted? J. Clin. Invest. 111, 11-18, 2003.
Goodman, et al. "Perspectives in Peptide Chemistry" pp. 283-294 (1981).
Gordon, D.J., et al., "Inhibition of Beta Amyloid(4) fibrillogenesis and Disssembly of Beta-Amyloid(4) fibrilsby short Beta-amyloid congeners containinedn-methyl amino acids at alternate residues" Biochemistry 2001 40 8237-8245.
Graf, E., et al., "Effects of phytate on mineral bioavailability in mice" Journal of Nutrition 114(7) 1192-1198 (1984).

(56) References Cited

OTHER PUBLICATIONS

Grases, F., et al., "Influence of concomitant food intake on the excretion of orally administered myo-inositol hexaphosphate in humans" J Med Food 9 (1) 2006 72-76.
Grases, F., et al., "intracellular and extracellular myo-inositol hexakisphosphate (InsP6) from rats to humans" Anticancer Res. May-Jun. 2005 25 (3c) 2593-2597.
Greiner Declaration of Oct. 12, 2007 from U.S. Appl. No. 10/787,621, filed Dec. 10, 2007.
Greiner, R., et al., "Pathway of Dephosphorylation of myo-inositol hexakisphosphate by phytases of legune seeds" J. Agric. Food Chem. 2002 50 6865-6870.
Greiner, R., "Degradation of myo-inositol hexakisphosphate by a phytate-degrading enzyme from Pantoea agglomerans" The Protein Journal 33(8) 577 (2004).
Greiner, R., et al., "Myo-inositol phosphate isomers generated by the action of a phytase from a Malaysian waste-water bacterium" Protein J. 2007, 26(8): 597-84.
Greiner, R., et al., "myo-inositol phosphate isomers generated by the action of a phytate-degrading enzyme from Klebsiella terrigena on phytate" Can J. Microbiol 52 759-768 (2006).
Greiner, R., et al., Pathway of phytate dephosphorylation by B-propeller phytases of different origins Can. J. Microbiol 53 488-495 (2007).
Greiner, R., et al., "Stereospecificity of myo-inositol hexakisphosphate dephosphorylation by phytate-degrading enzymes of cereals" J of Food Biochemistry 25 (2001) 229-248.
Greiner, R., et al., "Stereospecificity of myo-inositol hexakisphosphate desphosphorylation by a phytate-degrading enzyme of Baker's Yeast" J. Agric. Food Chem 2001 49 2228-2233.
Greiner, R., et al., "Stereospecificity of myo-inositol hexakisphosphate desphosphorylation by a phytate-degrading enzyme of *Escherichia coli*" Journal of Biotechnology 84 (2000) 53-62.
Griffith, H.R., et al., "Elevated brain scyllo-inositol concentrations in patients with Alzheimer's disease" NMR in Biomedicine Feb. 13, 2007, 20(8): 709-716.
Groenen P.M.W, et al., "Kinetics of myo-inositol loading in women of reproductive age," Ann. Clin. Biochem. 40: 79-85 (2003).
Guillozet, A., et al., "Neurofibrillary tangles, amyloid, and memory in aging and mild cognitive impairment," Arch Neurol May 2003; 60: 729-36 (2003).
Haass, C., et al., DJ. (1992). Nature 359: 322-325.
Hager, K., et al., "Kinetics and specificity of the renal Na+/myo-inositol cotransporter expressed in Xenopus Oocytes," J. Membr. Biol. Jan. 1995; 143 (2): 103-13.
Hallman, M., et al., "Respiratory distress and inositol supplementation in preterm infants," Arch Dis Child 61(11): 1076-83 (1986).
Hallman, M., et al., "Inositol supplementation in respiratory distress syndrome: relationship between serum concentration, renal excretion, and lung effluent phospholipids," J Pediatr 110(4): 604-610 (1987).
Hallman, M., et al., "Inositol supplementation in respiratory distress syndrome," Lung 168 Suppl: 877-882 (1990).
Hallman, M., et al., Inositol supplementation in premature infants with respiratory distress syndrome. (1992). N Engl J Med 326(19): 1233-9.
Hipps, P.P., et al., "The identification of myo-inositol:NAD(P) oxidoreductase in mammalian brain," *Biochemical and Biophysical Research Communications*, vol. 68, No. 4, 1976.
Hipps, P.P., et al., "Interconversion of myo- and scyllo-inositol with simultaneous formation of neo-inositol by an NADP dependent epimerase from bovine brain," Biochemical and Biophysical research communications. 1: 340-346 (1977).
Hock, C., et al., "Antibodies against β-amyloid slow cognitive decline in Alzheimer's disease," Neuron 38: 547-554 (2003).
Holub, B.J., "Metabolism and function of myo-inositol and inositol phospholipids," Ann. Rev. Nutr. 6: 563-597 (1986).

Hsaio, K.K., et al., Age-related CNS disorder and early death in transgenic FVB/N mice overexpressing Alzheimer amyloid precursor proteins. *Neuron* 15, 1203-1218 (1995).
Hsiao, K.K.; et al., "Correlative memory deficits, Aβ elevation, and amyloid plaques in transgenic mice," Science 274: 99-102; 1996.
Hu, B., "Synthesis and SAR of bis-statine based peptides as BACE 1inhibitors", Bioorg Med Chem Lett, 2004, vol. 14, No. 13, pp. 3457-3460.
Hu, J., et al., "Design and Synthesis of Statine-Containing BACE Inhibitors", Bioorg Med Chem Lett, 2003, vol. 13, No. 24, pp. 4335-4339.
Hu, L., et al., "The impact of Aβ-plaques on Cortical Cholinergic and Non-cholinergic Presynaptic boutons in Alzheimer's Disease-like Transgenic mice," *Neuroscience* 121, 421-432 (2003).
Ibanez, P., et al., "Causal relation between α-synuclein gene duplication and familial Parkinson's disease" Lancet, 2004, vol. 364, pp. 1169-1171.
Ibsen, L., et al., "In stu localization and osmotic regulation of the Na +-myo-inosytol cotransporter in rat brain," Am. J. Physiol. 271(Renal Fluid Electroclyte Physiol. 40):F877-F885 (1996).
Inoue K., et al., "Cellular localization of Na+/MYO-inositol cotransporter mRNA in the rat brain," NeuroReport 7:1195-1198 (1996).
International Preliminary Report on Patentability for PCT/CA2006/001679 dated Apr. 15, 2008.
International Preliminary Report on Patentability for PCT/CA2007/000900 dated Nov. 21, 2008.
International Preliminary Report on Patentability for PCT/CA2007/001678 dated Mar. 24, 2009.
International Preliminary Report on Patentability for PCT/IB2006/004181 dated Apr. 16, 2008.
International Preliminary Report on Patentability for related PCT/CA2007/002118 dated May 26, 2009.
International Preliminary Report on Patentability for related PCT/CA2009/001448 dated Apr. 12, 2011.
International Preliminary Report on Patentability for related PCT/CA2004/000272 dated Nov. 25, 2005.
International Preliminary Report on Patentability PCT/CA2008/00685 dated Oct. 13, 2009.
International Search Report for PCT/CA2004/000272 dated Jun. 3, 2004.
International Search Report for PCT/CA2005/001744 dated Feb. 17, 2006.
International Search Report for PCT/CA2006/001679 dated Jan. 29, 2007.
International Search Report for PCT/CA2007/000900 dated Aug. 24, 2007.
International Search Report for PCT/CA2007/001678 dated Dec. 14, 2007.
International Search Report for PCT/CA2007/002118 dated Mar. 7, 2008.
International Search Report for PCT/CA2008/000683 dated Jul. 11, 2008.
International Search Report for PCT/CA2008/000684 dated Jul. 24, 2008.
International Search Report for PCT/CA2008/000685 dated Jul. 28, 2008.
International Search Report for PCT/CA2008/000703 dated Jul. 15, 2008.
International Search Report for PCT/CA2009/001448 dated Jan. 8, 2010.
International Search Report for PCT/IB2006/004181 dated Nov. 21, 2007.
International Search Report for PCT/IB2007/001929 dated Jan. 22, 2008.
International Search Report for PCT/US2009/056985 dated Nov. 27, 2009.
International Search Report for PCT/US2009/057003 dated Feb. 17, 2010.
International Search Report PCT/CA2007/000395 dated Jun. 8, 2007.

(56) References Cited

OTHER PUBLICATIONS

Irizarry, et al., "APP$_{Sw}$ transgenic mice develop age-related Aβ deposits and neuropil abnormalities, but no neuronal loss in CA1," J. Neuropathol. Exp. Neurol. 56, 965-973, 1997.
Irving, G.C.J., et al., "Inositol phosphate phosphatases of microbiological origin. Some properties of a partially purified bacterial (Pseudomonas) phytase," Aust. J. Biol. Sci 24 547-557 (1971).
Janciauskiene, S., et al., "Alzheimer's peptide and serine proteinase inhibitors in glaucoma and exfoliation syndrome", Documenta Ophthalmologica, 2003, vol. 106, pp. 215-223.
Janus, C., et al. "Aβ peptide immunization reduces behavioural impairment and plaques in a model of Alzheimer's disease," Nature 408: 979-982 (2000).
Jen, L. S., et al., "Alzheimer's peptide kills cells of retina in vivo" Nature, 1998, vol. 392, pp. 140-141.
Jo, E., et al., "α-Synuclein Membrane Interactions and Lipid Specificity", J Biol Chem, 2000, vol. 275, pp. 34328-34334.
Josien, H., "Recent Advances in the development of γ-secretase inhibitors," Current Opinion in Drug Discovery & Development, 2002 5(4):513-525.
Kaiser, L., et al., Scyllo-inositol in normal aging human brain: 1H magnetic resonance spectroscopy study at 4 Tesla. NMR Biomed. 18: 51-55 (2005).
Kaplan, Z., et al., Inositol treatment of post-traumatic stress disorder. Anxiety 2(1): 51-52, (1996).
Katsuno, M., et al., "Transgenic mouse models of spinal and bulbar muscular atrophy (SBMA)," Cytogenetic and Genome Research, 2003, vol. 100, pp. 243-251.
Kayed, R., et al., "Common Structure of Soluble amyloid oligomers implies common mechanism of pathogenesis," *Science* 300, 486-489 (2003).
Kersting, et al., "Identification of the Inositol Isomers Present in Tetrahymena," J Eukaryot Microbiol 50:164-168 2003.
Kheterpal, I., et al., "Structural features of the Abeta amyloid fibril elucidated by limited proteolysis," Biochemistry, 2001 40(39):11757.
Kiely, D.E., et al., Cyclization of D-xylo-Hexos-5-ulose, a Chemical Model for the Biosynthesis of myo- and scyllo-Inositols, Communications to the Editor (received Mar. 20, 1968), *Journal of the American Chemical Society*, 90:12: 3289-3290, Jun. 5, 1968.
Kierstead, "Alzheimer's disease: Inositol and Amyloid-Beta Interactions," Alzheimer Society of Canada Research Program. Research Grants and Training Awards (2003).
Kim J.I., et al., "Effects of pinitol isolated from soybeans on glycaemic control and cardiovascular risk factors in Korean patients with type II diabetes mellitus: a randomized controlled study," Eur. J. Clin. Nutr. 59: 456-458 (2005).
Kimberly, W.T., et al., "γ-Secretase is a membrane protein complex comprised of presenilin, nicastrin, aph-1, and pen-2", Proc. Natl Acad. Sci, 2003, vol. 100, pp. 6382-6387.
Kinnard, R.L., et al., "Characterization of scyllo-inositol-containing phosphatidylinositol in plant cells.," Biochem Biophys Res Comm, 2003, vol. 210, pp. 549-555.
Kirkitadze, M.D. et al.,"Paradigms shifts in Alzheimer's disease and other neurodegenerative disorders: the emerging role of oligomeric assemblies," *J. Neurosci. Res.* 69, 567-577 (2002).
Klein, W.L., Aβ toxicity in Alzheimer's disease: globular oligomers (ADDLs) as new vaccine and drug targets. Neurochemistry International. 41: 345-352 (2002).
Kofman, O., et al., "The effect of peripheral inositol injection on rat motor activity models of depression," Isr. J. Med. Sci. 29, 580-586, 1993.
Kofman, O., et al., "Chronic dietary inositol enhances locomotor ctivity and brain inositol levels in rats," Psychopharmacology 139: 239-242 (1998).
Koppaka, V., et al., "Accelerated accumulation of amyloid beta proteins on oxidatively damaged lipid membranes," *Biochemistry* 39, 10011-10016 (2000).
Kruger, R., et al., "Ala30Pro mutation in the gene encoding alpha-synuclein in Parkinson's disease", Nat Genet, 1998, vol. 18, No. 2, pp. 106-108.
Lambert, M.P., et al., "Diffusible, non-fibrillar ligands derived from Abeta1-42 are potent central nervous system neurotoxins," *Proc. Natl. Acad. Scie USA* 95, 6448-6453 (1998).
Lanctôt, K.L., et al., "Efficacy and Safety of Cholinesterase Inhibitors in Alzheimer's Disease: A meta-analysis," CMAJ, Sep. 16, 2003; 169(6), pp. 557-564.
Lanz, T., et al., "Studies of Aβ pharmacodynamics in the brain, cerebrospinal fluid, and plasma in young (plaque-free) Tg2576 mice using the γ-secretase inhibitor," JPET 309: 49-55 (2003).
Larner, J., et al., "Inositol dehydrogenase from *Aerobacter aerogenes,*" Archives of Biochemistry and Biophysics, vol. 60, pp. 352-363 (1956).
Lee, H.J., et al., "Beta-Secretase (BACA1) Inhibitors from Sanguisorbae Radix", Arch Pharm Res, 2005, vol. 28, No. 7, pp. 799-803.
Leissring, M.A., et al., "Enhanced proteolysis of β-amyloid in APP transgenic mice prevents plaque formation, secondary pathology and premature death," Neuron 40, 1087-1093 (2003).
Letter dealing with oral proceedings for related European Patent Application No. 04715226 dated Aug. 29, 2008.
Levine, J., et al., "Inositol 6 g daily may be effective in depression but not in schizophrenia," Hum. Psychopharmacol. 8(1): 49-53 (1993).
Levine, J., et al., "Inositol treatment raises CSF inositol levels," Brain Research 627: 168-170 (1993).
Levine, J., et al., "CSF inositol in schizophrenia and high dose inositol treatment of schizophrenia," Eur Neuropsychopharmacol. 4: 487-490 (1994).
Levine, J., et al. "The effect of inositol on cognitive processes and mood states in normal volunteers," Eur. N-Psychopharmacol. 4(3): 418-419 (1994).
Levine, J., et al. "Double-blind, controlled trial of inositol treatment of depression," The Am. J. Psych. 152(5) 792-794 (1995).
Levine, J., et al. "Inositol may worsen attention deficit disorder with hyperactivity," Hum. Psychopharmacol. 10: 481-484 (1996).
Levine, J., et al. Lack of effect of 6 gm inositol treatment on post-ECT cognitive function in humans. J. Psychiatr. Res. 29: 487-489 (1996).
Levine, J., et al. "Inositol treatment of autism," J. Neural. Transm. 104(2-3): 307-310 (1997).
Levine, J., et al. "Combination of inositol and serotonin reuptake inhibitors in the treatment of depression," Biol. Psychiatry 45(3): 270-3 (1999).
Levine, J., "Controlled trials of inositol in psychiatry," European Neuropsychopharmacology, 1997, vol. 7, pp. 147-155.
Li, Peter P., et al., "In Vivo and ex vivo effects of antidepressants on Rat Brain Membrane-Bound Phosphatidylinositol Synthetase Activity," *Neurochemical Research*, 13, 8, 1988, pp. 789-795.
Li, R., et al., "Amyloid β peptide load is correlated with increased β-secretase activity in sporadic Alzheimer's disease patients", Proc. Natl. Acad. Sci. USA, 2004, vol. 101, No. 10, pp. 3632-3637.
Lim, G.P., et al., "The Curry Spice Curcumin Reduces Oxidative Damage and Amyloid Pathology in an Alzheimer Transgenic Mouse", J Neurosci, 2001, vol. 21, No. 21, pp. 8370-8377.
Lim, P.E., et al., "The phytases. II. Properties of phytase fractions F1 and F2 from wheat bran and the myo-inositol phosphates produced by fraction F2" Biochim. Biophys. Acta 302 316-328 (1973).
Lombardo, J.A., et al., "Amyloid-beta antibody treatment leads to rapid normalization of plaque-induced neuritic alterations," *J Neurosci.* 23, 10879-10883 (2003).
Lubrich, B., et al., "Differential expression, activity and regulation of the sodium/myo-inositol cotransporter in astrocyte cultures from different regions of the rat brain," Neuropharmacol. 39(4): 680-690 (2000).
Luibl, V., et al., "Drusen deposits associated with aging and age-related macular degeneration contain nonfibrillar amyloid oligomers", J Clin Invest, 2006, vol. 116, No. 2, pp. 378-385.

(56) References Cited

OTHER PUBLICATIONS

Magasanik, B., et al., "The stereochemistry of an enzymatic reaction: the oxidation of l-, d-, and epi-inositol by acetobacter suboxydans," *Journal of Biological Chemistry*, pp. 173-188; 1947.

Markesbery, W.R., "The role of oxidative stress in Alzheimer's disease," (1999). Arch Neurol 56: 1449-52.

Marty, M.A., et al., Air Toxics Hot Spots Program Risk Assessment Guidelines, Part IV, Final Draft, of Five of Environmental Protection Agency, California Environmental Protection Agency, 2000, 10 pages.

Masliah, E et al., "Aβ vaccination effects on plaque pathology in the absence of encephalitis in Alzheimer disease," Neurology 64(1): 129-131 (2005).

Mayeux, B., et al., "Plasma amyloid β-peptide 1-42 and incipient Alzheimer's disease," Ann. Neurol., 46, 412-416, 2001.

McAdam, K.P.W.J., et al., "Association of amyloidosis with erythema nodosum leprosum reactions and recurrent neutrophil leucocytosis in leprosy", Lancet, 1975, vol. 306, pp. 572-573.

McGeer, P.L., et al., "Local neuroinflammation and the progression of Alzheimer's disease," Journal of NeuroVirology 8: 529-538 (2002).

McGowan, E., et al., (2005). Neuron 47: 191-199.

McKhann, G., et al., "Clinical diagnosis of Alzheimer's disease: Report of the NINCDS-ADRDA Work Group under the auspices of Department of Health and Human Services Task Force on Alzheimer's Disease", Neurology, 1984, vol. 34, pp. 939-944.

McLaurin Declaration of Aug. 15, 2006 from U.S. Appl. No. 10/787,621, filed Aug. 24, 2006.

McLaurin, J., et al., "Inositol stereoisomers stabilize an oligomeric aggregate of Alzheimer amyloid β peptide and inhibit a β-induced toxicity," J. Biol. Chem. 275(24): 18495-18502 (2000).

McLaurin, J., et al.,Phosphatidylinositol and inositol involvement in Alzheimer amyloid-β fibril growth and arrest, J. Mol. Biol. 278, 183-194, 1998.

McLaurin, J., et al., "Review: Modulating Factors in Amyloid-β Fibril formation," Journal of Structural Biology, vol. 130, pp. 259-270, 2000.

McLaurin, J., et al., "Therapeutically effective antibodies against amyloid β peptide target amyloid-β residues 4-10 and inhibit cytotoxicity and fibrillogenesis," Nature Medicine 8, 1263-1269, 2002.

McLaurin, J., et al., "A Membrane disruption by Alzheimer beta-amyloid peptides mediated through specific binding to either phospholipids or gangliosides. Implications for neurotoxicity," *J. Biol. Chem.* 271, 26482-26489 (1996).

McLaurin, J., et al., "Cyclohexanol inhibitors of Abeta aggregation prevent and reverse Alzheimer phenotype in mouse model" Nature Medicine Jul. 2006 12(7) 801-808.

McLaurin, J., et al. A Characterization of the interactions of Alzheimer beta-amyloid peptides with phospholipid membranes. *Eur. J. Biochem.* 245, 355-363 (1997).

McLean, C.A., et al., "Soluble pool of Abeta amyloid as a determinant of severity of neurodegeneration in Alzheimer's disease," *Ann Neurol.* 46, 860-866 (1999).

McPhee, et al., "Studies of inositol analogues as inhibitors of the phosphoinositide pathway, and incorporation of 2-deoxy-2-fluoro-myo-inositol to give analogues of phosphatidylinositor intermediates," Biochem J. 1991 277 407-412.

Metaxas, N.E., "Familial Mediterranean fever and amyloidosis", Kidney Int., 1981, vol. 20, pp. 676-685.

Michaelis, T., et al., "Identification of Scyllo-Inositol in Proton NMR Spectra of Human Brain In Vivo," NMR in Biomedicine, vol. 6, 105-109 (1993).

Mizuno, T., et al., "Cholesterol-dependent generation of a seeding amyloid beta-protein in cell culture," *J. Biol. Chem.* 274, 15110-15114 (1999).

Moats, R.A., et al., "Abnormal Cerebral Metabolite Concentrations in Patients with Probable Alzheimer Disease," MRM. 32: 110-115 (1994).

Moechars, D., et al., "Early Phenotypic Changes in Transgenic Mice That Overexpress Different Mutants of Amyloid Precursor Protein in Brain," *J. Biol. Chem.*, 274, 6483-6492 (1999).

Mohs, R.C., et al., "The Alzheimer's Disease Assessment Scale", Int Psychogeriatr, 1996, vol. 8, No. 2, pp. 195-203.

Moore, C.M., et al., "Effects of myo-Inositol Ingestion on human Brain myo-Inositol Levels: A Proton Magnetic Resonance Spectroscopic Imaging Study," Biol Psychiatry. 45: 1197-1202 (1999).

Morgan, D., et al., "A β peptide vaccination prevents memory loss in an animal model of Alzheimer's disease," Nature 408: 982-985 (2000).

Morgan, B. A., et al., Ann. Rep. Med. Chem. 24:243 (1989).

Morris, R., "Development of a water-maze procedure for studying spatial learning in the rat," *J. Neurosci Methods* 11, 47-60 (1984).

Mount, H.T.J., "Progressive sensorimotor impairment is not associated with reduced dopamine and high energy phosphate donors in a model of ataxia-telangiectasia," *J Neurochem* 88:1449-1454, Mar. 15, 2004.

Moyer, J.R., Jr., et al., Methods for whole-cell recording from visually preselected neurons of perirhinal cortex in brain slices from young and aging rats. *J Neurosci Methods*.86, 35-54 (1998).

Murthy, P.P.N., et al., "Evidence of two isomers of phosphatidylinositol in plant tissue", Plant Physiol, vol. 98, pp. 1498-1501 (1992).

Nakano, T., et al., "The pathway of dephosphorylation of myo-inositol hexaisphosphate by phytases from wheat bran of *Triticum aestivum* L. cv. Nourin #61" Biosci Biotechnol Biochem 64(5) 995-1003 (2000).

Narumi, K., et al., "Gaschromatographic Analysis of Free myo- and scyllo-Inositols in Animal Tissues," Japan. J. Exp. Med. 39:399-407 (1969).

Naslund, J., et al., "Correlation between elevated levels of amyloid β-peptide in the brain and cognitive decline", JAMA, 2000, vol. 283, pp. 1571-1577.

Nemets B., et al., "Inositol addition does not improve depression in SSRI treatment failures," J. Neural. Transm. 106: 795-798 (1999).

Nemets, B., et al., "Myo-inositol has no beneficial effect on premenstrual dysphoric disorder," World J. Biol. Psychiatry. 3(3): 147-149 (2002).

Nestler, J.E., et al., "Ovulatory and metabolic effects of D-chiro-inositol in the polycystic ovary syndrome," N. Engl. J. Med. 340(17): 1314-20 (1999).

Nicoll, J.A.R., et al., "Neuropathology of human Alzheimer disease after immunization with amyloid-β peptide: a case report," Nature Medicine 9(4): 448-452 (2003).

Office Action for related Canadian Application No. 2 516 563 dated Nov. 19, 2010.

Office Action for related Japanese Application No. 2006 501433 dated Jun. 30, 2010, 4 pages.

O'Hare, E., et al., "Utilization of an operant model of food reinforced behavior involving neuropeptide Y, insulin, 2-deoxy-d-glucose, and naloxone," Behavioral Pharmacology, 7: 742-753 (1996).

Ohno, M., et al., "BACE1 Deficiency rescues memory deficits and cholinergic dysfunction in a mouse model of Alzheimer's disease," Neuron 41: 27-33 (2004).

Orgogozo, J.M., et al., "Subacute meningoencephalitis in a subset of patients with AD after Aβ42 immunization," Neurology 61(1): 46-54 (2003).

Pak, Y., et al., "In vivo conversion of [$^3$H]myoinositol to [$^3$H]chiroinositol in rat tissues", J Biol Chem, 1992, vol. 267, pp. 16904-16910.

Palatnik, A., et al., "Double-blind, controlled, crossover trial of inositol versus fluvoxamine for the treatment of panic disorder," J. Clin. Psychopharmacol. 21(3): 335-339 (2001).

Patani, G.A., et al., "Bioisosterism: A rational approach in drug design" Chemical Reviews, 1996, vol. 96, No. 8, pp. 3147-3176.

Patey, S.J., et al., "Novel heparan sulphate analogues: inhibition of beta-secretase cleavage of amyloid precursor protein", Biochem Soc Trans, 2005, vol. 33, No. 5, pp. 1116-1118.

Patish I, Y., et al., "Differential uptake of myo-inositol in vivo into rat brain areas," European Neuro-psychopharmacology. 6: 73-75 (1996).

(56) References Cited

OTHER PUBLICATIONS

Paulson, H., et al., "Polyglutamine disease and neuronal cell death," PNAS, 2000, vol. 97, No. 24, pp. 15957-12958.
Phinney, A., et al., "No hippocampal neuron or synaptic bouton loss in learning-impaired aged β-amyloid precursor protein-null mice," Neuroscience 90, 1207-1216 (1999).
Phinney, A.L., et al., "In vivo reduction of amyloid-beta by a mutant copper transporter," Proc Natl Acad Sci U S A. 100, 14193-14198 (2003).
Plimmer, R.H.S., et al., "The hydrolysis of organic phosphorus compounds by dilute acid and by dilute alkali," Ludwig Mond Research Laboratory for Biological Chemistry, Institute of Physiology, University College, London, Nov. 23, 1912, pp. 72-80.
Xo-Rong et al, "NMR and CD Studies of the interaction between inositol and β-amyloid peptide." Proceedings 2002 II of $81^{st}$ Spring Meeting of the Chemical Society of Japan, 2002, 1418, 2 pages.
Ramaley, R., "Purification and Properties of Bacillus subtilis inositol dehydrogenase," Journal of Biological Chemistry, vol. 254, No. 16, 1979, pp. 7684-7690.
Reaume, A.G., et al, (1996) Nature Genetics, 13 43-47.
Reber, G. et al., "myo-Inositol transport system in Pseudomonas putida," Journal of Bacteriology, Sep. 1977, p. 872-875, vol. 131, No. 3.
Redwine, J.M., et al., "Dentate gyrus volume is reduced before onset of plaque formation in PDAPP mice: A magnetic resonance microscopy and stereologic analysis" PNAS, 2003, vol. 100, No. 3, pp. 1381-1386.
Reiner, A., et al., "Differential loss of striatal projection neurons in Huntington disease", Proc. Natl. Acad. Sci, 1988, vol. 85, pp. 5733-5737.
Reixach, N., et al., "Inhibition of β-amyloid-induced neurotoxicity by imidazopyridoindoles derived from a synthetic combinatorial library," Journal of Structural Biology, 2000, vol. 130, pp. 247-258.
Reply to Communication from the Examination Division for related European Patent Application No. 04715226 dated Jun. 11, 2007.
Reply to Communication from the Examination Division for related European Patent Application No. 04715226 dated Jun. 20, 2006.
Reply to communication from the Examining Division for related European Application No. 05808109 dated Apr. 16, 2009.
Reply to communication from the Examining Division for related European Application No. 07710726 dated May 18, 2010.
Reply to Result of consultation by telephone/ in person for related European Patent Application No. 04715226 dated Sep. 25, 2008.
Reply to Summons to attend Oral Proceedings for related European Patent Application No. 04715226 dated Aug. 18, 2008.
Response to Communication dated Mar. 23, 2011 enclosing Extended European Search report issued in EP 1001047.7, dated Oct. 20, 2011.
Response to Communication pursuant to Article 94(3) EPC for related EP 09 005 295 dated Sep. 1, 2010, dated Mar. 1, 2011.
Response to Extended European Search Report in related European Application No. 06850456, dated Apr. 29, 2009, dated Jul. 28, 2009.
Result of consultation by telephone/ in person for related European Patent Application No. 04715226 dated Sep. 9, 2008.
Richards, M.H., et al., "Epi-inositol is biochemically active in reversing lithium effects on eytidine monophosphorylphosphatidate (CMP-PA)," J. Neural Transm 103, 1281-1285, 1996.
Richardson, R.L., et al., "Behavioral and histopathological analyses of ibuprofen treatment on the effect of aggregated Aβ1-42 injections in the rat," Brain Research, 954: 1-10 (2002).
Riley, et al., "Scyllo-inositol Pentakisphosphate as an analogue of myo-inositol 1,3,4,5,6-pentakisphosphate: chemical sythesis, physicochemistry and biological applications" Chembiochem 2006 7 1114-1122.
Rogers, J., et al., "Complement activation by β-amyloid in Alzhimer's disease," Proc. Natl. Acad. Sci. USA 89: 10016-10020(1992).
Rojo, I., et al., "Macrocyclic peptidomimetic inhibitors of b-secretase (BACE): First X-ray structure of a macrocyclic peptidomimetic-BACE complex", Bioorg Med Chem Lett, 2006, vol. 16, No. 1, pp. 191-195.
Ryals, P.E., et al., "Sodium-dependent uptake of [3H]scyllo-inositol by Tetrahymena: Incorporation into phosphatidylinositol, phosphatidylinositol-linked glycans, and polyphosphoinositols", Arch Biochem Biophys, 1999, vol. 366, No. 2, pp. 261-266.
Saddichha, S., et al., "Alzheimer's and non-Alzheimer's dementia: A critical review of pharmacological and nonpharmacological strategies", American Journal of Alzheimer's Disease and Other Dementias, 2008, vol. 23, No. 2, pp. 150-161.
Sarvey, J.M., et al., "Long-term potentiation: studies in the hippocampal slice," J Neurosci Methods 28,109-124 (1989).
Schenk, D., et al., "Immunization with amyloid-beta attenuates Alzheimer-disease-like pathology in the PDAPP mouse," Nature 400: 173-177 (1999).
Schenk, D., "Treatment of Alzheimer's Disease: The Beginning of a New Era", Current Alzheimer Research, 2006, vol. 3, No. 3, pp. 177.
Schmandke, H. "Dietary Phytic Acid Lowers Blood Glucose and Serum Lipid Levels", Ernahrungs Umschau 54:254-257 (2007).
Schott, J.M., et al., "Measuring atrophy in Alzheimer disease: A serial MRI study over 6 and 12 months," Neurology 65: 119-124 (2005).
Scott, H., et al., "Aberrant expression of the glutamate transporter excitory amino acid transporter 1 (EAAT1) in Alzheimer's disease," J Neurosci 22: RC206 (2002).
Seaquist, E., et al., "Identification of a High Concentration of Scyllo-Inositol in the Brain of a Healthy Human Subject Using 1H- and 13C-NMR," MRM. 39: 313-316 (1998).
Seedat, S., et al., "Inositol augmentation of serotonin reuptake inhibitors in treatment-refractory obsessive disorder: an open trial," Int. Clin. Psychopharmacol. 15(4): 244 (1999).
Selkoe, D.J., "Alzheimer's disease is a synaptic failure," Science 298: 789-791 (2002).
Selkoe, D.J., "Alzheimer's disease: genes proteins, and Therapy," Physiol Rev 81 741-766 (2001).
Selkoe, D.J., Deciphering the genesis and fate of amyloid beta-protein yields novel therapies for Alzheimer disease. J. Clin Invest. 110, 1375-1381 (2002).
Shamsuddin, A.M., "Metabolism and cellular functions of IP6:a review" Anticancer Res. Sep.-Oct. 1999; 19 (5A) :3733-6.
Shapiro, J., et al., "Scyllo-Inositol in post-mortem brain of bipolar, unipolar and schizophrenic," J Neural Transm. 107: 603-607 (2000).
Sharma, K., et al., "Complex-1 activity and 18F-DOPA uptake in genetically engineered mouse model of Parkinson's disease and the neuroprotective role of coenzyme Q10", Brain Res Bull., 2006, vol. 70, No. 1, pp. 22-32.
Sherman, W.R., et al., "The Identification of myo-inosose-2 and scyllo-inositol in mammalian tissues," Biochemistry 7, # 2, 819-824 (1968).
Sherman, W.R., et al., "The measurement of myo-inositol, myo-inosose-2 and scyllo-inositol in mammalian tissues," Biochim. Biophys. Acta. 158: 197-205 (1968).
Shetty, H., et al., "Brain accumulation of myo-inositol in the trisomy 16 mouse, an animal model of Down's Syndrome," Biochem. J. 313: 31-33 (1996).
Shetty, H., et al., "Cerebrospinal fluid and plasma distribution of myo-inositol and other polyols in Alzheimer disease," Clinical Chemistry 42:2, 298-302 (1996).
Shetty, H.U., et al., "Capillary Gas Chromatography Combined with Ion Trap Detection for Quantitative Profiling of Polyols in Cerebrospinal Fluid and Plasma," Anal. Biochem., 1995, vol. 224, pp. 279-285.
Shetty, H.U., et al., "Assay of myo-inositol in cerebrospinal fluid and plasma by chemical ionization mass spectrometry of the hexaacetate derivative," Biol. Mass Spec. 23, 440-444, 1994.
Silbernagl, S., et al., Tubular reabsorption of myo-inositol vs. that of D-glucose in rat kidney in vivo et situ. Am. J. Physiol. Renal Physiol. 284: F1181-F1189 (2003).

(56) References Cited

OTHER PUBLICATIONS

Sinha, S., et al., "Cellular mechanisms of b-amyloid production and secretion" Proc. Natl. Acad. Sci, 1999, vol. 96, pp. 11049-11053.
Sinha, S., et al., "Purification and cloning of amyloid precursor protein β-secretase from human brain", Nature, 1999, vol. 402, pp. 537-540.
Slon-Usakiewicz, J.J., et al., Clin. Proteom. J. 2004, 1:227-234.
Spector, R., "The transport and metabolism of scyllo-inositol in the central nervous system," J. Neurochem. 31: 1113-5 (1978).
Spector, R., "Myo-inositol transport through the blood-brain barrier," *Neurochemical Research* 13, 785-787 (1988).
Spillantini, M.G., et al., "Assignment of human alpha-synuclein (SNCA) and beta-synuclein (SNCB) genes to chromosomes 4q21 and 5q35," Genomics, 1995, vol. 27, No. 2, pp. 379-381.
Spillantini, M.G., et al., "α-Synuclein in Lewy bodies," Nature, 1997, vol. 388, pp. 839-840.
Stanton, P.K., et al., "Norepinephrine regulates long-term potentiation of both the population spike and dendritic EPSP in hippocampal dentate gyrus," *Brain Res Bull.* 18, 115-119 (1987).
Strange, K., et al., "Osmoregulatory Changes in Myo-Inositol Content and Na+/Myo-Inositol Cotransport in Rat Cortical Astrocytes," GLLA 12: 35-43. (1994).
Summons to attend Oral Proceedings for related European Patent Application No. 04715226 dated Feb. 6, 2008.
Summons to Attend Oral Proceedings Pursuant to Rule 115(1) EPC for related European Application No. 05808109 dated Jul. 21, 2009.
Tainer, J.A., et al., Nature. Nov. 17-23, 1983; 306(5940):284-7.
Tanaka, M., et al., "Trehalose alleviates polyglutamine-mediated pathology in a mouse model of Huntington disease," *Nat. Med.* 10, 148-154 (2004).
Townsend, M., et al., "Orally available compound prevents deficits in memory caused by the Alzheimer Amyloid-Beta oligomer," Annals of Neurology 2006 60(6) 668-676.
Uldry, M., et al., "Identification of a $H^+$-myo-inositol symporter expressed predominantly in the brain," EMBO J. 20: 4467-4477 (2001).
Uldry, M., et al., "The SLC2 family of facilitated hexose and polyol transporters," *Pflugers Acta*, 447, 480-489 (2004).
Uldry, M., et al., "Regulated exocytosis of an H+/myo-inositol symporter at synapses and growth cones," The EMBO Journal. 23:531-540 (2004).
Ulmer, T.S., et al., "Comparison of Structure and Dynamics of Micelle-bound Human—Synuclein and Parkinson Disease Variants," Journal of Biological Chemistry, 2005, vol. 280, No. 52, pp. 43179-43187.
U.S. Appl. No. 12/090,130, filed Oct. 16, 2008, to Cruz, et al. (Not submitted).
U.S. Appl. No. 12/125,498, filed Mar. 22, 2008, to McLaurin. (Not submitted).
U.S. Appl. No. 12/282,030, filed Sep. 8, 2008, to Cruz, et al. (Not submitted).
U.S. Appl. No. 12/301,155, filed Nov. 11, 2008, to Slon-Usakiewicz. (Not submitted).
U.S. Appl. No. 12/396,515, filed Mar. 3, 2009, to McLaurin. (Not submitted).
U.S. Appl. No. 12/438,572, Filed Feb. 24, 2009, to Cruz, et al. (Not submitted).
U.S. Appl. No. 12/445,164, filed Apr. 20, 2009, to Cruz. (Not submitted).
Vadnal, et al., "Promising Psychotherapeutic Effects of the Natural Sugar: Myo-Inositol," Nutritional Neuroscience. vol. 1.21-33 (1998).
Van Calker, D, et al., "The high affinity inositol transport system—implications for the pathophysiology and treatment of bipolar disorder," Bipolar Disorders 2: 102-107 (2000).
Varano, F., et al., "Synthesis and Biological Evaluation of a New Set of Pyrazolo[1,5-c]quinazoline-2-carboxylates as Novel Excitatory Amino Acids Antagonists," J. Med. Chem., 2002, vol. 45, pp. 1035-1044.

Vaucher, E., et al., "Object Recognition Memory and Cholinergic Parameters in Mice Expressing Human Presenilin 1 Transgenes," *Exp. Neurol.* 175, 398-406 (2002).
Viola, A., et al., "High Cerebral scyllo-inositol: a new marker of brain metabolism disturbances induced by chronic alcoholism," Magnetic Resonance Materials in Physics, Biology and Medicine, 2004, vol. 17, No. 1, pp. 47-61.
Vogl, O., et al., "Synthesis of Hexaoxadiamantanes," *The Journal of Organic Chemistry*, vol. 34, No. 1, 204-207, 1969.
Walsh, D.M., et al., "The oligomerization of amyloid β protein begins intracellularly in cells derived from human brain," Biochemistry 39: 10831-10839 (2000).
Walsh, D.M., et al., "Amyloid β-oligomers: their production, toxicity and therapeutic inhibition," Biochem. Soc. Trans. 30: 552-557 (2002).
Walsh, D.M., et al., "Certain inhibitors of synthetic amyloid β-peptide (A β) fibrillogenesis block oligomerization of natural A β and thereby rescue long-term potentiation," J Neurosci. 25: 2455-2462 (2005).
Walsh, D.M., et al., DJ., "Naturally-secreted oligomers of amyloid-β protein potently inhibit hippocampal long-term potentiation in vivo," Nature 416: 535-539 (2002).
Walsh, D.T., et al., "Amyloid-Beta Peptide Is Toxic to Neurons in Vivo via Indirect Mechanisms", Neurobiol Dis, 2002, vol. 10, pp. 20-27.
Wang, H.W., et al., "Soluble oligomers of β-amyloid (1-42) inhibit long-term potentiation but not long-term depression in rat dentate gyrus," Brain Res. 924: 133-140 (2002).
Wang Q, et al., "Block of LTP by naturally secreted and synthetic amyloid β peptide in hippocampal slices is mediated via activation of the kinases C-Jun N-terminal kinase, cyclin-dependent kinase 5, and p38 mitogen-activated protein kinase as well as MGR type 5," J. Neurosci. 24(13): 3370-3378 (2004).
Wang, J., et al., "The levels of soluble versus insoluble brain Aβ distinguish Alzheimer's disease from normal and pathological aging", Exp. Neurol., 1999, vol. 158, pp. 328-337.
Weggen, S., et al., "A subset of NSAIDs lower amyloidogenic Ab42 independently of cyclooxygenase activity," Nature 2001 414(6860) 212-216.
Weissbach, A., Scyllitol Diborate, Communication to the Editor, vol. 23, pp. 329-330, Dec. 30, 1957.
Wentzel, P., et al., "Induction of Embryonic Dysmorphogenesis by High Glucose Concentration, Disturbed Inositol Metabolizm, and Inhibited Protein Kinase C Activity," Teratology 63: 193-201(2001).
Wiltfang, J., et al., Highly conserved and disease-specific patterns of carboxyterminally truncated Abeta peptides 1-37/38/39 in addition to 1-40/42 in Alzheimer's disease and in patients with chronic neuroinflammation *J Neurochem* 81, 481-496 (2002).
Wong, P.C., et al., "Genetically engineered mouse models of neurodegenerative diseases," *Nat. Neurosci.* 5, 633-639 (2002).
Written Opinion of the International Search Authority for related PCT/CA2004/000272 dated Jan. 2004.
Written Opinion of the International Searching Authority for related PCT/CA2007/002118 dated Mar. 7, 2008.
Written Opinion of the International Searching Authority for related PCT/CA2009/001448 dated Jan. 8, 2010.
Written Opinion of the International Searching Authority for related PCT/CA2005/001744 dated May 22, 2007.
Wyss, M., et al., "Biochemical Characterization of Fungal Phytases (myo-Inositol Hexakisphosphate Phosphohydrolases): Catalytic Properties," Applied and Enviromental Microbiology, Feb. 1999, pp. 367-373.
Xun, Z., et al., "Protein expression in a *Drosophila* model of Parkinson's disease" J Proteome Res, 2007, vol. 6, No. 1, pp. 348-357.
Yamashita, T., et al., "Regulation of Na+/myo-inositol cotrasporter gene expression in hyperglycaemic rat hippocampus," Molecular Brain Research 57: 167-172 (1998).
Yanagisawa, K., et al., "GM1 ganglioside-bound amyloid beta-protein (A beta): a possible form of preamyloid in Alzheimer's disease," *Nat. Med.* 1, 1062-1066 (1995).

(56) References Cited

OTHER PUBLICATIONS

Yang, F., et al., "Curcumin Inhibits Formation of Amyloid β Oligomers and Fibrils, Binds Plaques, and Reduces Amyloid in Vivo," J Biol Chem, 2005, vol. 280, No. 7, pp. 5892-5901.
Ye, M., et al., "Transplantation of bone marrow stromal cells containing the neurturin gene in rat model of Parkinson's disease", Brain Res, 2007, vol. 1142, pp. 206-216.
Yoshihda, K., et al., "Cloning and nucleotide sequencing of a 15kb region of the *Bacillus subtilis* genome containing the iol operon," *Microbiology*, (1994) 140, 2289-2298.
Zarranz, J., et al., "The New Mutation, E46K, of α-Synuclein Causes Parkinson and Lewy Body Dementia", Ann Neurol, 2004, vol. 55, pp. 164-173.
Zhang, et al., "Rapid determination of the Binding Affinity and Specificity of the Mushroom Polporus squamosus Lectin Using Frontal Affinity Chromatography Coupled with Electrospray mass spectrometry," Glycoiology 2001 11(2) 141-147.
Zhang, X., et al., "A potent small molecule inhibits polyglutamine aggregation in Huntington's disease neurons and suppresses neurodegeneration in vivo," PNAS, 2005, vol. 102, No. 3, pp. 892-897.
FDA's Orange Book excerpts for Galantamine, pp. 1-6, printed Jul. 14, 2010.
FDA's Orange Book excerpts for Rivastigmine, pp. 1-5, printed Jul. 14, 2010.
Fenili, D et al., "Properties of scyllo-inositol as a therapeutic treatment of AD-like pathology", J. Mol. Med. 85(6) 603-611, 2007.
Freidinger, R. M., "Non-peptide ligands for peptide receptors," TIPS, 10:270, 1989.
Frolich, L. et al., "Treatment with donepezil in Alzheimer patients with and without cerebrovascular disease" J Neurol Sci, 203-204: 137-9, 2002.
Furukawa, Y, et al., "Amyotrophic Lateral Sclerosis Mutations Have the Greatest Destabilizing Effect on the Apo-and Reduced Form of SOD1, leading to Unfolding and Oxidative Aggregation." J Biol Chem. 280(17): 17266-17274, 2005.
Ghosh, A.K., "Structure-based design of cycloamide-urethane-derived novel inhibitors of human brain memapsin 2 (beta-secretase)," Bioorg. Med. Chem. Lett. 15(1) 15-20, 2005.
Guidance for Industry Estimating the Maximum Safe Dose in Initial Clinical Trials for Therapeutics in Adult Healthy Volunteers, US Dept. of HHS/FDA/CDER, Jul. 2005, 30 pages.
Guo, et al., "ALS-Linked Cu/Zn-SOD mutation impairs cerebral synaptic glucose and glutamate transport and exacerbates ischemic brain injury" J. Cereb. Blood Flow &.Metab. vol. 20(3), 463-468, Mar. 2000.
Haccou,P., & Mellis, E., "Tests for Exponentiality" in "Statistical Analysis of Behavioural Data, An approach based on time-structured models"; p. 112-186, Oxford University Press, Oxford, 1992.
Hanessian, SJ J., "Structure-Based Design, Synthesis and Memapsin 2(BACE) Inhibitory Activity of Carbocyclic and Heterocyclic Peptidomimetics," J Med Chem48(16) 5175-5190, 2005.
Hipps, P.P., "The Identification of Myo-Inositol: NAD(P)+Oxidoreductase in Mammalian Brain," Biochemical and Biophysical Research Communications, vol. 68, No. 4, 1976, pp. 1133-1138.
Husson, C., et al., "New Conditions for the synthesis of scyllo-inositol starting with myo-inositol," Carbohyrate Research 307:163-165, 1998.
Isaacks, R.E., et al., "Effect of Osmolality and Myo-inositol Deprivation on the Transport Properties of Myo-inositol in Primary Astrocyte Cultures," Neurochem. Research 22(12): 1461-1469, 1997.
Meyerhoff D, et al., "Elevated scyllo-inositol in adult human brain," In: Proc ISMRM, 4th Scientific Meeting, New York, pp. 954, 1996.
Michaelis, et al., "B-amyloid induced neuroegeneration and protection by structurally diverse microtubule-stablizing agents" The Journal of Pharmacology and Experimental Therapeutics 312: 659-668, 2005.

(OMIM)—Amyotrophic Lateral Sclerosis 1, In Online Mendelian Inheritance in Man, John Hopkins University, No. 105400; http://ncbi.nih.gov/entrez/dispomim.eqi?id+105400 24 pages.
Palmano, K.P., et al., "Free and Lipid myo-inositol in Tissues from Rats with Acute and Less Severe Streptozotocin-Induced Diabetes" Biochem. J., 167: 229-235, 1977.
Pistarà, V., et al., "A new highly diastereoseletive synthesis of epi-inositol from D-galactose," Tetrahedron Letters 41: 3253-3256, 2000.
Polymeropoulos, M.H., et al., "Mutation in the alpha-synuclein gene identified in families with Parkinson's disease", Science 276(5321), 1977, 6 pages.
Porsteinsson Anton, et al., Neurology 78, Suppl. 1, Apr. 2012 and 64th Annual Meeting of the American Academy of Neurology, New Orleans, USA, Apr. 21-28, 2012 (Elan).
Porsteinsson A et al., "Imaging and Cerebrospinal Fluid Biomarker Results of a Phase 2 Dose-Ranging Study of ELND005 (Scyllo-inositol) in Mild to Moderate Alzheimer's Disease" International Conference on Alzheimer's Disease (ICAD) meeting, to be held Jul. 16-21, 2011, Paris, Oral Presentation, Jul. 20, 2011.
Rakhit, R., et al., "Oxidation-induced Misfolding and Aggregation of Superoxide Dismutas and its Implications for Amyotrophic Lateral Sclerosis" J Biological Chemistry 277 (49): 47551-47556, Dec. 6, 2002.
Rao, R.B., et al., "Fixed-dose combination therapy: panacea or poison?," Intensive Care Medicine 24: 283-285, 1998.
Ray, et al., "Small molecule-mediated stabilization of familial amyotrophic lateral sclerosis-linked superoxide dismutase mutants against unfolding and aggregation," Proc. Natl. Acad. Sci. USA., 102:3639-3644, 2005.
Robertson. J., et al., "Pathways to motor neuron degeneration in transgenic mouse models," Biochimie 84: 1151-1160, 2002.
Rubin, L.J., et al., "Characterization of a Mg-Dependent Na-Inositol Co-Transport Process in Cardiac Sarcolemmal Vesicles," J. Mo. Cell Cardiol. 25, 721-31, 1993.
Sarmah, M., et al., "Sulfonate protecting groups. Improved synthesis of scyllo-inositol and its orthoformate from myo-inositol," Carbohydrate Research, 338: 999-1001, 2003.
Salloway et al., "A phase 2 randomized trial of ELND005, scyllo-inositol, in mild to moderate Alzheimer disease," Neurology, 77(13): 1259-1260, 2011.
Salloway et al., "Safety and Efficacy of a Phase 2 Randomized, Placebo-Controlled Dose-Ranging Study of ELND005 (Scyllo-inositol) in Mild to Moderate Alzheimer's Disease", International Conference on Alzheimer's Disease (ICAD) meeting, to be held Jul. 16-21, 2011, Paris, France Poster Presentation # P2-50, Jul. 18, 2011.
Schmidt, P. J., et al., "A Gain of Superoxide Dismutase (SOD) Activity Obtained with CCS, the Copper Metallochaperone for SOD1," J. Biol.Chem. 274(52): 36952-36956, 1999.
Schultz C, "Prodrugs of biologically active phosphate esters," Bioorganic and Medicinal Chemistry 11(6), pp. 885-898, 2003.
Seedat S, Stein D.J., "Inositol augmentation of serotonin reuptake inhibitors in treatment-refractory obsessive disorder: an open trial,". Int. Clin. Psychophamiacol. 14: 353-356 (1999).
Singleton, A. B., et al., "α-Synuclein Locus Triplication Causes Parkinson's Disease", Science 302(5646): 841, 2003.
Smith, A. B. 3rd, et al., "De Novo Design, Synthiesis and X-ray Crystal Structures of Pyrrolinone-Based B-Strand Peptidomimetics," J. Am. Chem. Soc. 116:9947-9962, 1994.
Smith, A. B. 3rd, et al., "Pyrrolinone-Based HIV Protease Inhibitors. Design, Synthesis, and Antiviral Activity: Evidence for Improved Transport," J. Am. Chem. Soc. 117:11113-11123, 1995.
Sonali, P., Jog, et al., "Alkaline phytase from lily pollen: Investigation of biochemical properties," Archieves of Biochemistry and Biophysics, 440 (2005) 133-140.
Stathopulos, P.B., et al, "Cu/Zn superoxide dismutase mutants associated with amyotrophic lateral sclerosis show enhanced formation of aggregates in vitro,"ProcNatlAcadSoc USA. 100(12):7021-7026, 2003.
Stathopulos, P. B., et al., "Calorimetric Analysis of Thermodynamic Stability and Aggregation for Apo and Holo Amyotrophic Lateral

(56) References Cited

OTHER PUBLICATIONS

Sclerosis-associated Gly-93 Mutants of Superoxide Dismutase," J. Biol. Chem. 281(10), 6184-6193, 2006.
Strong, M.J., "The basic aspects of therapeutics in amyotrophic lateral sclerosis," Pharmacology and Therapeutics 98, 379-414, 2003.
Sun, Y et al., Bioorg Med Chem. 16(15), 7177-7184, 2008.
Hirschmann, R., et al., "De Novo Design and Synthesis of Somatostatin Non-Peptide Peptidomimetics Utilizing β-D-Glucose as a Novel Scaffolding," J. Am. Chem. Soc., 1993, 115, 12550-12568.
Takahashi, H et al., "Novel Synthesis of Enantiomerically Pure Natural Inositols and Their Diasteroisomers", Journal of Organic Chemistry, 66(8):2705-2716, 2001.
Tariot, Pierre et al., Neurology 78, Suppl. 1, Apr. 22, 2012, and 64th Annual Meeting of the American Academy of Neurology, New Orleans, USA, Apr. 21-28, 2012 (Elan).
Taylor, D.M., et al.,"Overexpression of Metallothionein Protects Cultured Motor Neurons Against Oxidative Stress, but not Mutant Cu/Zn-Superoxide Dismutase Toxicity," Neurotoxicology 25:779-792, 2004.
Tiwari, A, et. al., "Aberrantly increased hydrophobicity shared by mutants of Cu,Zn-superoxide dismutase in familial amyotrophic lateral sclerosis," J Biol Chem. 280(33):29771-29779, 2005.
Van Reekum et al., "Diagnosis of dementia and treatment of Alzheimers disease. Pharmacologic management of disease progression and cognitive impairment," Can Family Physician, 45: 945-52, 1999.
Weggen, S., et al., "A subset of NSAIDs lower amyloidogenic Ab42 independently of cyclooxygenase activity," Nature 2001, 414 (6860) 212-216.
Wiesinger, H., "Myo-Inositol Transport in Mouse Astroglia-Rich Primary Cultures," Journal of Neurochemistry, vol. 56, No. 5, 1991, pp. 1698-1704.
Xun, Z., et al., "Proteome Response to the Panneural Expression of Human Wild-Type α-Synuclein: A *Drosophila* Model of Parkinson's Disease," J Proteome Res. 7(9): 3911-21, 2008.
D'Alarcao Declaration under 1.132, submitted in U.S. Appl. No. 10/787,621, dated Nov. 28, 2007, 10 pages.
Greiner Declaration under 1.132, submitted in U.S. Appl. No. 10/787,621, dated Dec. 10, 2007, 38 pages.
Summons issued in corresponding application EP 04715226, dated Feb. 6, 2008, 1 page.
Summons issued in corresponding application EP 05808109, dated Jul. 21, 2009, 1 page.
Extended Search Report issued in corresponding application EP06850456, dated Apr. 29, 2009, 9 pages.
Extended Search Report issued in corresponding application EP09005295, dated Jan. 14, 2010, 8 pages.
Response to Extended Search Report in corresponding application EP 06850456, dated Jul. 28, 2009, 4 pages.
Extended Search Report issued in corresponding application EP09818730, dated Mar. 21, 2012, 6 pages.
Extended Search Report issued in corresponding application EP10010477, dated Mar. 8, 2011, 8 pages.
Response filed in corresponding application EP 10010477, dated Oct. 20, 2011, 5 pages.
Office Action issued in corresponding application CA 2,516,563, dated Apr. 23, 2012, 3 pages.
Response to Office Action filed in corresponding application CA 2,516,563, dated Oct. 23, 2012, 8 pages.
European Search Report issued in corresponding application EP 05808109, dated Jun. 17, 2008, 4 pages.
European Search Report issued in corresponding application EP 07710726, dated May 11, 2009, 5 pages.
European Search Report issued in corresponding application EP 07789484, dated May 12, 2009, 3 pages.
European Search Report issued in corresponding application EP 08733752, dated May 4, 2010, 7 pages.
European Search Report issued in corresponding application EP 10000985, dated Mar. 16, 2010, 7 pages.
Office Action issued in corresponding application EP 10010477, dated Jan. 19, 2012, 3 pages.
European Search Report issued in corresponding application EP 09818730.5, dated Mar. 21, 2012, 3 pages.
(Facts: About Depression and Alzheimer's disease, Feb. 10, 2003).
Response filed in corresponding application CA 2,516,563, dated May 19, 2011, 14 pages.
Office Action issued in corresponding application CA 2,516,563, dated Aug. 1, 2011, 2 pages.
Response filed in corresponding application CA 2,516,563, dated Feb. 1, 2012, 14 pages.
Office Action issued in corresponding application CA 2,516,563, dated Apr. 23, 2012, 2 pages.
Response filed in corresponding application CA 2,516,563, dated Oct. 23, 2012, 8 pages.
Declaration of Dr. Dale Schenk, filed in corresponding application EP 04715226, dated Aug. 21, 2008, 31 pages.
Request for Further Processing filed in corresponding application EP 06850456, dated Aug. 30, 2012 and decision to allow request dated Feb. 10, 2012, 14 pages.
Office Action issued in corresponding application EP 06850456, dated Mar. 18, 2012, 4 pages.
Response filed in corresponding application EP 06850456, dated Jun. 20, 2013, 61 pages.
Request for Further Processing filed in corresponding application EP 07710726, dated Jun. 12, 2012, 6 pages.
Response to European Search Report & Written Opinion filed in corresponding application EP 08733752, dated Nov. 29, 2010, 59 pages.
Response filed in corresponding application EP 09005295, dated Jul. 24, 2012, 67 pages.
"Technical Support Document for Exposure Assessment and Stochastic Analysis," Sep. 2000, by OEHHA of Canada.
"Elan and Transition Therapeutics Announce Modifications to ELND005 Phase II Clinical Trials in Alzheimer's Disease," Elan Press Release, Dec. 15, 2009, 2 Pages.
"Elan and Transition Therapeutics Announce Topline Summary Results of Phase 2 and Plans for Phase 3 for ELDN005 (Scyllo-inositol)," Elan Press Release, Aug. 9, 2010, 1 page.
Abulkalam, M. "inositol phosphates have novel anticancer function" Journal of Nutrition 125 725S-732S 1995.
Agam, R. et al. High-dose peripheral inositol raises brain inositol levels and reverses behavioural effects of inositol depletion by lithium, Pharmaol. Biochem. Behav. 49, 341-343, 1994.
Alexakis, A. et al., "A practical, solvent free, one-pot synthesis of C2-symmetrical secondary amines," Tet. Letters, 2004, vol. 45, pp. 1449-1451.
Allan SJR, et al (2004). The effect of inositol supplements on the psoriasis of patients taking lithium: a randomized, placebo-controlled trial. British Journal of Dermatology 150(5): 966-969.
Anderson, R.C., The Catalytic Hydrogenation of Polyhydric Phenols. I. The synthesis of meso-Inositol, Scyllitol and a New Isomeric Cyclitol., Sep. 1948, pp. 2931-2935.
Barak Y, et al (1994). Effects of inositol on lithium-induced EEG abnormalities. Eur. N-Psypharmacol. 4(3): 419.
Barak Y, et al (1996). Inositol treatment of Alzheimer's disease: A double-blind, cross-over placebo controlled trial. Prog. Neuro-Psychopharmacol. & Biol. Psychiatry. 20: 729-735.
Bard F, et al (2000). Peripherally administered antibodies against amyloid β-peptide enter the central nervous system and reduce pathology in a mouse model of Alzheimer disease. Nature medicine 6(8): 916-919.
Barkai IA, et al (1978) Reduced myo-inositol levels in cerebrospinal fluid from patients with affective disorder. Biol Psychiat 13: 65-72.
Beal, M. F. et al., "Experimental Therapeutics in Transgenic Mouse Models of Huntington's Disease," Nature Rev. Neuroscience, 2004, vol. 5, pp. 373-384.
Benjamin J, et al (1995) Double-blind, placebo-controlled, cross-over trial of inositol treatment for panic disorder. Am J Psychiatry. 152: 1084-6.
Benjamin J, et al (1997). Acute inositol does not attenuate m-CPP-induced anxiety, mydriasis and endocrine effects in panic disorder. J. Psychiatry. Res. 31(4): 489-495.

(56) References Cited

OTHER PUBLICATIONS

Benjamin J, Levine J, Fux M, Aviv A, Levy D, Belmaker RH. (1995). Double blind controlled trial of inositol treatment of panic disorder. Am. J. Psychiatry 152(7): 1084-1086.

Benson, M. D. et al., "Serum amyloid a protein in amyloidosis, rheumatic, and neoplastic diseases," Arth. Rheum, 1979, vol. 22, pp. 36-43.

Berry, Gerard T. et al. (2003) Loss of Murine Na+/myo-Inositol Cotransporter Leads to Brain myo-Inositol Depletion and Central Apnea. The Journal of Biological Chemistry. vol. 278, No. 20, Issue of May 16:18297-18302.

Bersudsky Y, et al (1992). The effect of inositol on Li-induced polyuria polydipsia in rats and humans. Human Psychoparm. 7: 403-407.

Bersudsky Y, et al (1999). Epi-Inositol and Inositol Depletion: Two New Treatment Approaches to Affective Disorder. Current Psychiatry Reports 1999 1:141-147.

Best, J. D. et al., "Quantitive Measurement of Changes in Amyloid-beta(40) in the Rat Brain and Cerebrospinal Fluid Following Treatment with the beta-secretase inhibitors L Y-411575 [N2-[(2S)-2-(3,5-Diflurorphenyl)-2-hydroxyethanoyl]-N1-[(7S0-5-methyl-6-oxo-6,7-dihydro-5H-dibenzo[b,d]asepin 7 yl) L alaninamide]" J. Pharmacol Exp. Ther., 2005, vol. 313, No. 2, pp. 902-908.

Boncristiano, S. et al., "Cholinergic changes in the APP23 Transgenic Mouse Model of Cerebral Amyloidosis," The Journal of Neuroscience, 2002, vol. 22, pp. 3234-3243.

Bornemann et al. Transgenic mouse models of Alzheimer's disease, NY Acad. Sci. 908, 260-266.

Bouveault L. Bull. La Societe Chimique Paris 1894 11:44-147.

Braak H, et al (1997). Frequency of stages of Alzheimer-related lesions in different age categories. Neurobiology of Aging 18: 351-357.

Campbell WW, et al (2004). Pinitol supplementation does not affect insulin-mediated glucose metabolism and muscle insulin receptor content and phosphorylation in older humans. J. Nutr. 134: 2998-3003.

Candy, D.J., Occurrence and metamolism of scyllolnositol in the Locust. Biochem.J. 1967, 103, pp. 666-671.

Cannon MJ et al, Anal Biochem. 2004 328(1):67-75.

Carey P, et al (2004). Single Photon Emission Computed Tomography (SPECT) in Obsessive-Complusive Disorder Before and After Treatment with Inositol. Metabolic Brain Disease vol. 19, Nos. 1/2, Jun. 2004 125-134.

Chalifour R.J. et al, "Stereoselective Interactions of Peptide Inhibitors with the Beta Amyloid Peptide" J. Biol. Chem 2003 278(37) 34874-34881.

Chantal, Sophie et al (Jun. 2002). Correlation of Regional Proton Magnetic Resonance Spectroscopic Metabolic Changes With Cognitive Deficits in Mild Alzheimer Disease. Arch Neurol. 59: 955-962.

Chartier-Harlin, M. C. et al., "Alpha-Synuclein locus duplication as a cause of familial Parkinson's Disease," Lancet, 2004, vol. 364, pp. 1167-1169.

Chen, X. et al.,"The Human NACP/α-Synuclein Gene:Chromosome Assignment to 4q21.3-q22 and Taql RFLP Analysis", Genomics, 1995, vol. 26, No. 2, pp. 425-427.

Chen, Y. L. et al., "Thiazole-diamides as potent c-secretase inhibitors", Bioorganic & Medicinal Chemistry Letters, 2007, vol. 17, No. 20, pp. 5518-5522.

Chengappa KN, et al (2000). Inositol as an add-on treatment for bipolar depression. Bipolar Disorder 2(1): 47-55.

Chishti M et al. (2001). Early-onset amyloid deposition and cognitive deficits in transgenic mice expressing a double mutant form of amyloid precursor protein 695. J. Biol Chem. 276: 21562-21570.

Choo-Smith, L.P. et al The interaction between Alzheimer amyloid beta(1-40) peptide and ganglioside GM1-containing membranes. FEBS Lett 402, 95-98 (1997).

Chopdar, A. et al., "Age related macular degeneration", BMJ, 2003, vol. 326, pp. 485-488.

Chou. S. et al., "CGS21680 attenuates symptoms of Huntington's disease in a transgenic mouse model", J. Neurochem, 2002, vol. 93, No. 2, pp. 310-320.

Chung, S-K., Synthesis of all possible regioisomers of scyllo-Inositol phosphate, *Bioorganic & Medicinal Chemistry*, (1999) pp. 2577-2589.

Citron M. (2004). Strategies for disease modification in Alzheimer's disease. Nature Reviews 5: 677-685.

Cleary J, et al (2005). Natural oligomers of the amyloid-β protein specifically disrupt cognitive function. Nat. Neurosci. 8: 79-84.

Clements RS Jr, Diethelm AG, (1979). The metabolism of myo-inositol by the human kidney. J. Lab. Clin. Med. 93(2): 210-219.

Clements RS Jr, et al (1977). Myoinositol metabolism in diabetes mellitus. Effects of insulin treatment. Diabetes 26: 215-221.

Coady MJ, Wallendorff B, Gagnon DG, Lapointe J-Y. (2002). Identification of a novel Na$^+$/myo-inositol cotransporter. J. Biol. Chem. 277: 35219-35224.

Cogram, Patricia, et al. (2002). D-Chiro-inositol is more effective than myo-inositol in preventing folate-resistant mouse neural tube defects. Human Reproduction. 17: 2451-2458.

Cohen, H. et al. (1997). Inositol has behavioural effects with adaptation after chronic administration. J Neural Transm. 104:299-305.

Cohen, Hagit et al (1996). Acute Inositol Induces Anxiety in Rats. Biol Psychiatry. 40:426-427.

Colodny, L. Inositol—clinical applications for exogenous use, Altern. Med Rev. 3 (6): 433-447, 1998.

Communication for the Examining Division for related European Application No. 07710726 dated Aug. 3, 2009.

Communication regarding the transmission of the European Search Report for related European Application No. 06850456 dated Apr. 29, 2009.

d'Alarcao Declaration of Nov. 28, 2007 from U.S. Appl No. 10/787,621, filed Feb. 27, 2003.

Davis A, et al (2000). Effect of pinitol treatment on insulin action in subjects with insulin resistance. Diabetes Care 23: 1000-1005.

Day, G. M. et L., "Polymorphism of Scyllo-Inositol: Joining Crystal Structure Prediction with Experiment to Elucidate the Structures of Two Polymorphs", Crystal Growth & Design, 2006, vol. 6, pp. 2301-2307.

Demattos, R. B. et al. "Clusterin Promotes amyloid plaque formation and is critical for neuritic toxicity in a mouse model of Alzheimer's disease", PNAS, 2002, vol. 99, No. 16, pp. 10843-10848.

Ding, J. D. et al., "Targeting age-related macular degeneration with Alzheimer's disease based immunotherapies: Anti-amyloid-β antibody attenuates pathologies in an age-related macular degeneration mouse model", Vision Res, 2002, vol. 48, No. 3, pp. 339-345.

Dodart J, et al (2002). Immunization reverses memory deficits without reducing brain Aβ burden in Alzheimer's disease model. Nature Neuroscience 5(5): 452-457.

Doraiswamy, P. M., "Non-Cholinergic Strategies for Treating and Preventing Alzheimer's Disease," CNS Drugs, 2002, vol. 16, No. 12, pp. 811-824.

Dovey HF, et al. (2001). Functional gamma-secretase inhibitors reduce beta-amyloid peptide levels in brain. Journal of Neurochemistry 76: 173-181.

Dworsky, P. English Abstract of : Die Uberfuhrung von myo-lnosit in chinoide Substanzen in Pseudomonas beiherinckii, 1. Mitt., *Monatshefte fur Chemie*, 1. 1327, (1969).

Egido-Gabás, M. et al, "New Aminocyclotols as modulators of glucosylceramide metabolism", Org. Biomol. Chem, 3:1195-1201 (2005).

Einat H, et al (1999) Inositol reduces depressive-like behaviors in two different animal models of depression. Psychopharmacology (Berl). 144: 158-62.

Einat H, et al (2002) Chronic inositol treatment reduces depression-like immobility of Flinders Sensitive Line rats in the forced swim test. Depress Anxiety. 15: 148-51.

Elan Corporation Press Release of Dec. 15, 2009—1 page.

Elan Corporation Press Release of Jul. 13, 2009—1 page.

Esch F, et al (1990). Cleavage of amyloid β peptide during constitutive processing of its precursor. Science 248: 1122-1124.

(56) References Cited

OTHER PUBLICATIONS

European Search Report for EP 10 01 0477 dated Mar. 8, 2011.
European Search Report for related EP 09 005 295 dated Jan. 14, 2010.
Fassbender K, et al (2004). The LPS receptor (CD14) links innate immunity with Alzheimer's disease. FASEB J 18: 203-5.
FDA's Orange Book excerpts for Donepezil, pp. 1-3, printed Jul. 14, 2010.
Ferrer I, et al (2004). Neuropathology and pathogenesis of encephalitis following amyloid-β immunization in Alzheimer's disease. Brain Pathol 24: 11-20.
Fisher, S.K., et al. Inositol and higher inositol phosphates in neural tissues: homeostasis, metabolism and functional significance, Journal of Neurochemistry, 2002, 82, 736-754.
Fox, N.C. et al. Effects of Aβ immunization (AN1792) on MRI measures of cerebral volume in Alzheimer disease, Neurology 2005, 64: 1563-1572.
Frahm, J. et al., "Localized proton NMR spectroscopy of brain tumors using short-echo time STEAM sequences", J Comput Assist Tomogr, 1991, vol. 15, No. 6, pp. 915-922.
Frey R, et al (1998) Myo-inositol in depressive and healthy subjects determined by frontal 1H-magnetic resonance spectroscopy at 1.5 tesla. J Psychiatr Res. 32: 411-20.
Frolich, L. et al., "Treatment with donepezil in Alzheimer patients with and without cerebrovascular disease" J Neurol Sci, 2002, vol. 203-204, pp. 137-139.
Fujiwara, H. et al., "Alpha-Synuclein is phosphorylated in synucleinopathy lesions", Nat Cell Biol, 2002, vol. 4, No. 2, pp. 160-162.
Fux M, et al (1996). Inositol treatment of obsessive-compulsive disorder. Am. J. Psychiatry 153: 1219-1221.
Fux M, et al (1999) Inositol versus placebo augmentation of serotonin reuptake inhibitors in the treatment of obsessive-compulsive disorder: a double-blind cross-over study. Int J Neuropsychopharmacol. 2: 193-195.
Gamblin TC, et al (2003). Proc Natl Acad Sci 100: 10032-7.
Gani, David et al. (1993). Lithium and myo-inositol homeostasis. Biochimica et Biophysica Acta. 1177: 253-269.
Geerts H. (2004). NC-531. Curr Opin in Investigational Drugs 5(1): 95-100.
Gelber D, et al (2001). Effect of inositol on bulimia nervosa and binge eating. Int. J. Eat. Disord. 29(3): 345-348.
Gerli S, et al (2003) Effects of inositol on ovarian function and metabolic factors in women with PCOS: a randomized double blind placebo-controlled trial. Eur Rev Med Pharmacol Sci. 7: 151-9.
Ghosh, A. K. et al., "E-Secretase as a Therapeutic Target for Inhibitor Drugs" Current Medicinal Chemistry, 2002, vol. 9, pp. 1135-1144.
Ghosh, A. K. et al., "Structure-Based Design: Potent Inhibitors of Human Brain Memapsin 2 (β-Secretase)" J. Med Chem, 2001, vol. 44, No. 18, pp. 2865-2868.
Gilman S, et al AN1792(QS-21)-201 Study Team. (2005). Clinical effects of Abeta immunization (AN1792) in patients with AD in an interrupted trial. Neurology 64: 1553-62.
Goedert, M. et al., Alpha-synuclein and neurodegenerative diseases, Nat Rev Neurosci, 2001, vol. 2, pp. 492-501.
Golde, T.E. Alzheimer disease therapy: Can the amyloid cascade be halted? *J. Clin. Invest.* 111, 11-18, 2003.
Goodman et al. "Perspectives in Peptide Chemistry" pp. 283-294 (1981).
Gordon, D.J. et al "Inhibition of Beta Amyloid(4) fibrillogenesis and Disssembly of Beta-Amyloid(4) fibrilsby short Beta-amyloid congeners containinedn-methyl amino acids at alternate residues" Biochemistry 2001 40 8237-8245.
Graf, E, et al "Effects of phytate on mineral bioavailability in mice" Journal of Nutrition 114(7) 1192-1198.
Grases, F. et al "Influence of concomitant food intake on the excretion of orally administered myo-inositol hexaphosphate in humans" J Med Food 9 (1) 2006 72-76.

Grases, fF. et al "intracellular and extracellular myo-inositol hexakisphosphate (InsP6) from rats to humans" Anticancer Res. May-Jun. 2005 25 (3c) 2593-2597.
Greiner Declaration of Oct. 12, 2007 from U.S. Appl. No. 10/787,621, filed Feb. 27, 2003.
Greiner, R, et al "Pathway of Dephosphorylation of myo-inositol hexakisphosphate by phytases of legume seeds" J. Agric. Food Chem. 2002 50 6865-6870.
Greiner, R., et al "Myo-inositol phosphate isomers generated by the action of a phytase from a Malaysian waste-water bacterium" Protein J. 2007.
Greiner, R., et al "myo-inositol phosphate isomers generated by the action of a phytate-degrading enzyme from Klebsiella terrigena on phytate" Can J. Microbiol 52 759-768 (2006).
Greiner, R., et al Pathway of phytate dephosphorylation by B-propeller phytases of different origins Can. J. Microbiol 53 488-495 (2007).
Greiner, R., et al "Stereospecificity of myo-inositol hexakisphosphate dephosphorylation by phytate-degrading enzymes of cereals" J of Food Biochemistry 25 (2001) 229-248.
Greiner, R., et al "Stereospecificity of myo-inositol hexakisphosphate desphosphorylation by a phytate-degrading enzyme of Baker's Yeast" J. Agric. Food Chem 2001 49 2228-2233.
Greiner, R., et al "Stereospecificity of myo-inositol hexakisphosphate desphosphorylation by a phytate-degrading enzyme of *Escherichia coli*" Journal of Biotechnology 84 (2000) 53-62.
Griffith, H.R., et al "Elevated brain scyllo-inositol concentrations in patients with Alzheimer's disease" NMR in Biomedicine Feb. 13, 2007.
Groenen PMW, Merkus HMWM, Sweep CGJ, Wevers RA, Janssen FSM, Steegers-Theunissen RPM. (2003). Kinetics of myo-inositol loading in women of reproductive age. Ann. Clin. Biochem. 40: 79-85.
Guillozet A, et al (2003). Neurofibrillary tangles, amyloid, and memory in aging and mild cognitive impairment. Arch Neurol May 2003; 60: 729-36.
Haass C, et al DJ. (1992). Nature 359: 322-325.
Haccou, P. et al Statistical Analysis of Behavioural Data, p. 120-186, Oxford University Press, Oxford, 1992.
Hager, K. et al, Kinetics and specificity of the renal Na+/myo-inositol cotransporter expressed in Xenopus Oocytes, J. Membr. Biol. Jan. 1995; 143 (2): 103-13.
Hallman M, et al (1986). Respiratory distress and inositol supplementation in preterm infants. Arch Dis Child 61(11): 1076-83.
Hallman M, et al (1987). Inositol supplementation in respiratory distress syndrome: relationship between serum concentration, renal excretion, and lung effluent phospholipids. J Pediatr 110(4): 604-610.
Hallman M, et al (1990). Inositol supplementation in respiratory distress syndrome. Lung 168 Suppl: 877-882.
Hallman M, et al Inositol supplementation in premature infants with respiratory distress syndrome. (1992). N Engl J Med 326(19): 1233-9.
Hallman M, Jarvenpaa AL, Pohjavuori M. (1986). Respiratory distress and inositol supplementation in preterm infants. Arch Dis Child 61(11): 1076-83.
Hallman M, Pohjavuori M, Bry K. (1990). Inositol supplementation in respiratory distress syndrome. Lung 168 Suppl: 877-882.
Hipps, P.P. et al, The identification of myo-inositol:NAD(P) oxidoreductase in mammalian brain. *Biochemical and Biophysical Research Communications*, vol. 68, No. 4, 1976.
Hipps, Paul P. et al (1977). Interconversion of myo- and scyllo-inositol with simultaneous formation of neo-inositol by an NADP dependent epimerase from bovine brain. Biochemical and Biophysical research communications. 1: 340-346.
Hock C, et al (2003). Antibodies against β-amyloid slow cognitive decline in Alzheimer's disease. Neuron 38: 547-554.
Holub BJ. (1986). Metabolism and function of myo-inositol and inositol phospholipids. Ann. Rev. Nutr. 6: 563-597.
Hsaio, K.K. et al., Age-related CNS disorder and early death in transgenic FVB/N mice overexpressing Alzheimer amyloid precursor proteins. *Neuron* 15, 1203-1218 (1995).

(56) References Cited

OTHER PUBLICATIONS

Hsiao, K.K.; et al Correlative memory deficits, Aβ elevation, and amyloid plaques in transgenic mice. Science 274: 99-102; 1996.
Hu, J. et al., "Design and Synthesis of Statine-Containing BACE Inhibitors", Bioorg Med Chem Lett, 2003, vol. 13, No. 24, pp. 4335-4339.
Hu, L. et al The impact of Aβ-plaques on Cortical Cholinergic and Non-cholinergic Presynaptic boutons in Alzheimer's Disease-like Transgenic mice. Neuroscience 121, 421-432 (2003).
Ibanez, P. et al., "Causal relation between α-synuclein gene duplication and familial Parkinson's disease" Lancet, 2004, vol. 364, pp. 1169-1171.
Ibsen, Laura and Strange, Kevin. (1996) In stu localization and osmotic regulation of the Na +-myo-inosytol cotransporter in rat brain. Am. J. Physiol. 271(Renal Fluid Electroclyte Physiol. 40):F877-F885.
Inoue K, et al (1996) Cellular localization of Na+/Myo-inositol co-transporter mRNA in the rat brain. NeuroReport 7:1195-1198.
Intelihealth "Alzheimer's disease" online, accessed Jun. 30, 2008, http://www.intelihealth.com/IH/intlh/WSISW000/8303/9117/195703.HTML?D-DMTHealthAZ.
Irizarry, et al APP$_{Sw}$ transgenic mice develop age-related Aβ deposits and neuropil abnormalities, but no neuronal loss in CA1, J. Neuropathol. Exp. Neurol. 56, 965-973, 1997.
Irving, G.C.J. et al "Inositol phosphate phosphatases of microbiological origin. Some properties of a partially purified bacterial (Pseudomonas) phytase" Aust. J. Biol. Sci 24 547-557 (1971).
Iuorno MJ, et al (2002). Effects of d-chiro-inositol in lean women with the polycystic ovary syndrome. Endocr. Pract. 8(6): 417-423.
Janciauskiene, S. et al., "Alzheimer's peptide and serine proteinase inhibitors in glaucoma and exfoliation syndrome", Documenta Ophthalmologica, 2003, vol. 106, pp. 215-223.
Janus C, et al. (2000). Aβ peptide immunization reduces behavioural impairment and plaques in a model of Alzheimer's disease. Nature 408: 979-982.
Jen, L. S. et al., "Alzheimer's peptide kills cells of retina in vivo" Nature, 1998, vol. 392, pp. 140-141.
Jo, E. et al., "α-Synuclein Membrane Interactions and Lipid Specificity", J Biol Chem, 2000, vol. 275, pp. 34328-34334.
Josien, Hubert, Recent Advances in the development of γ-secretase inhibitors, Current Opinion in Drug Discovery & Development, 2002 5(4):513-525.
Kaiser, Lana G. et al (2005). Scyllo-inositol in normal aging human brain: 1H magnetic resonance spectroscopy study at 4 Tesla. NMR Biomed. 18: 51-55.
Kaplan Z, et al (1996). Inositol treatment of post-traumatic stress disorder. Anxiety 2(1): 51-52.
Katsuno, M. et al., "Transgenic mouse models of spinal and bulbar muscular atrophy (SBMA)" Cytogenetic and Genome Research, 2003, vol. 100, pp. 243-251.
Kayed, R. et al., Common Structure of Soluble amyloid oligomers implies common mechanism of pathogenesis. Science 300, 486-489 (2003).
Kersting et al 2003 Identification of the Inositol Isomers Present in Tetrahymena. J Eukaryot Microbiol 50:164-168.
Kheterpal, I et al,Structural features of the Abeta amyloid fibril elucidated by limited proteolysis. Biochemistry, 2001 40(39):11757.
Kiely, D.E., et al., Cyclization of D-xylo-Hexos-5-ulose, a Chemical Model for the Biosynthesis of myo- and scyllo-Inositols, Communications to the Editor (received Mar. 20, 1968), Journal of the American Chemical Society, 90:12, Jun. 5, 1968.
Kierstead. (2003). Alzheimer's disease: Inositol and Amyloid-Beta Interactions. Alzheimer Society of Canada Research Program. Research Grants and Training Awards.
Kim Ji, et al (2005). Effects of pinitol isolated from soybeans on glycaemic control and cardiovascular risk factors in Korean patients with type II diabetes mellitus: a randomized controlled study. Eur. J. Clin. Nutr. 59: 456-458.

Kimberly, W. T. et al., "g-Secretase is a membrane protein complex comprised of presenilin, nicastrin, aph-1, and pen-2", Proc. Natl Acad. Sci, 2003, vol. 100, pp. 6382-6387.
Kinnard, R. L. et al., "Characterization of scyllo-inositol-containing phosphatidylinositol in plant cells.," Biochem Biophys Res Comm, 2003, vol. 210, pp. 549-555.
Kirkitadze, M.D. etal., Paradigms shifts in Alzheimer's disease and other neurodegenerative disorders: the emerging role of oligomeric assemblies. J. Neurosci. Res. 69, 567-577 (2002).
Klein, William L. (2002). Aβ toxicity in Alzheimer's disease: globular oligomers (ADDLs) as new vaccine and drug targets. Neurochemistry International. 41: 345-352.
Kofman, O. et al. The effect of peripheral inositol injection on rat motor activity models of depression, lsr. J. Med. Sci. 29, 580-586, 1993.
Kofman, Ora et al. (1998). Chronic dietary inositol enhances locomotor ctivity and brain inositol levels in rats. Psychopharmacology 139: 239-242.
Koppaka, V et al Accelerated accumulation of amyloid beta proteins on oxidatively damaged lipid membranes. Biochemistry 39, 10011-10016 (2000).
Kruger, R. et al., "Ala30Pro mutation in the gene encoding alpha-synuclein in Parkinson's disease", Nat Genet, 1998, vol. 18, No. 2, pp. 106-108.
Lambert, M.P. etal., Diffusible, non-fibrillar ligands derived from Abeta1-42 are potent central nervous system neurotoxins. Proc. Natl. Acad. Scie USA 95, 6448-6453 (1998).
Lanz T, et al (2003). Studies of Aβ pharmacodynamics in the brain, cerebrospinal fluid, and plasma in young (plaque-free) Tg2576 mice using the γ-secretase inhibitor. JPET 309: 49-55.
Lamer, J. et al, Inositol dehydrogenase from Aerobacter aerogenes, Archives of Biochemistry and Biophysics, vol. 60, pp. 352-363 (1956).
Lee, H. J. et al., "Beta-Secretase (BACA1) Inhibitors from Sanguisorbae Radix", Arch Pharm Res, 2005, vol. 28, No. 7, pp. 799-803.
Leissring, M.A. et al., Enhanced proteolysis of β-amyloid in APP transgenic mice prevents plaque formation, secondary pathology and premature death. Neuron 40, 1087-1093 (2003).
Levine J, et al (1993). Inositol 6 g daily may be effective in depression but not in schizophrenia. Hum. Psychopharmacol. 8(1): 49-53.
Levine J, et al (1993). Inositol treatment raises CSF inositol levels. Brain Research 627: 168-170.
Levine J, et al (1994). CSF inositol in schizophrenia and high dose inositol treatment of schizophrenia. Eur Neuropsychopharmacol. 4: 487-490.
Levine J, et al (1994). The effect of inositol on cognitive processes and mood states in normal volunteers. Eur. N-Psychopharmacol. 4(3): 417.
Levine J, et al (1995). Double-blind, controlled trial of inositol treatment of depression. The Am. J. Psych. 152(5) 792-794.
Levine J, et al (1996a). Inositol may worsen attention deficit disorder with hyperactivity. Hum. Psychopharmacol. 10: 481-484.
Levine J, et al (1996b). Lack of effect of 6 gm inositol treatment on post-ECT cognitive function in humans. J. Psychiatr. Res. 29: 487-489.
Levine J, et al (1997). Inositol treatment of autism. J. Neural. Transm. 104(2-3): 307-310.
Levine J, et al (1999). Combination of inositol and serotonin reuptake inhibitors in the treatment of depression. Biol. Psychiatry 45(3): 270-3.
Levine J, Goldberger I, Rapaport A, Schwartz M, Schields C, Elizur A, Belmaker RH, Shapiro J, Agam A. (1994). CSF inositol in schizophrenia and high dose inositol treatment of schizophrenia. Eur Neuropsychopharmacol. 4: 487-490.
Levine, "Controlled trials of inositol in psychiatry," European Neuropsychopharmacology, 1997, vol. 7, pp. 147-155.
Levine, J. Controlled trails of inositol in psychiatry, European Neuropsychopharmacology 7, 147-155, 1997.
Li, Peter P. et al. vitro and ex vivo effects of antidepressants on Rat Brain Membrane-Bound Phosphatidylinositol Synthetase Activity. Neurochemical Research, 13, 8, 1988, pp. 789-795.

(56) References Cited

OTHER PUBLICATIONS

Li, R. et al., "Amyloid β peptide load is correlated with increased β-secretase activity in sporadic Alzheimer's disease patients", Proc. Natl. Acad. Sci. USA, 2004, vol. 101, No. 10, pp. 3632-3637.

Lim, G. P. et al., "The Curry Spice Curcumin Reduces Oxidative Damage and Amyloid Pathology in an Alzheimer Transgenic Mouse", J Neurosci, 2001, vol. 21, No. 21, pp. 8370-8377.

Lim, P.E., et al "The phytases. II. Properties of phytase fractions F1 and F2 from wheat bran and the myo-inositol phosphates produced by fraction F2" Biochim. Biophys. Acta 302 316-328 (1973).

Lombardo, J.A., et al., Amyloid-beta antibody treatment leads to rapid normalization of plaque-induced neuritic alterations. *J Neurosci.* 23, 10879-10883 (2003).

Lubrich B, et al (2000). Differential expression, activity and regulation of the sodium/myo-inositol cotransporter in astrocyte cultures from different regions of the rat brain. Neuropharmacol. 39(4): 680-690.

Luibl, V. et al., "Drusen deposits associated with aging and age-related macular degeneration contain nonfibrillar amyloid oligomers", J Clin Invest, 2006, vol. 116, No. 2, pp. 378-385.

Magasanik, B. et al., The stereochemistry of an enzymatic reaction: the oxidation of l-, d-, and epi-inositol by acetobacter suboxydans, *Journal of Biological Chemistry*, pp. 173-188; 1947.

Markesbery WR. The role of oxidative stress in Alzheimer's disease. (1999). Arch Neurol 56: 1449-52.

Marty, M. A. et al., Air Toxics Hot Spots Program Risk Assessment Guidelines, Part IV, Final Draft, of Five of Environmental Protection Agency, California Environmental Protection Agency, 2000.

Masliah E, et al (2005). Aβ vaccination effects on plaque pathology in the absence of encephalitis in Alzheimer disease. Neurology 64(1): 129-131.

Mayeux,b et al. Plasma amyloid β-peptide 1-42 and incipient Alzheimer's disease, Ann. Neurol., 46, 412-416, 2001.

McAdam, B. F. et al., "Systemic biosynthesis of prostacyclin by cyclooxygenase (COX)-2: The human pharmacology of a sensitive inhibitor of COX-2," Pharmacology, Jan. 1999, vol. 96, pp. 272-277.

McAdam, K. P. W. J. et al., "Association of amyloidosis with erythema nodosum leprosum reactions and recurrent neutrophil leucocytosis in leprosy", Lancet, 1975, vol. 306, pp. 572-573.

McGeer PL, et al (2002). Local neuroinflammation and the progression of Alzheimer's disease. Journal of NeuroVirology 8: 529-538.

McGowan E, Pickford F, Kim J, Onstead L, Eriksen J, Yu C, Skipper L, Murphy MP, Beard J, Das P, Jansen K, DeLucia M, Lin W, Dolios G, Wang R, Eckman CB, Dickson DW, Hutton M, Hardy J, Golde T. (2005). Neuron 47: 191-199.

Mckhann, G. et al., "Clinical diagnosis of Alzheimer's disease: Report of the NINCDS-ADRDA Work Group under the auspices of Department of Health and Human Services Task Force on Alzheimer's Disease", Neurology, 1984, vol. 34, pp. 939-944.

McLaurin Declaration of Aug. 15, 2006 from U.S. Appl. No. 10/787,621, filed Feb. 27, 2003.

McLaurin J, et al (2000). Inositol stereoisomers stabilize an oligomeric aggregate of Alzheimer amyloid β peptide and inhibit a β-induced toxicity. J. Biol. Chem. 275(24): 18495-18502.

McLaurin, J, et al. Phosphatidylinositol and inositol involvement in Alzheimer amyloid-β fibril growth and arrest, J. Mol. Biol. 278, 183-194, 1998.

McLaurin, J, et al. Review: Modulating Factors in Amyloid-β Fibril formation, Journal of Structural Biology, vol. 103, pp. 259-270, 2000.

McLaurin, J, et al. Therapeutically effective antibodies against amyloid β peptide target amyloid-β residues 4-10 and inhibit cytotoxicity and fibrillogenesis, Nature Medicine 8, 1263-1269, 2002.

McLaurin, J. et al A. Membrane disruption by Alzheimer beta-amyloid peptides mediated through specific binding to either phospholipids or gangliosides. Implications for neurotoxicity. *J. Biol. Chem.* 271, 26482-26489 (1996).

McLaurin, J. et al "Cyclohexanol inhibitors of Abeta aggregation prevent and reverse Alzheimer phenotype in mouse model" Nature Medicine Jul. 2006 12(7) 801-808.

McLaurin, J. et al A. Characterization of the interactions of Alzheimer beta-amyloid peptides with phospholipid membranes. *Eur. J. Biochem.* 245, 355-363 (1997).

McLaurin, J. et al., "Inositol stereoisomers stabilize an oligomeric aggregate of Alzheimer amyloid β peptide and inhibit Aβ-induced toxicity," The Journal of Biological Chemistry, Jun. 16, 2000, pp. 18495-18502, vol. 275, No. 24.

McLaurin, J. et al., "Review: Modulating Factors in Amyloid-Beta Fibril Formation," Journal of Structural Biology, 2000, pp. 259-270, vol. 130.

McLean, C.A. etal., Soluble pool of Abeta amyloid as a determinant of severity of neurodegeneration in Alzheimer's disease. *Ann Neurol.* 46, 860-866 (1999).

McPhee, et al "Studies of inositol analogues as inhibitors of the phosphoinositide pathway, and incorporation of 2-deoxy-2-fluoro-myo-inositol to give analogues of phosphatidylinositor intermediates" Biochem J. 1991 277 407-412.

Metaxas, N. E. "Familial Mediterranean fever and amyloidosis", Kidney Int., 1981, vol. 20, pp. 676-685.

Meyerhoff D, et al (1996) Elevated scyllo-inositol in adult human brain. In: Proc ISMRM, 4$^{th}$ Scientific Meeting, New York, pp. 954.

Michaelis, Thomas et al. (1993). Identification of Scyllo-Inositol in Proton NMR Spectra of Human Brain In Vivo. NMR in Biomedicine, vol. 6, 105-109.

Mizuno, T. et al., Cholesterol-dependent generation of a seeding amyloid beta-protein in cell culture. *J. Biol. Chem.* 274, 15110-15114 (1999).

Moats, Rex A. et al (1994). Abnormal Cerebral Metabolite Concentrations in Patients with Probable Alzheimer Disease. MRM. 32: 110-115.

Moechars D., etal., Early Phenotypic Changes in Transgenic Mice That Overexpress Different Mutants of Amyloid Precursor Protein in Brain *J. Biol. Chem.*, 274, 6483-6492 (1999).

Mohs, R. C. et al., "The Alzheimer's Disease Assessment Scale", Int Psychogeriatr, 1996, vol. 8, No. 2, pp. 195-203.

Moore, Constance M. et al. (1999). Effects of myo-Inositol Ingestion on human Brain myo-Inositol Levels: A Proton Magnetic Resonance Spectroscopic Imaging Study. Biol Psychiatry. 45: 1197-1202.

Morgan D, Diamond DM, Gottschall PE, Ugen KE, Dickey C, Hardy J, Duff K, Jantzen P, DiCarlo G, Wilcock D, Connor K, Hatcher J, Hope C, Gordon M, Arendash G. (2000). A β peptide vaccination prevents memory loss in an animal model of Alzheimer's disease. Nature 408: 982-985.

Morgan, B. A. and Gainor, J. A. (1989) Ann. Rep. Med. Chem. 24:243.

Morris, R. Development of a water-maze procedure for studying spatial learning in the rat. *J. Neurosci Methods* 11, 47-60 (1984).

Mount, H.T.J., Progressive sensorimotor impairment is not associated with reduced dopamine and high energy phosphate donors in a model of ataxia-telangiectasia. *J Neurochem* 88:1449-1454.

Moyer JR Jr, et al Methods for whole-cell recording from visually preselected neurons of perirhinal cortex in brain slices from young and aging rats. *J Neurosci Methods*.86, 35-54 (1998).

Murthy, P. P. N. et al., "Evidence of two isomers of phosphatidylinositol in plant tissue", Plant Physiol, 1992, vol. 98, pp. 1498-1501.

Nakano, T. et al "the pathway of dephosphorylation of myo-inositol hexaisphosphate by phytases from wheat bran of *Triticum aestivum* L. cv. Nourin #61" Biosci Biotechnol Biochem 64(5) 995-1003 (2000).

Narumi, Koyu et al. (1969). Gaschromatographic Analysis of Free myo- and scyllo-Inositols in Animal Tissues. Japan. J. Exp. Med. 39:399-407.

Naslund, J. et al., "Correlation between elevated levels of amyloid β-peptide in the brain and cognitive decline", JAMA, 2000, vol. 283, pp. 1571-1577.

Nemets B, Mishory A, Levine J, Belmaker RH. (1999). Inositol addition does not improve depression in SSRI treatment failures. J. Neural. Transm. 106: 795-798.

(56) References Cited

OTHER PUBLICATIONS

Nemets B, Talesnick B, Belmaker RH, Levine J. (2002). Myo-inositol has no beneficial effect on premenstrual dysphoric disorder. World J. Biol. Psychiatry. 3(3): 147-149.
Nestler JE, Jakubowicz DJ, Reamer P, Gunn RD, Allan G. (1999). Ovulatory and metabolic effects of D-chiro-inositol in the polycystic ovary syndrome. N. Engl. J. Med. 340(17): 1314-20.
Nicoll JAR, et al (2003). Neuropathology of human Alzheimer disease after immunization with amyloid-β peptide: a case report. Nature Medicine 9(4): 448-452.
O'Hare, E., et al (1996) Utilization of an operant model of food reinforced behavior involving neuropeptide Y, insulin, 2-deoxy-d-glucose, and naloxone. Behavioral Pharmacology, 7: 742-753.
Ohno M, et al (2004). BACE1 Deficiency rescues memory deficits and cholinergic dysfunction in a mouse model of Alzheimer's disease. Neuron 41: 27-33.
Orgogozo JM, et al (2003). Subacute meningoencephalitis in a subset of patients with AD after Aβ42 immunization. Neurology 61(1): 46-54.
Pak, Y. et al., "In vivo conversion of [$^3$H]myoinositol to [$^3$H]chiroinositol in rat tissues", J Biol Chem, 1992, vol. 267, pp. 16904-16910.
Palatnik A, et al (2001). Double-blind, controlled, crossover trial of inositol versus fluvoxamine for the treatment of panic disorder. J. Clin. Psychopharmacol. 21(3): 335-339.
Patani, G. A. et al., "Bioisosterism: A rational approach in drug design" Chemical Reviews, 1996, vol. 96, No. 8, pp. 3147-3176.
Patey, S. J. et al., "Novel heparan sulphate analogues: inhibition of beta-secretase cleavage of amyloid precursor protein", Biochem Soc Trans, 2005, vol. 33, No. 5, pp. 1116-1118.
Patishi, Yardena et al. (1996). Differential uptake of myo-inositol in vivo into rat brain areas. European Neuropsychopharmacology. 6: 73-75.
Paulson, H. et al., "Polyglutamine disease and neuronal cell death," PNAS, 2000, vol. 97, No. 24, pp. 15957-12958.
Phinney, A. et al., No hippocampal neuron or synaptic bouton loss in learning-impaired aged β-amyloid precursor protein-null mice. *Neuroscience* 90, 1207-1216 (1999).
Phinney, A.L, et al., In vivo reduction of amyloid-beta by a mutant copper transporter. *Proc Natl Acad Sci U S A*. 100, 14193-14198 (2003).
Plimmer, Robert H.S., et al. V. The hydrolysis of organic phosphorus compounds by dilute acid and by dilute alkali. *Ludwig Mond Research Laboratory for Biological Chemistry*, Institute of Physiology, University College, London, Nov. 23, 1912, pp. 72-80.
Proceedings 2002 II of 81$^{st}$ Spring Meeting of the Chemical Society of Japan, 2002, 1418, 2 pages.
Ramaley, Robert. Purification and Properties of *Bacillus subtilis* inositol dehydrogenase, *Journal of Biological Chemistry*, vol. 254, No. 16, 1979, pp. 7684-7690.
Reber,G. et al., myo-Inositol transport system in *Pseudomonas putida, Journal of Bacteriology*, Sep. 1977, p. 872-875, vol. 131, No. 3.
Redwine, J. M. et al., "Dentate gyrus volume is reduced before onset of plaque formation in PDAPP mice: A magnetic resonance microscopy and stereologic analysis" PNAS, 2003, vol. 100, No. 3, pp. 1381-1386.
Reiner, A. et al., "Differential loss of striatal projection neurons in Huntington disease", Proc. Natl Acad. Sci, 1988, vol. 85, pp. 5733-5737.
Reixach, N. et al., "Inhibition of β-amyloid-induced neurotoxicity by imidazopyridoindoles derived from a synthetic combinatorial library", Journal of Structural Biology, 2000, vol. 130, pp. 247-258.
Response to Communication dated Mar. 23, 2011 dated Oct. 20, 2011.
Response to Extended European Search Report dated Apr. 29, 2009, dated Jul. 28, 2009.
Richards, M.H. et al. Epi-inositol is biochemically active in reversing lithium effects on cytidine monophosphorylphosphatidate (CMP-PA), J. Neural Transm 103, 1281-1285, 1996.

Richardson, R.L., et al (2002) Behavioral and histopathological analyses of ibuprofen treatment on the effect of aggregated Aβ1-42 injections in the rat. Brain Research, 954: 1-10.
Riley, et al "scyllo-inositol Pentakisphosphate as an analogue of myo-inositol 1,3,4,5,6-pentakisphosphate: chemical sythesis, physicochemistry and biological applications" Chembiochem 2006 7 1114-1122.
Rogers J, et al (1992). Complement activation by β-amyloid in Alzhimer's disease. Proc. Natl. Acad. Sci. USA 89: 10016-10020.
Rojo, I. et al., "Macrocyclic peptidomimetic inhibitors of b-secretase (BACE): First X-ray structure of a macrocyclic peptidomimetic-BACE complex", Bioorg Med Chem Lett, 2006, vol. 16, No. 1, pp. 191-195.
Ryals, P. E. et al., "Sodium-dependent uptake of [3H]scyllo-inositol by Tetrahymena: Incorporation into phosphatidylinositol, phosphatidylinositol-linked glycans, and polyphosphoinositols", Arch Biochem Biophys, 1999, vol. 366, No. 2, pp. 261-266.
Saddichha, S. et al., "Alzheimer's and non-Alzheimer's dementia: A critical review of pharmacological and nonpharmacological strategies", American Journal of Alzheimer's Disease and Other Dementias, 2008, vol. 23, No. 2, pp. 150-161.
Sarvey JM, et al Long-term potentiation: studies in the hippocampal slice. *J Neurosci Methods* 28,109-124 (1989).
Schenk D, et al (1999). Immunization with amyloid-beta attenuates Alzheimer-disease-like pathology in the PDAPP mouse. Nature 400: 173-177.
Schott JM, et al (2005). Measuring atrophy in Alzheimer disease: A serial MRI study over 6 and 12 months. Neurology 65: 119-124.
Scott H, et al (2002). Aberrant expression of the glutamate transporter excitory amino acid transporter 1 (EAAT1) in Alzheimer's disease. J Neurosci 22: RC206.
Seaquist, E et al (1998). Identification of a High Concentration of Scyllo-Inositol in the Brain of a Healthy Human Subject Using 1H- and 13C-NMR. MRM. 39: 313-316.
Seedat S, et al (1999). Inositol augmentation of serotonin reuptake inhibitors in treatment-refractory obsessive disorder: an open trial. Int. Clin. Psychopharmacol. 15(4): 244.
Selkoe DJ, (2002). Alzheimer's disease is a synaptic failure. Science 298: 789-791.
Selkoe DJ. (2001). Alzheimer's disease: genes proteins, and Therapy. Physiol Rev 81: 741-766.
Selkoe, D.J. Deciphering the genesis and fate of amyloid beta-protein yields novel therapies for Alzheimer disease. *J. Clin Invest.* 110, 1375-1381 (2002).
Shamsuddin, AM "Metabolism and cellular functions of IP6:a review" Anticancer Res. Sep.-Oct. 1999; 19 (5A) :3733-6.
Shapiro, J. et al (2000). Scyllo-Inositol in post-mortem brain of bipolar, unipolar and schizophrenic. J Neural Transm. 107: 603-607.
Sharma, K. et al., "Complex-1 activity and 18F-DOPA uptake in genetically engineered mouse model of Parkinson's disease and the neuroprotective role of coenzyme Q10", Brain Res Bull., 2006, vol. 70, No. 1, pp. 22-32.
Sherman, William R. et al. (1968). The Identification of myo-inosose-2 and scyllo-inositol in mammalian tissues. Biochemistry 7, # 2, 819-824.
Sherman, William R. et al. (1968). The measurement of myo-inositol, myo-inosose-2 and scyllo-inositol in mammalian tissues. Biochim. Biophys. Acta. 158: 197-205.
Shetty, H. et al (1996). Brain accumulation of myo-inositol in the trisomy 16 mouse, an animal model of Down's Syndrome. Biochem. J. 313: 31-33.
Shetty, H. et al (1996). Cerebrospinal fluid and plasma distribution of myo-inositol and other polyols in Alzheimer disease. Clinical Chemistry 42:2, 298-302.
Shetty, H. U. et al., "Capillary Gas Chromatography Combined with Ion Trap Detection for Quantitative Profiling of Polyols in Cerebrospinal Fluid and Plasma", Anal. Biochem., 1995, vol. 224, pp. 279-285.
Shetty, H.U. et al. Assay of myo-inositol in cerebrospinal fluid and plasma by chemical ionization mass spectrometry of the hexaacetate derivative. Biol. Mass Spec. 23, 440-444, 1994.

(56) References Cited

OTHER PUBLICATIONS

Silbernagl S, et al (2003). Tubular reabsorption of myo-inositol vs. that of D-glucose in rat kidney in vivo et situ. Am. J. Physiol. Renal Physiol. 284: F1181-F1189.
Sinha, S. et al., "Cellular mechanisms of b-amyloid production and secretion" Proc. Natl. Acad. Sci, 1999, vol. 96, pp. 11049-11053.
Sinha, S. et al., "Purification and cloning of amyloid precursor protein β-secretase from human brain", Nature, 1999, vol. 402, pp. 537-540.
Slon-Usakiewicz J.J. et al, Clin. Proteom. J. 2004, 1:227-234.
Spector R. (1978) The transport and metabolism of scyllo-inositol in the central nervous system. J. Neurochem. 31: 1113-5.
Spector, R. Myo-inositol transport through the blood-brain barrier. *Neurochemical Research* 13, 785-787 (1988).
Spillantini, M. G. et al., "Assignment of human alpha-synuclein (SNCA) and beta-synuclein (SNCB) genes to chromosomes 4q21 and 5q35", Genomics, 1995, vol. 27, No. 2, pp. 379-381.
Spillantini, M. G. et al., "α-Synuclein in Lewy bodies", Nature, 1997, vol. 388, pp. 839-840.
Stanton PK, et al Norepinephrine regulates long-term potentiation of both the population spike and dendritic EPSP in hippocampal dentate gyrus. *Brain Res Bull.* 18, 115-119 (1987).
Strange, Kevin et al. (1994). Osmoregulatory Changes in Myo-Inositol Content and Na+/Myo-Inositol Cotransport in Rat Cortical Astrocytes. GLLA 12: 35-43.
Tainer JA et al, Nature. Nov. 17-23, 1983; 306(5940):284-7.
Tanaka, M. et al., Trehalose alleviates polyglutamine-mediated pathology in a mouse model of Huntington disease. *Nat. Med.* 10, 148-154 (2004).
Townsend, M. et al "Orally available compound prevents deficits in memory caused by the Alzheimer Amyloid-Beta oligomer" Annals of Neurology 2006 60(6) 668-676.
Uldry M, et al (2001). Identification of a H+-myo-inositol symporter expressed predominantly in the brain. EMBO J. 20: 4467-4477.
Uldry, M. et al The SLC2 family of facilitated hexose and polyol transporters. *Pflugers Acta*, 447, 480-489 (2004).
Uldry, Marc et al. (2004). Regulated exocytosis of an H+/myo-inositol symporter at synapses and growth cones. The EMBO Journal. 23:531-540.
Ulmer, T. S. et al., "Comparison of Structure and Dynamics of Micelle-bound Human-Synuclein and Parkinson Disease Variants", Journal of Biological Chemistry, 2005, vol. 280, No. 52, pp. 43179-43187.
U.S. Appl. No. 12/090,130, filed Oct. 16, 2008, to Cruz, et al.
U.S. Appl. No. 12/125,498, filed Mar. 22, 2008, to McLaurin.
U.S. Appl. No. 12/282,030, filed Sep. 8, 2008, to Cruz, et al.
U.S. Appl. No. 12/301,155, filed Nov. 11, 2008, to Slon-Usakiewicz.
U.S. Appl. No. 12/396,515, filed Mar. 3, 2009, to McLaurin.
U.S. Appl. No. 12/438,572, filed Feb. 24, 2009, to Cruz, et al.
U.S. Appl. No. 12/445,164, filed Apr. 20, 2009, to Cruz.
Vadnal et al. (1998) Promising Psychotherapeutic Effects of the Natural Sugar: Myo-Inositol. Nutritional Neuroscience. vol. 1. 21-33.
van Calker, D, et al (2000). The high affinity inositol transport system—implications for the pathophysiology and treatment of bipolar disorder. Bipolar Disorders 2: 102-107.
Varano, F. et al., "Synthesis and Biological Evaluation of a New Set of Pyrazolo[1,5-c]quinazoline-2-carboxylates as Novel Excitatory Amino Acids Antagonists," J. Med. Chem., 2002, vol. 45, pp. 1035-1044.
Vaucher, E. et al., Object Recognition Memory and Cholinergic Parameters in Mice Expressing Human Presenilin 1 Transgenes. *Exp. Neurol.* 175, 398-406 (2002).
Viola, A. et al., "High Cerebral scyllo-inositol: a new marker of brain metabolism disturbances induced by chronic alcoholism," Magnetic Resonance Materials in Physics, Biology and Medicine, 2004, vol. 17, No. 1, pp. 47-61.
Vogl, O., et al. Synthesis of Hexaoxadiamantanes, *The Journal of Organic Chemistry*, vol. 34, No. 1, 1969.

Walsh DM, et al (2000). The oligomerization of amyloid β intracellularly in cells derived from human brain. Biochemistry 39: 10831-10839.
Walsh DM, et al (2002). Amyloid β-oligomers: their production, toxicity and therapeutic inhibition. Biochem. Soc. Trans. 30: 552-557.
Walsh DM, et al (2005). Certain inhibitors of synthetic amyloid β-peptide (A β) fibrillogenesis block oligomerization of natural A β and thereby rescue long-term potentiation. J Neurosci. 25: 2455-2462.
Walsh DM, et al DJ. (2002). Naturally-secreted oligomers of amyloid-β protein potently inhibit hippocampal long-term potentiation in vivo. Nature 416: 535-539.
Walsh, D. T. et al., "Amyloid-Beta Peptide Is Toxic to Neurons In Vivo via Indirect Mechanisms", Neurobiol Dis, 2002, vol. 10, pp. 20-27.
Wang HW, et al. (2002). Soluble oligomers of β-amyloid (1-42) inhibit long-term potentiation but not long-term depression in rat dentate gyrus. Brain Res. 924: 133-140.
Wang Q, et al (2004). Block of LTP by naturally secreted and synthetic amyloid β peptide in hippocampal slices is mediated via activation of the kinases C-Jun N-terminal kinase, cyclin-dependent kinase 5, and p38 mitogen-activated protein kinase as well as MGR type 5. J. Neurosci. 24(13): 3370-3378.
Wang, J. et al., "The levels of soluble versus insoluble brain Aβ distinguish Alzheimer's disease from normal and pathological aging", Exp. Neurol., 1999, vol. 158, pp. 328-337.
Weggen S, et al A subset of NSAIDs lower amyloidogenic Ab42 independently of cyclooxygenase activity Nature 2001 414(6860) 212-216.
Wentzel, Parri et al. (2001). Induction of Embryonic Dysmorphogenesis by High Glucose Concentration, Disturbed Inositol Metabolizm, and Inhibited Protein Kinase C Activity. Teratology 63: 193-201.
Wiltfang, J. et al., Highly conserved and disease-specific patterns of carboxyterminally truncated Abeta peptides 1-37/38/39 in addition to 1-40/42 in Alzheimer's disease and in patients with chronic neuroinflammation *J Neurochem* 81, 481-496 (2002).
Wong, P.C., et al Genetically engineered mouse models of neurodegenerative diseases. *Nat. Neurosci.* 5, 633-639 (2002).
Wyss, M. et al., "Biochemical Characterization of Fungal Phytases (myo-Inositol Hexakisphosphate Phosphohydrolases): Catalytic Properties," Applied and Enviromental Microbiology, Feb. 1999, pp. 367-373.
Xun, Z. et al., "Protein expression in a *Drosophila* model of Parkinson's disease" J Proteome Res, 2007, vol. 6, No. 1, pp. 348-357.
Yamashita, T et al. (1998). Regulation of Na+/myo-inositol cotrasporter gene expression in hyperglycaemic rat hippocampus. Molecular Brain Research 57: 167-172.
Yanagisawa, K. et al., GM1 ganglioside-bound amyloid beta-protein (A beta): a possible form of preamyloid in Alzheimer's disease. *Nat. Med.* 1, 1062-1066 (1995).
Yang, F. et al., "Curcumin Inhibits Formation of Amyloid β Oligomers and Fibrils, Binds Plaques, and Reduces Amyloid in Vivo" J Biol Chem, 2005, vol. 280, No. 7, pp. 5892-5901.
Ye, M. et al., "Transplantation of bone marrow stromal cells containing the neurturin gene in rat model of Parkinson's disease", Brain Res, 2007, vol. 1142, pp. 206-216.
Yoshihda K., et al., Cloning and nucleotide sequencing of a 15kb region of the *Bacillus subtilis* genome containing the iol operon. *Microbiology*, (1994) 140, 2289-2298.
Zarranz, J. et al., "The New Mutation, E46K, of α-Synuclein Causes Parkinson and Lewy Body Dementia", Ann Neurol, 2004, vol. 55, pp. 164-173.
Zhang, et al "Rapid determination of the Binding Affinity and Specificity of the Mushroom Polporus squamosus Lectin Using Frontal Affinity Chromatography Coupled with Electrospray mass spectromerty" Glycoiology 2001 11(2) 141-147.
Zhang, X. et al., "A potent small molecule inhibits polyglutamine aggregation in Huntington's disease neurons and suppresses neurodegeneration in vivo" PNAS, 2005, vol. 102, No. 3, pp. 892-897.

(56) References Cited

OTHER PUBLICATIONS

Ball. J. B. and Alewood, P. F., "Conformation Constraints: Nonpeptide B-Turn Mimics," J Mol. Recognition 3(2):55-64, 1990.
Bonnet, et al., "Casual Relation between a-synuclein gene duplication and famalial parkinson's disease," Lancet 364: 1169-1171, 2004.
Bouveault, L., et al., "De l'isomerie optique dans les corps a chaines fermees," La Societe Chimique. {aros. 1894: 11: 144-147.
Bruening W, et al., "Up-regulation of protein chaperones preserves viability of cells expressing toxic Cu/Zn-superoxide dismutase mutants associated with amyotrophic lateral sclerosis, " J Neurochem. 72:693-699, 1999.
Bruijn, L., et al., "Aggregation and Motor Neuron Toxicity of an ALS-Linked SOD1 Mutant lndpendent from Wild-Type SOD1," Science 281, 1851-1854, 1998.
Cedarbaum J et al., "Population Pharmacokinetic Analysis of Plasma, Cerebrospinal Fluid, and Brain ELND005 in Patients with Mild to Moderate Alzheimer's Disease", International Conference on Alzheimer's Disease (ICAD) meeting, to be held Jul. 16-21, 2011, Paris, Poster Presentation # P2-509, Jul. 18, 2011.
Chiu, A.Y., et al., "Age-Dependent Penetrance of Disease in a Transgenic Mouse Model of Familial Amyotrophic Lateral Sclerosis," Mol. Cell Neurosci. 6, 349-362, 1995.
Clement AM., et al., "Wild-Type Nonneuronal Cells Extend Survival of SOD1 Mutant Motor Neurons in ALS Mice," Science 302: 113-117, 2003.
Culotta, V.C., et al., "The Copper Chaperone for Superoxide Dismutase","The Journal of Biological Chemistry," vol. 272, No. 38, 1997, pp. 23469-23472.
Doraiswamy PM, "Non-cholinergic strategies for treating and preventing Alzheimer's disease", (2002) CNS Drugs 16(12): 811-824.
"Elan and Transition Therapeutics Announce Modifications to ELND005 Phase II Clinical Trials in Alzheimer's Disease" Elan Press Release, Dec. 15, 2009.
"Elan and Transition Therapeutics Announce Phase 1 Data Showing ELND005 Achieves Desired Concentrations in Brain Tissue and Cerebrospinal Fluid," Elan Corporation Press Release of Jul. 13, 2009.
Elan and Transition Therapeutics Announce Topline Summary Results of Phase 2 and Plans for Phase 3 for ELND005 (Scyllo-Inositol), Elan Press Release Aug. 9, 2010.
Furukawa Y, et al., "Amyotrophic Lateral Sclerosis Mutations Have the Greatest Destabilizing Effect on the Apo-and Reduced Form of SOD1, leading to Unfolding and Oxidative Aggregation." J Biol Chem. 280(17): 17266-17274, 2005.
Hirschman, R., et al., "The Identification of Myo-Inositol: NAD(P)+Oxidoreductase in Mammalian Brain," J. Am. Chem. Soc. 115:12550-12568, 1993.
Iuorno, M.J., et al., "Effects of d-chiro-inositol in lean women with the polycystic ovary syndrome," Endocr. Pract. 8(6), 417-423 (2002).
James, G. L. et al., "Benzodiazepine Peptidomimetics: Potent Inhibitors of RasFarnesylation in Animal Cells," Science 260:1937-1942, 1993.
Jo, E., et al., "α-Synuclein-synaptosomal membrane interactions. Implications for fibrillogenesis," European Journal of Biochemistry 271:3180. 2004.
Jog, et al., "Alkaline phytase from lily pollen: Investigation of biochemical properties," Archives of Biochemistry and Biophysics. 440:133-140, 2005.
Kamei et al., "An ultrastructural and histochemical study of alveolar soft part sarcoma with special reference to the nature of crystals," Acta Path Jpn 32 123-133, 1982.

Kato, S. et al., "New consensus research on neurophathological aspects of familial amyotrophic lateral sclerosis with superoxide dismutase 1 (SOD1) gene mutations: Inclusions containing SOD1 in neurons and astrocytes," AmyotrophLaterlScelerosis & Other Motor Neuron Disorders, 1:3, 163-184, 2000.
Khaw et al., "Towards better treatment of glaucoma", BMJ 320:1619, 2000.
Khaw, P.T., et al., "ABC of Eyes—Glaucoma-2: Treatment," BMJ vol. 328 (Jan. 17, 2004), pp. 156-158.
Kim, Y.J., et al., "Unsaturated Fatty Acids Induced Cytotoxic Aggregate formation of Amyotrophic Lateral Sclerosis-linked Superoxide Dismutase 1 Mutants," J. Biol Chem. 280(22):21515-21521, 2005.
Malek, G., et al., "Apolipoprotein E allele-dependent pathogenesis: A model for age-related retinal degeneration," ProcNatlAcadSci USA 102(33): 11900-5 (2005).
McAdam, B.F., et al., "Systemic biosynthesis of prostacyclin by cyclooxygenase (COX)-2: The human pharmacology of a selective inhibitor of COX-2," Proc Natl. Acad. Sci. 96: 272-277 and 96: 5890, 1999.
McLaurin Declaration under 1.132, submitted in U.S. Appl. No. 10/787,621, dated Aug. 15, 2006, 13 pages.
Metti et al., "Plasma Beta Amyloid Level and Depression in Older Adults"; J Gerontol A Biol Sci Med Sci. 68(1):74-9, PMID: 22499763, 2013.
Office of Environmental Health Hazard Assessment Report, "Air Toxics Hot Spots Program Risk Assessment Guidelines, Part IV, Technical Support Document for Exposure Assessment and Stochastic Analysis," Sep. 2000, 10 pages.
(OMIM)—Amyotrophic Lateral Sclerosis 1, In Online Mendelian Inheritance in Man, John Hopkins University, No. 105400; http://ncbi.nih.gov/entrez/dispomim.egi?id+105400, 24 pages.
Salloway et al., "Safety and Efficacy of a Phase 2 Randomized, Placebo-Controlled Dose-Ranging Study of ELND005 (Scyllo-inositol) in Mild to Moderate Alzheimer's Disease", International Conference on Alzheimers Disease (ICAD) meeting, to be held Jul. 16-21, 2011, Paris, France Poster Presentation # P2-50, Jul. 18, 2011.
Seedat S, Stein D.J., "Inositol augmentation of serotonin reuptake inhibitors in treatment-refractory obsessive disorder: an open trial,". Int. Clin. Psychophannacol. 14: 353-356 (1999).
Stathopulos, P.B., et al, "Cu/Zn superoxide dismutase mutants associated with amyotrophic lateral sclerosis show enhanced formation of aggregates in vitro," ProcNatlAcadSoc USA. 100(12):7021-7026, 2003.
Sun, Yet al., Bioorg Med Chem. 16(15), 7177-7184, 2008.
Takahashi, H et al., "Novel Synthesis of Enantiomerically Pure Natural Inositols and Their Diasterolisomers", Journal of Organic Chemistry, 66(8):2705-2706, 2001.
Van Reekum et al., "Diagnosis of dementia and treatment of Alzheimer's disease. Pharmacologic management of disease progression and cognitive impairment," Can Family Physician, 45: 945-52, 1999.
Extended Search Report issued in corresponding application EP09818730, dated Mar. 21, 2012, 3 pages.
Extended Search Report issued in corresponding application EP10010477, dated Mar. 15, 2011, 9 pages.
European Search Report issued in corresponding application EP 09005295, dated Jan. 14, 2010, 8 pages.
Response to EP Search Report filed in corresponding application EP 10010477, dated Oct. 20, 2011, 5 pages.
Kesslak, J.P., et al., "OC54—Cognitive and Behavioral Assessment of Adults With Down Syndrome: Baseline Data From PHASE2A Study of the Investigational Agent ELND005," Press Release, Nov. 2014, 1 page.

* cited by examiner

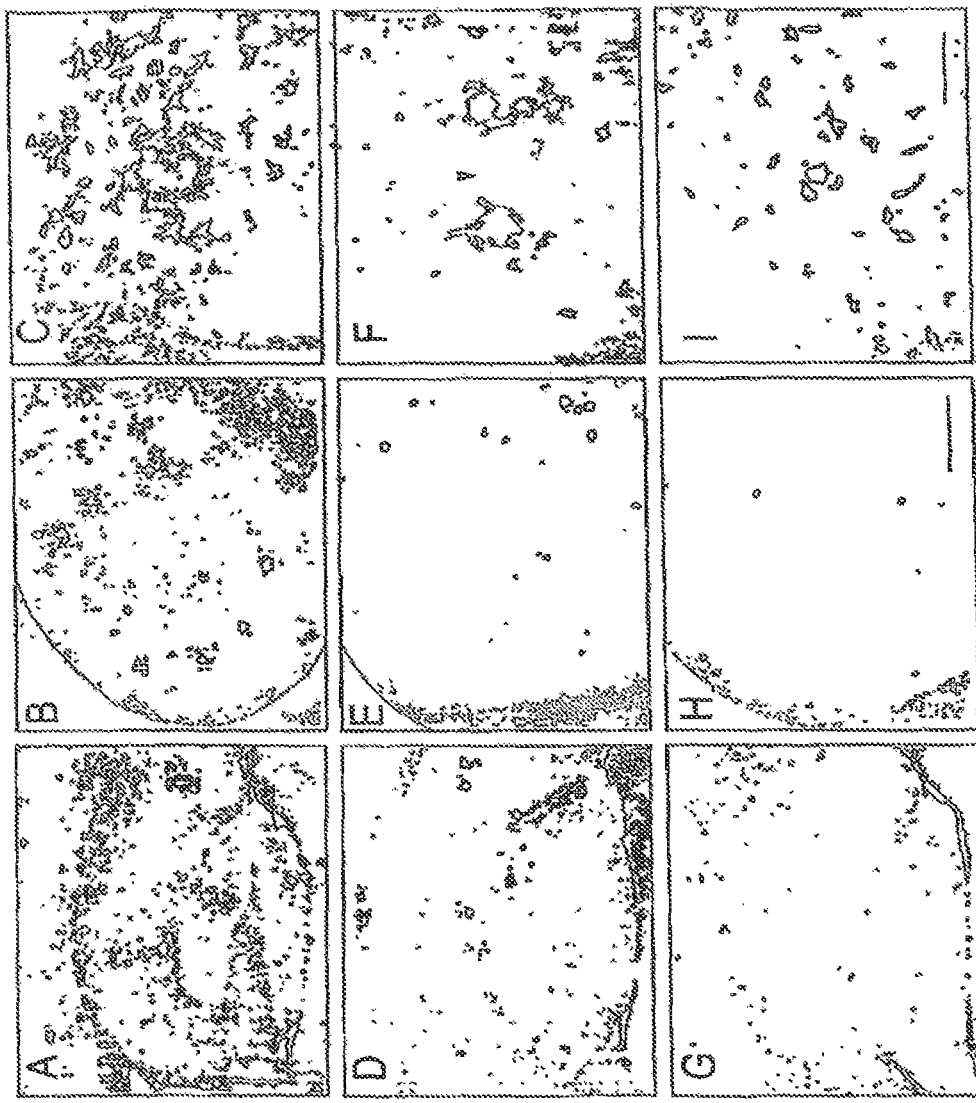

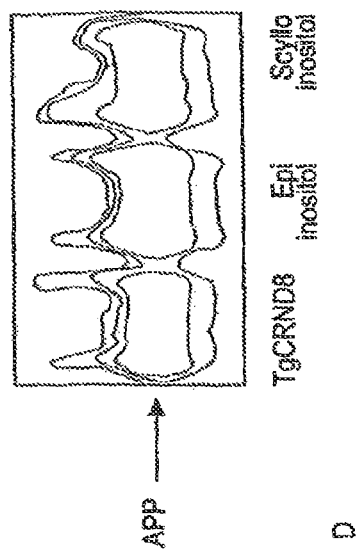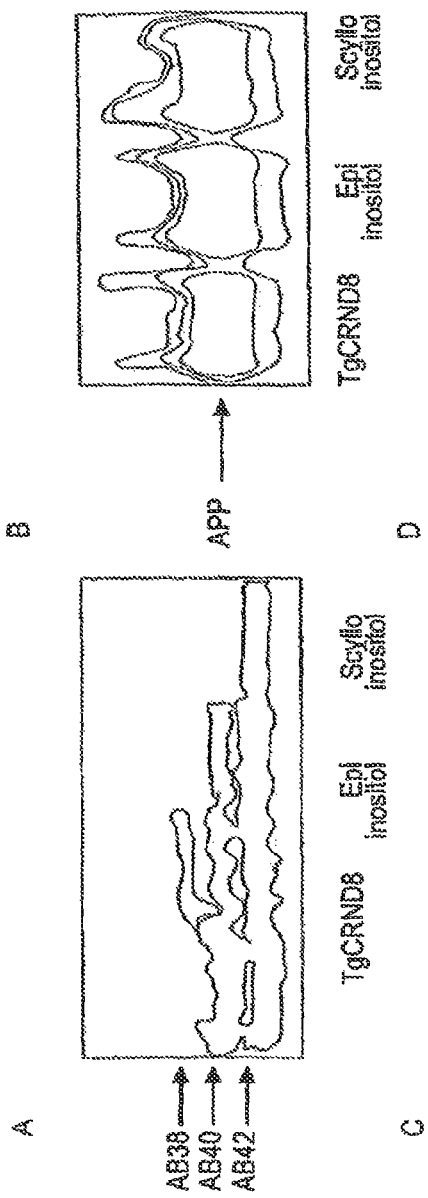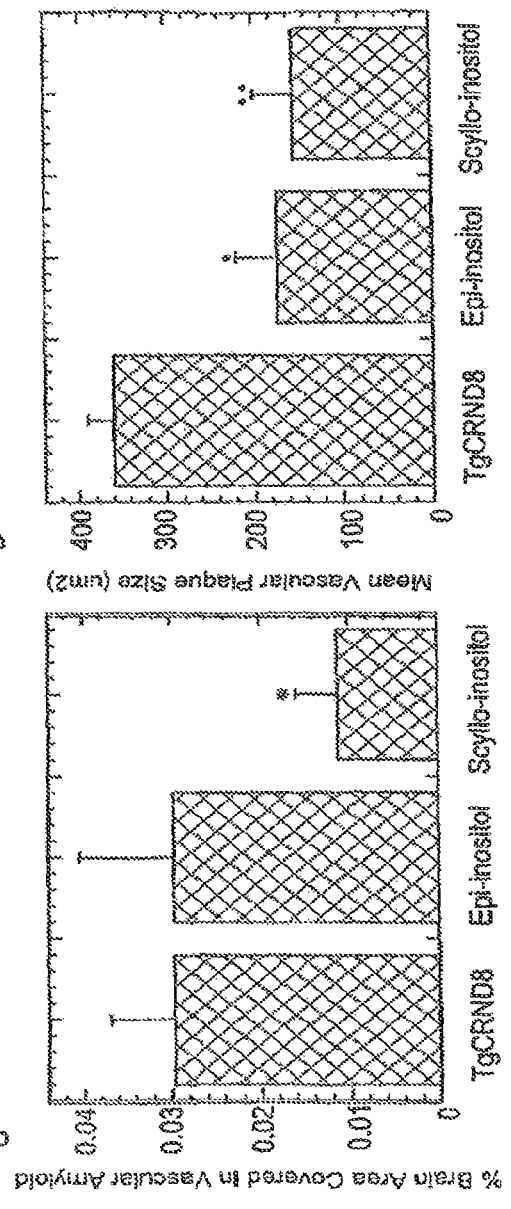

FIG. 11A
FIG. 11B
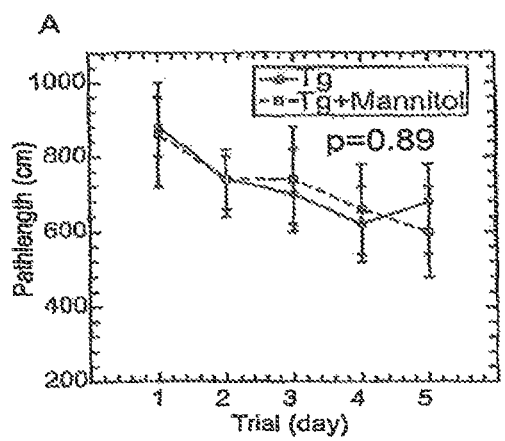
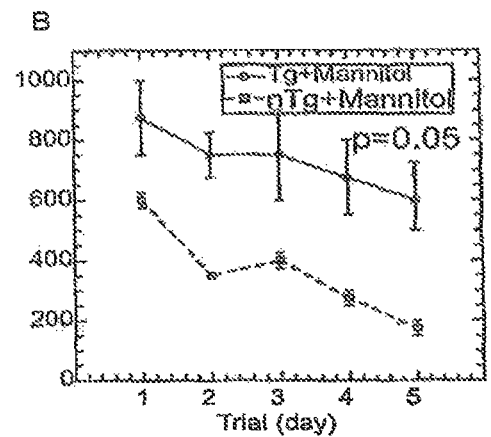
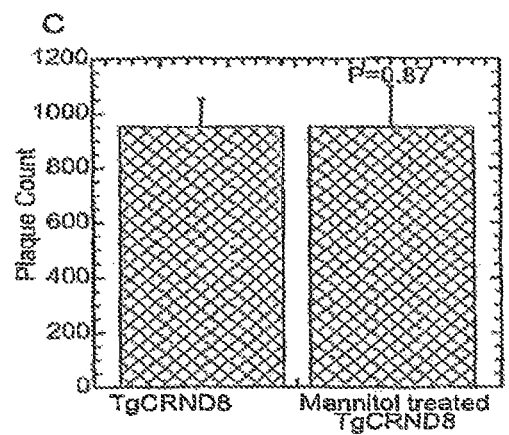
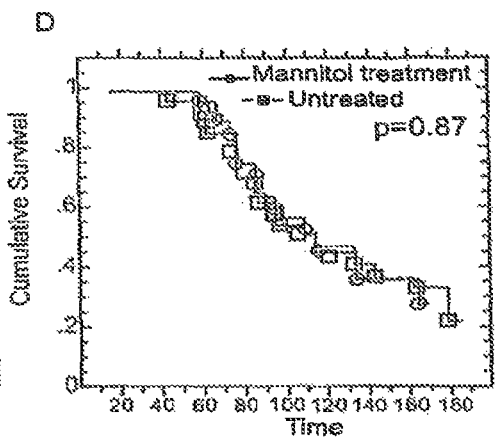
FIG. 11C
FIG. 11D

METHODS OF PREVENTING, TREATING, AND DIAGNOSING DISORDERS OF PROTEIN AGGREGATION

RELATED APPLICATIONS

This application claims the priority of U.S. Provisional Application Ser. Nos. 60/451,363, 60/520,958 and 60/523,534, filed Feb. 27, 2003, Nov. 17, 2003 and Nov. 19, 2003, respectively.

FIELD OF THE INVENTION

The invention relates to methods for treating Alzheimer's Disease and other amyloidoses; more particularly, it relates to methods for inhibiting and reducing amyloid fibril formation in therapeutic intervention in Alzheimer's disease and other amyloidoses.

DESCRIPTION OF THE RELATED ART

Alzheimer's disease is characterized neuropathologically by amyloid deposits, neurofibrillary tangles, and selective neuronal loss. The major component of the amyloid deposits is amyloid-β(Aβ), a 39-43 residue peptide. Soluble forms of Aβ generated from cleavage of amyloid precursor protein are normal products of metabolism. The importance of residues 1-42 (Aβ42) in Alzheimer's disease was highlighted in the discovery that mutations in codon 717 of the amyloid precursor protein gene, presenilin 1 and presenilin 2 genes result in an increased production of Aβ42 over Aβ1-40. These results in conjunction with the presence of Aβ 42 in both mature plaques and diffuse amyloid lead to the hypothesis that this more amyloidogenic species may be the critical element in plaque formation. This hypothesis was supported by the fact that Aβ42 deposition precedes that of Aβ40 in Down's syndrome in PS1 mutations and in hereditary cerebral hemorrhage with amyloidosis.

Many in vitro studies have demonstrated that Aβ can be neurotoxic or enhance the susceptibility of neurons to excitotoxic, metabolic, or oxidative insults. Initially it was thought that only the fibrillar form of A was toxic to neurons but more thorough characterization of Aβ structures demonstrated that dimers and small aggregates of Aβ are also neurotoxic. These data suggested that prevention of Aβ oligomerization would be a likely strategy to prevent AD-related neurodegeneration. Several studies have demonstrated that in vitro Aβ-induced neurotoxicity can be ablated by compounds that can increase neuronal resistance by targeting cellular pathways involved in apoptosis, block downstream pathways after Aβ induction of destructive routes, or block Aβ oligomerization and ultimately fibril formation. The site at which Aβ acts to induce neurotoxicity has yet to be elucidated but its toxic effects have been blocked by a variety of disparate agents.

Docking of Aβ-fibrils to neuronal and glial cell membranes may be an early and intervenable step during the progression of AD. Formation of amyloid plaques, as well as neurotoxicity and inflammation may be direct or indirect consequences of the interaction of A with molecules containing sugar moieties. Previous studies have demonstrated that Aβ interaction with glycosaminoglycans results in aggregation of Aβ possibly adding to their insolubility and plaque persistence. Glycosaminoglycans have also been implicated in neuronal toxicity and microglial activation. Alternatively, interaction with glycolipids such as gangliosides results in the stabilization and prevention of Ab fibril formation, as well as, the site of Aβ production. The family of phosphatidylinositols, on the other hand, results in acceleration of fibril formation. The headgroup of phosphatidylinositol is myo-inositol, a naturally occurring simple sugar involved in lipid biosynthesis, signal transduction, and osmolarity control.

It is also noteworthy that a variety of other human diseases also demonstrate amyloid deposition and usually involve systemic organs (i.e. organs or tissues lying outside the central nervous system), with the amyloid accumulation leading to organ dysfunction or failure. In Alzheimer's disease and "systemic" amyloid diseases, there is currently no cure or effective treatment, and the patient usually dies within 3 to 10 years from disease onset.

U.S. Pat. No. 4,847,082 discloses the use of phytic acid, a phytate salt, an isomer or hydrolysate of phytic acid for the treatment of Alzheimer's disease. It also discloses that isomers of phytic acid or phytate salt comprise the hexakisphosphate myo-inositol, hexakisphosphate scyllo-inositol, hexakisphosphate D-chiro-inositol, hexakisphosphate L-chiro-inositol, hexakisphosphate neo-inositol and hexakisphosphate muco-inositol conformations. Phytic acid is inositol-hexakisphosphate (IP6).

U.S. Pat. No. 5,112,814 discloses the use of phytic acid and isomers thereof for the treatment of Parkinson's disease. As is the case with U.S. Pat. No. 4,847,082, the phytic acid isomers disclosed in this patent retain the six phosphate groups on the six-carbon inositol sugar.

It is noteworthy that in subsequent publications, the ability of inositol-monophosphate, inositol-1,4-bisphosphate and inositol-1,4,5-triphosphate to inhibit amyloid-beta peptide fibrillogenesis were investigated and found not to be effective (*J. Mol. Biol.* 278:183-194, 1998).

Barak et al. disclose the use of inositol for the treatment of Alzheimer's Disease (AD). (*Prog Neuro-psychoparmacol & Biol Psychiat.* 20:729-735, 2000). However, this reference does not disclose the use of inositol isomers. Patients treated with inositol did not show any significant differences in overall cognitive function scores (CAMCOG index) between inositol and placebo (dextrose) in AD patients while two specific subscales of the CAMCOG index did show significant improvement (orientation and language).

Levine J, reviews the above Barak et al. paper and specifically states that inositol treatment is not beneficial in AD or ECT-induced cognitive impairment (Eur Neuropsychoparm. 1997; 7,147-155, 1997).

Colodny L, et al. suggests further studies for the usefulness of inositol in Alzheimer's disease by referring to the above Barak et al. paper and therefore does not disclose or suggest such use for inositol isomers (*Altern Med Rev* 3(6):432-47, 1998).

McLaurin et al. disclosed that myo-inositol stabilizes a small micelle of Aβ42 (*J. Mol. Biol.* 278, 183-194, 1998). In addition, McLaurin et al. disclose that epi- and scyllo-but not chiro-inositol were able to induce a structural transition from random to β-structure in Aβ42 (*J Biol Chem*. June 16; 275(24):18495-502, 2000; and *J Struct Biol* 130:259-270, 2000). Alternatively, none of the stereoisomers were able to induce a structural transition in Aβ40. Electron microscopy showed that inositol stabilizes small aggregates of Aβ42. These references also disclose that inositol-Aβ interactions result in a complex that is non-toxic to nerve growth factor-differentiated PC-12 cells and primary human neuronal cultures.

Much work in Alzheimer's disease has been accomplished, but little is conventionally known about compounds or agents for therapeutic regimes to arrest or reverse amyloid formation, deposition, accumulation and/or persistence that occurs in Alzheimer's disease and other amyloidoses.

New compounds or agents for therapeutic regimes to arrest or reverse amyloid formation, deposition, accumulation and/or persistence that occurs in Alzheimer's disease and other amyloidoses are therefore desperately needed.

SUMMARY OF THE INVENTION

The present invention provides a method of treating or preventing in a subject a condition of the central or peripheral nervous system or systemic organ associated with a disorder in protein folding or aggregation, or amyloid formation, deposition, accumulation, or persistence comprising administering to said subject a pharmaceutically effective amount of compound selected having the following structure:

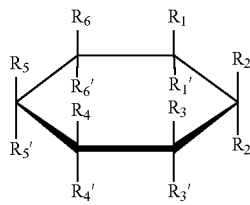

wherein each of $R_1$, $R_{1'}$, $R_2$, $R_{2'}$, $R_3$, $R_{3'}$, $R_4$, $R_{4'}$, $R_5$, $R_{5'}$, $R_6$, and $R_{6'}$ is independently selected from the group of:
(a) hydrogen atom;
(b) $NHR_7$, wherein said $R_7$ is selected from the group of hydrogen; $C_2$-$C_{10}$ acyl and $C_1$-$C_{10}$ alkyl;
(c) $NR_8R_9$, wherein said $R_8$ is $C_2$-$C_{10}$ acyl or $C_1$-$C_{10}$ alkyl and said $R_9$ is $C_2$-$C_{10}$ acyl or $C_1$-$C_{10}$ alkyl;
(d) $OR_{10}$, wherein said $R_{10}$ is selected from the group of no group, hydrogen, $C_2$-$C_{10}$ acyl, $C_1$-$C_{10}$ alkyl and $SO_3H$;
(e) $C_5$-$C_7$ glycosyl;
(f) $C_3$-$C_8$ cycloalkyl optionally substituted with a substituent selected from the group of hydrogen, OH, $NH_2$, SH, $OSO_3H$ and $OPO_3H_2$;
(g) $SR_{11}$ wherein $R_{11}$ is selected from the group of hydrogen, $C_1$-$C_{10}$ alkyl and $O_3H$;
(h) $C_1$-$C_{10}$ alkyl optionally substituted with a substituent selected from the group of hydrogen, $OR_{10}$, $NH_{R7}$, $NR_8R_9$, and $SR_{11}$; and
(i) $C_3$-$C_8$ cycloalkyl optionally substituted with a substituent selected from the group of hydrogen. $OR_{10}$, $NH_{R7}$, $NR_8R_9$ and $SR_{11}$, providing that the compound is not myo-inositol.

The present invention also provides a method of preventing abnormal protein folding, abnormal protein aggregation, amyloid formation, deposition, accumulation, or persistence, or amyloid lipid interactions in a subject comprising administering to said subject a pharmaceutically effective amount of a compound having the following structure:

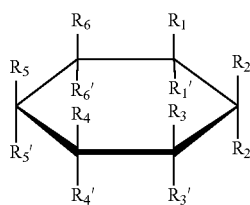

wherein each of $R_1$, $R_{1'}$, $R_2$, $R_{2'}$, $R_3$, $R_{3'}$, $R_4$, $R_{4'}$, $R_5$, $R_{5'}$, $R_6$, and $R_{6'}$ is independently selected from the group of:
(a) hydrogen atom;
(b) $NHR_7$, wherein said $R_7$ is selected from the group of hydrogen; $C_2$-$C_{10}$ acyl and $C_1$-$C_{10}$ alkyl;
(c) $NR_8R_9$, wherein said $R_8$ is $C_2$-$C_{10}$ acyl or $C_1$-$C_{10}$ alkyl and said $R_9$ is $C_2$-$C_{10}$ acyl or $C_1$-$C_{10}$ alkyl;
(d) $OR_{10}$, wherein said $R_{10}$ is selected from the group of no group, hydrogen, $C_2$-$C_{10}$ acyl, $C_1$-$C_{10}$ alkyl and $SO_3H$;
(e) $C_5$-$C_7$ glycosyl;
(f) $C_3$-$C_8$ cycloalkyl optionally substituted with a substituent selected from the group of hydrogen, OH, $NH_2$, SH, $OSO_3H$ and $OPO_3H_2$;
(g) $SR_{11}$ wherein $R_{11}$ is selected from the group of hydrogen, $C_1$-$C_{10}$ alkyl and $O_3H$;
(h) $C_1$-$C_{10}$ alkyl optionally substituted with a substituent selected from the group of hydrogen, $OR_{10}$, $NHR_7$, $NR_8R_9$ and $SR_{11}$; and
(i) $C_3$-$C_8$ cycloalkyl optionally substituted with a substituent selected from the group of hydrogen, $OR_{10}$, $NHR_7$, $NR_8R_9$ and $SR_{11}$, providing that the compound is not myo-inositol.

The present invention further provides a method of causing the dissociation of abnormally aggregated proteins and/or dissolving or disrupting pre-formed or pre-deposited amyloid fibril or amyloid in a subject comprising administering to said subject a pharmaceutically effective amount of a compound having the following structure:

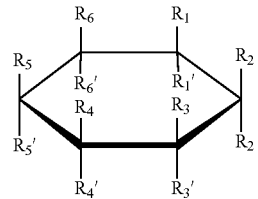

wherein each of $R_1$, $R_{1'}$, $R_2$, $R_{2'}$, $R_3$, $R_{3'}$, $R_4$, $R_{4'}$, $R_5$, $R_{5'}$, $R_6$, and $R_{6'}$ is independently selected from the group of:
(a) hydrogen atom;
(b) $NHR_7$, wherein said $R_7$ is selected from the group of hydrogen; $C_2$-$C_{10}$ acyl and $C_1$-$C_{10}$ alkyl;
(c) $NR_8R_9$, wherein said $R_8$ is $C_2$-$C_{10}$ acyl or $C_1$-$C_{10}$ alkyl and said $R_9$ is $C_2$-$C_{10}$ acyl or $C_1$-$C_{10}$ alkyl;
(d) $OR_{10}$, wherein said $R_{10}$ is selected from the group of no group, hydrogen. $C2$-$C_{10}$ acyl, $C_1$-$C_{10}$ alkyl and $SO_3H$;
(e) $C_5$-$C_7$ glycosyl;
(f) $C_3$-$C_8$ cycloalkyl optionally substituted with a substituent selected from the group of hydrogen, OH, $NH_2$, SH, $OSO_3H$ and $OPO_3H_2$;
(g) $SR_{11}$, wherein $R_{11}$ is selected from the group of hydrogen, $C_1$-$C_{10}$ alkyl and $O_3H$;
(h) $C_1$-$C_{10}$ alkyl optionally substituted with a substituent selected from the group of hydrogen, $OR_{10}$, $NH_{R7}$, $NR_8R_9$ and $SR_{11}$; and
(i) $C_3$-$C_8$ cycloalkyl optionally substituted with a substituent selected from the group of hydrogen, $OR_{10}$, $NHR_7$, $NR_8R_9$ and $SR_{11}$,
providing that the compound is not myo-inositol.

The present invention also provides a method of diagnosing the presence of abnormally folded or aggregated protein and/or amyloid fibril or amyloid in a subject comprising: (a) administering to said subject a radioactive compound or compound tagged with a substance that emits a detectable signal in a quantity sufficient and under conditions to allow for the binding of said compound to the abnormally folded or aggregated protein and/or fibrils or amyloid, if present; and (b) detecting the radioactivity or the signal from the compound bound to the abnormally folded or aggregated protein and/or fibrils or amyloid, thus diagnosing the presence of abnormally folded or aggregated protein and/or amyloid fibril or amyloid in said subject, wherein said compound has the following structure:

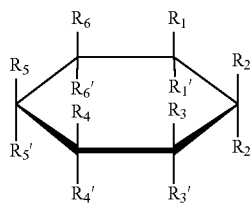

wherein each of $R_1$, $R_{1'}$, $R_2$, $R_{2'}$, $R_3$, $R_{3'}$, $R_4$, $R_{4'}$, $R_5$, $R_{5'}$, $R_6$, and $R_{6'}$ is independently selected from the group of:
(a) hydrogen atom;
(b) $NHR_7$, wherein said $R_7$ is selected from the group of hydrogen; $C_2$-$C_{10}$ acyl and $C_1$-$C_{10}$ alkyl;
(c) $NR_8R_9$, wherein said $R_8$ is $C_2$-$C_{10}$ acyl or $C_1$-$C_{10}$ alkyl and said $R_9$ is $C_2$-$C_{10}$ acyl or $C_1$-$C_{10}$ alkyl;
(d) $OR_{10}$, wherein said $R_{10}$ is selected from the group of no group, hydrogen, $C_2$-$C_{10}$ acyl, $C_1$-$C_{10}$ alkyl and $SO_3H$;
(e) $C_5$-$C_7$ glycosyl;
(f) $C_3$-$C_8$ cycloalkyl optionally substituted with a substituent selected from the group of hydrogen, OH, $NH_2$, SH, $OSO_3H$ and $OPO_3H_2$;
(g) $SR_{11}$, wherein $R_{11}$ is selected from the group of hydrogen, $C_1$-$C_{10}$ alkyl and $O_3H$;
(h) $C_1$-$C_{10}$ alkyl optionally substituted with a substituent selected from the group of $OR_{10}$, $NH_{R7}$, $NR_8R_9$ and $SR_{11}$; and
(i) $C_3$-$C_8$ cycloalkyl optionally substituted with a substituent selected from the group of hydrogen, $OR_{10}$, $NHR_7$, $NR_8R_9$ and $SR_{11}$,
providing that the compound is not myo-inositol.

The present invention further provides a method of diagnosing the presence of abnormally folded or aggregated protein and/or amyloid fibril or amyloid in a subject comprising: (a) collecting a sample from said subject; (b) contacting said sample with a radioactive compound or compound tagged with a substance that emits a detectable signal under conditions to allow the binding of said compound to the abnormally folded or aggregated protein and/or amyloid fibril or amyloid if present; and (c) detecting the radioactivity or the signal from the compound bound to the abnormally folded or aggregated protein and/or fibrils or amyloid, thus diagnosing the presence of abnormally folded or aggregated protein and/or amyloid fibril or amyloid in said subject, wherein said compound has the following structure:

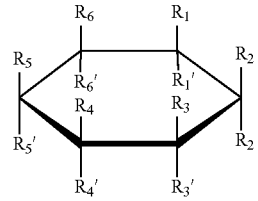

wherein each of $R_1$, $R_{1'}$, $R_2$, $R_{2'}$, $R_3$, $R_{3'}$, $R_4$, $R_{4'}$, $R_5$, $R_{5'}$, $R_6$, and $R_{6'}$, is independently selected from the group of;
(a) hydrogen atom;
(b) $NHR_7$, wherein said $R_7$ is selected from the group of hydrogen, $C_2$-$C_{10}$ acyl and $C_1$-$C_{10}$ alkyl;
(c) $NR_8R_9$, wherein said $R_8$ is $C_2$-$C_{10}$ acyl or $C_1$-$C_{10}$ alkyl and said $R_9$ is $C_2$-$C_{10}$ acyl or $C_1$-$C_{10}$ alkyl;
(d) $OR_{10}$, wherein said $R_{10}$ is selected from the group of no group, hydrogen, $C_2$-$C_{10}$ acyl, $C_1$-$C_{10}$ alkyl and $SO_3H$;
(e) $C_5$-$C_7$ glycosyl;
(f) $C_3$-$C_8$ cycloalkyl optionally substituted with a substituent selected from the group of hydrogen, OH, $NH_2$, SH, $OSO_3H$ and $OPO_3H_2$;
(g) $SR_{11}$, wherein $R_{11}$ is selected from the group of hydrogen, $C_1$-$C_{10}$ alkyl and $O_3H$;
(h) $C_1$-$C_{10}$ alkyl optionally substituted with a substituent selected from the group of $OR_{10}$, $NH_{R7}$, $NR_8R_9$ and $SR_{11}$; and
(i) $C_3$-$C_8$ cycloalkyl optionally substituted with a substituent selected from the group of hydrogen, $OR_{10}$, $NHR_7$, $NR_8R_9$ and $SR_{11}$,
providing that the compound is not myo-inositol.

BRIEF DESCRIPTION OF THE DRAWINGS

FIG. 1A shows the structure of myo-, epi- and scyllo-inositol while

FIGS. 2A-2I show at 6 months of age, the plaque burden and astrogliosis in TgCRND8 treated with epi- and scyllo-inositol treated mice. Control animals have a high plaque load and astrogliosis in the hippocampus (2A) and cerebral cortex (2B). Higher magnification demonstrates that astrocytic activation is not only associated with plaque load (2C). Epi-inositol treatment has a modest effect on amyloid burden with a decrease in astrogliosis (2D, 2E and 2F). Scyllo-inositol treatment significantly decreased amyloid burden and gliosis (2G, 2H, and 2I). Higher magnification illustrates the smaller mean plaque size in scyllo-inositol treated mice (2I). Astrocytes were labeled using anti-GFAP antibody and plaque burden was identified using anti-Aβ antibody. Scale Bar 450 microns (A,B,D,E,G,H) and 94 microns (C,F,I).

FIGS. 3A-3D show that the Aβ species, 1-42, 1-40 and 1-38, in control and treated TgCRND8 mice was indistinguishable (3A) as was the extent of APP processing (3B).

Vascular amyloid burden was quantitated on serial sagittal sections in treated and untreated TgCRND8 mice. TgCRND8 mice have a significant vascular amyloid burden that is associated with small and medium sized vessels, the load is decreased in scyllo-inositol treated TgCRND8 mice (3A). Scyllo-inositol treatment significantly decreased the total vascular load in comparison to untreated and epi-inositol treated TgCRND8 mice (3C). Scyllo-inositol decreases plaque deposition as illustrated by the significant decrease in mean plaque size (3D).

Figure 4:
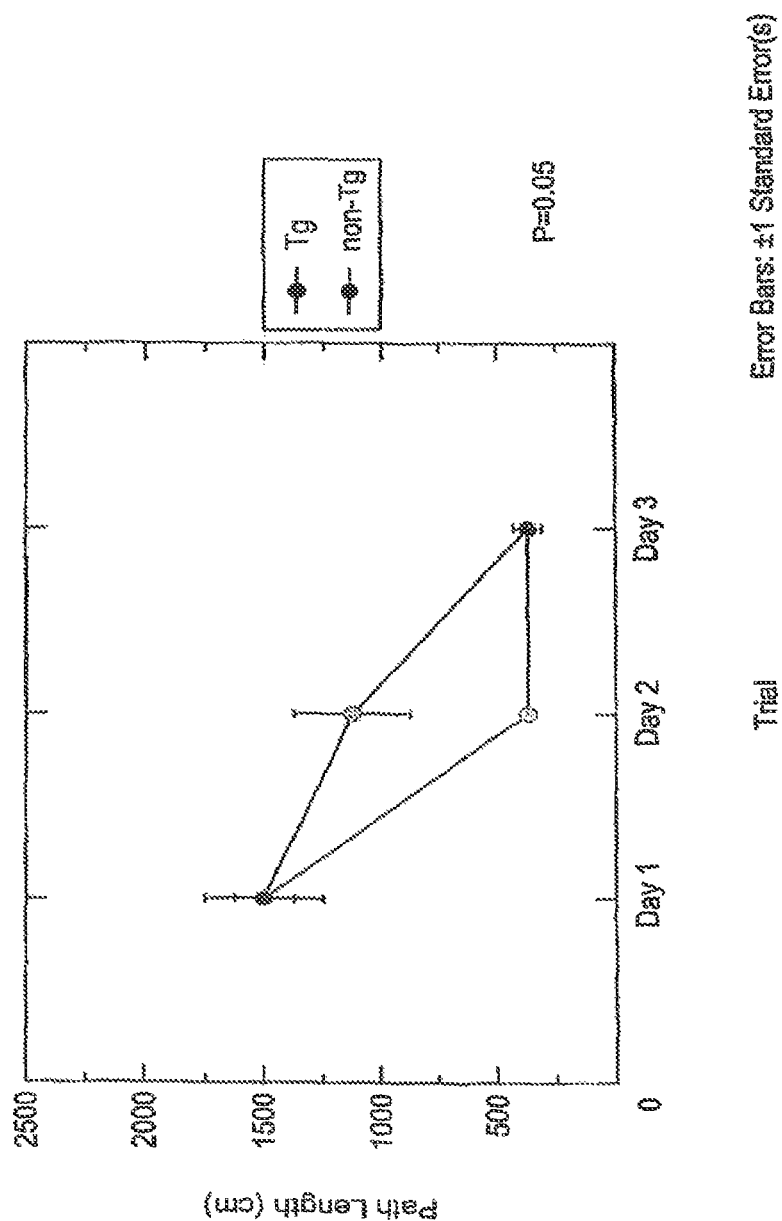

FIG. 4 shows the effect of water on the cognitive function of TgCRND8 and non-Tg mice using the spatial reference memory version of the Morris Water Maze in a three day trial paradigm.

Figure 5:
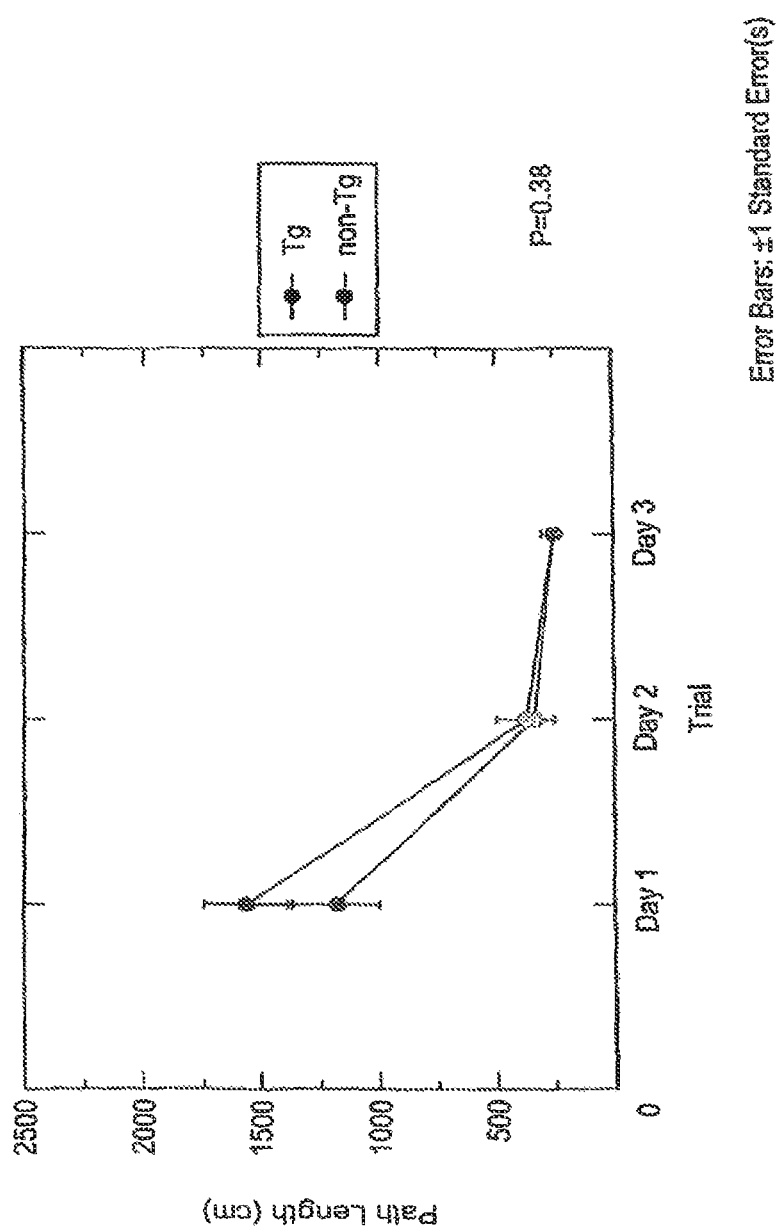

FIG. 5 shows the effect of scyllo-inositol on the cognitive function of TgCRND8 and non-Tg mice using the spatial reference memory version of the Morris Water Maze in a three day trial paradigm.

Figure 6:
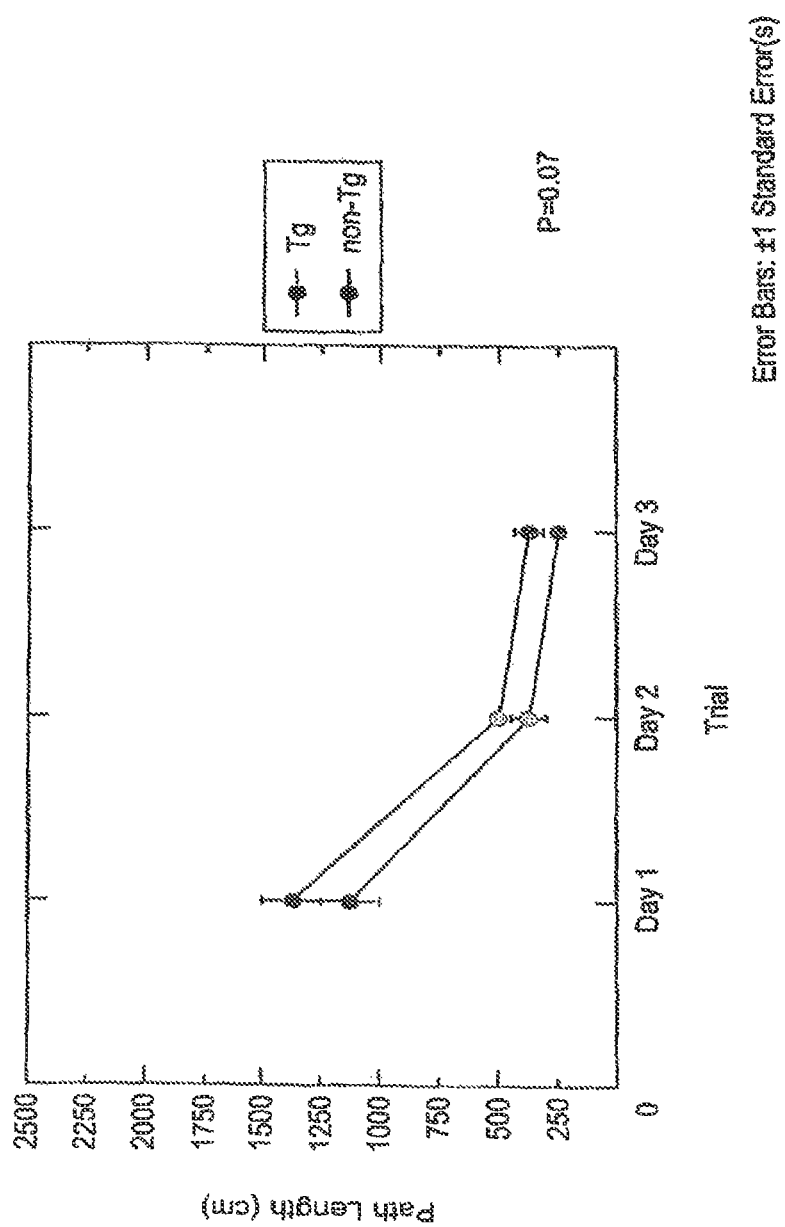

FIG. 6 shows the effect of epi-inositol on the cognitive function of TgCRND8 and non-Tg mice using the spatial reference memory version of the Morris Water Maze in a three day trial paradigm.

Figure 7:
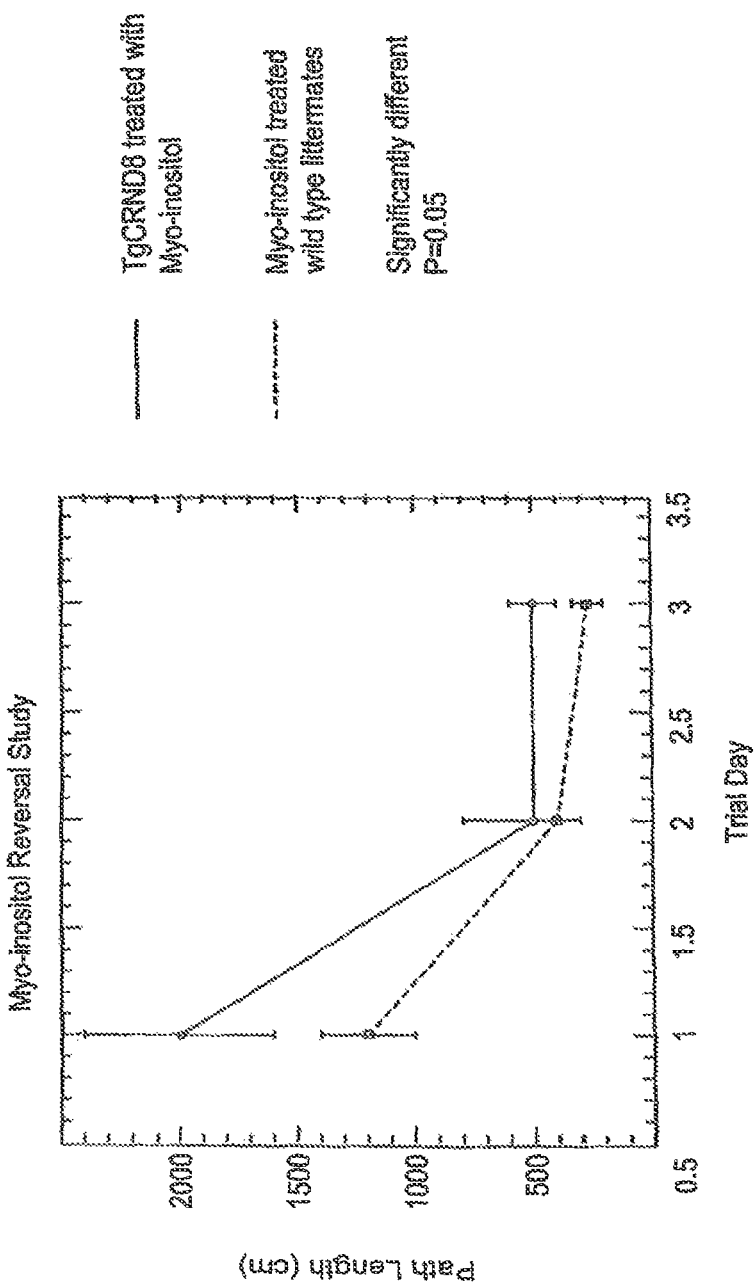

FIG. 7 shows the effect of myo-inositol on the cognitive function of TgCRND8 and non-Tg mice using the spatial reference memory version of the Morris Water Maze in a three day trial paradigm.

Figure 8:
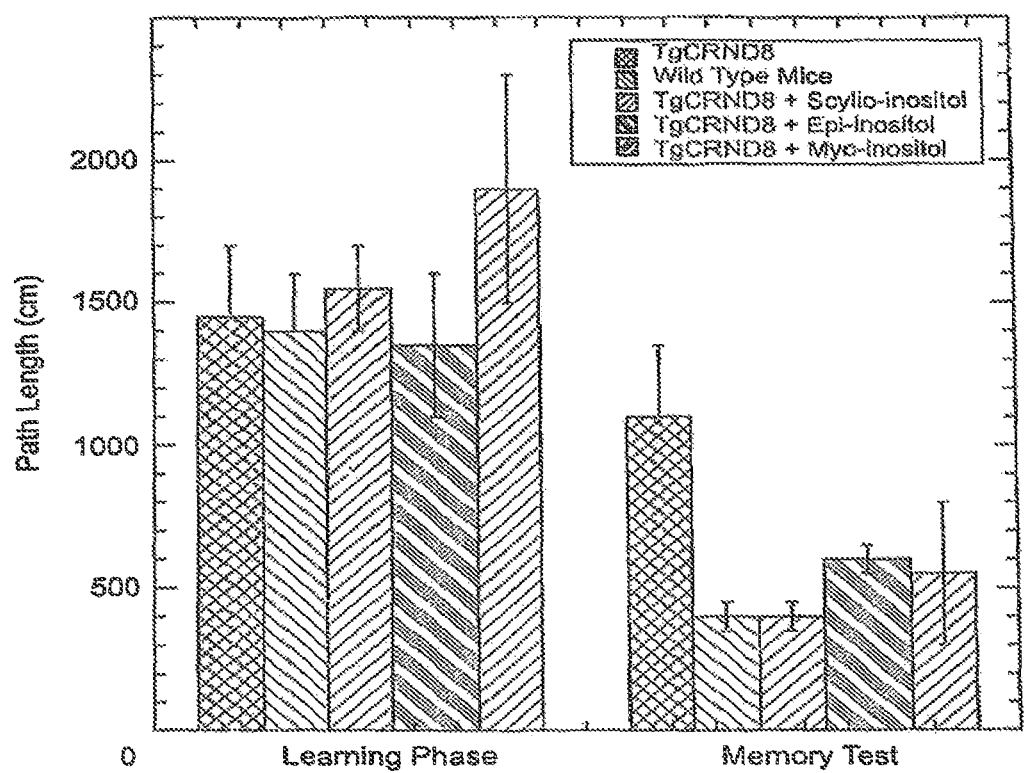

FIG. 8 shows the effect of scyllo-inositol, epi-inositol and myo-inositol on the cognitive function of TgCRND8 (learning phase and memory test) and compared with wild type mice using the spatial reference memory version of the Morris Water Maze in a three-day trial paradigm.

Figure 9:
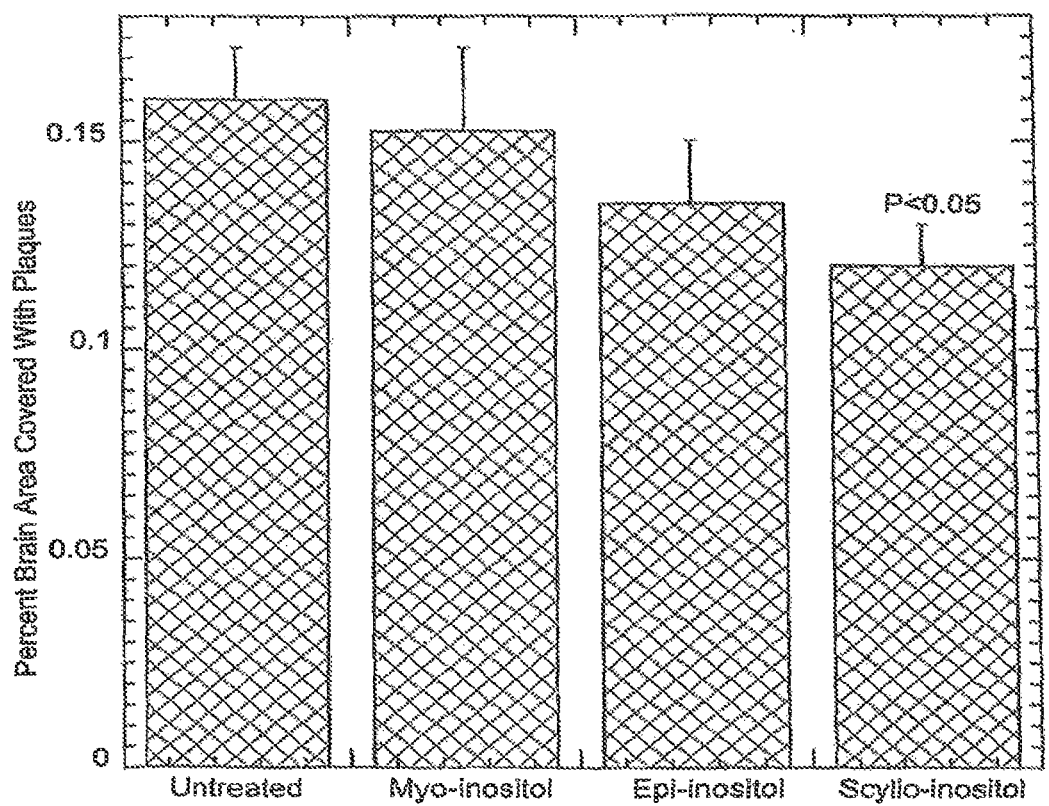

FIG. 9 shows the percentage of brain area covered with plaques in untreated TgCRND8 mice versus mice treated with scyllo-inositol, epi-inositol or myo-inositol.

Figures 10A, 10B:
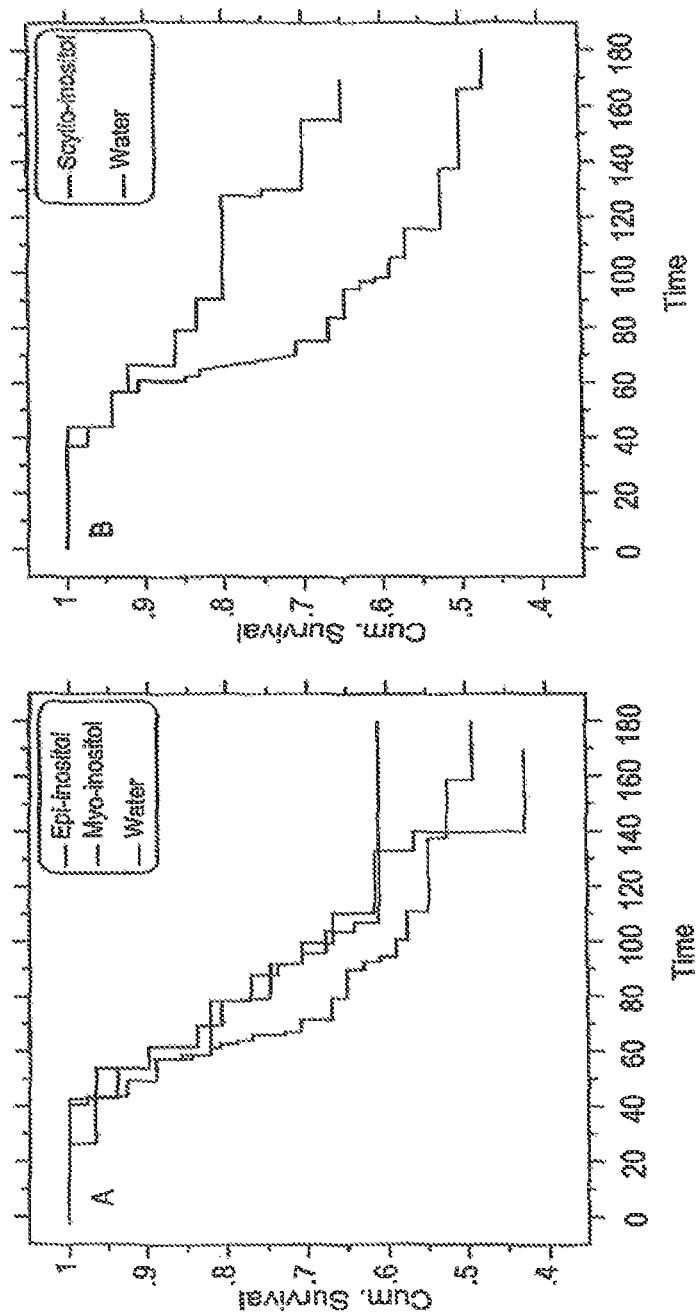

FIGS. 10A and 10B show the survival rates of TgCRND8 mice treated with water versus epi-inositol or myo-inositol (10A) or versus scyllo-inositol (10B).

FIGS. 11 A-D show the results of spatial reference memory version of the Morris Water Maze test in 6-month old TgCRND8 mice non-treated or treated with mannitol (A,B). Mannitol treated TgCRND8 mice were not significantly different from untreated TgCRND8 mice ($p=0.89$; A). The performance of mannitol treated TgCRND8 mice was significantly different from mannitol treated non-Tg littermates ($p=0.05$; B). Plaque burden was analyzed at 6 months of age using quantitative image analyses (C). Mannitol treated TgCRND8 mice were indistinguishable from untreated TgCRND8 mice when plaque count was used as a measure of total plaque burden ($p=0.87$). Vertical bars represent S.E.M. Kaplan-Meier Cumulative survival plots for TgCRND8 mice treated and untreated with mannitol (D). The two cohorts of animals, n=35 per group, were not significantly different as determined by the Tarone-Ware statistical test, $p=0.87$.

Figures 12A, 12B:
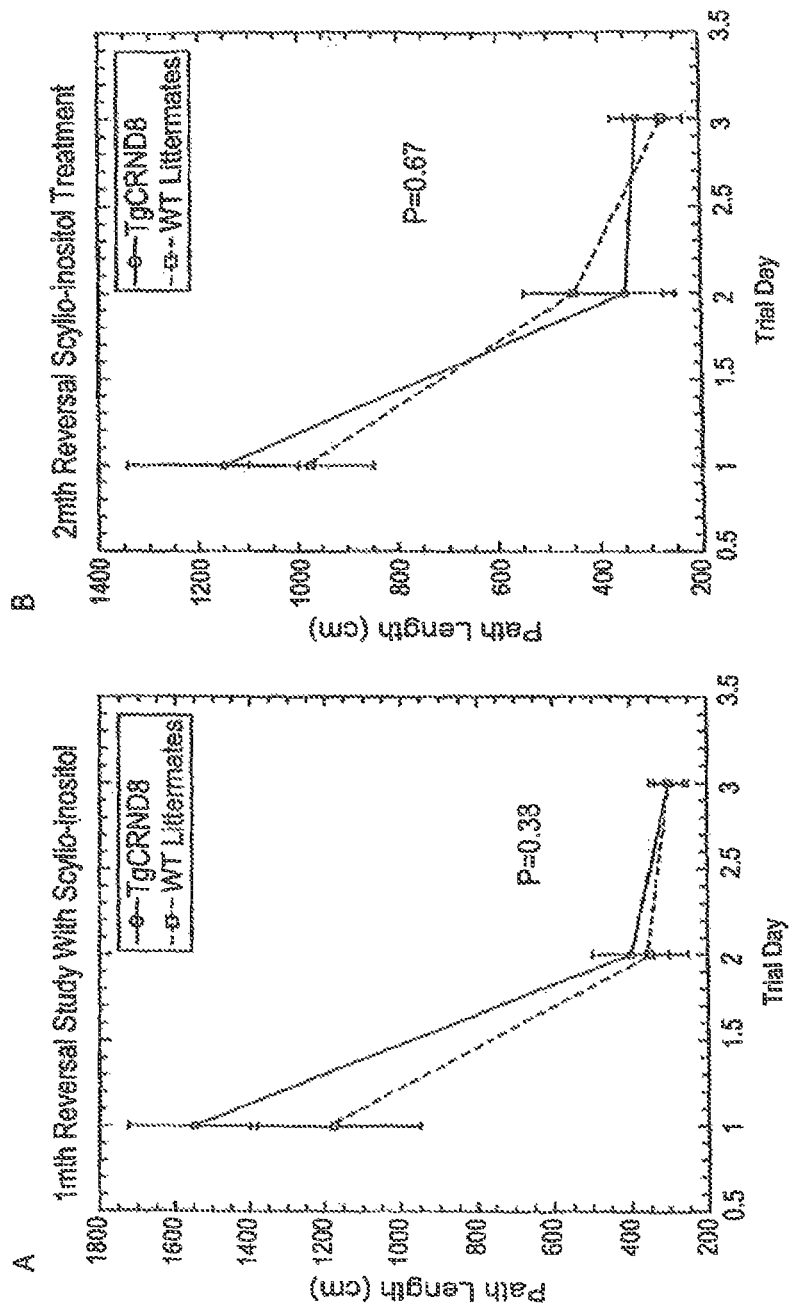

FIGS. 12A and B show the results of a spatial reference memory test in the treatment studies when performed in a 3-day trial paradigm. The performance of scyllo-inositol treated TgCRND8 mice was comparable to scyllo-inositol treated non-Tg littermates ($p=0.38$; A). In agreement, scyllo-inositol treated TgCRND8 mice remained indistinguishable from non-Tg littermates after two months of treatment ($p=0.67$; B).

Figures 13A, 13B:
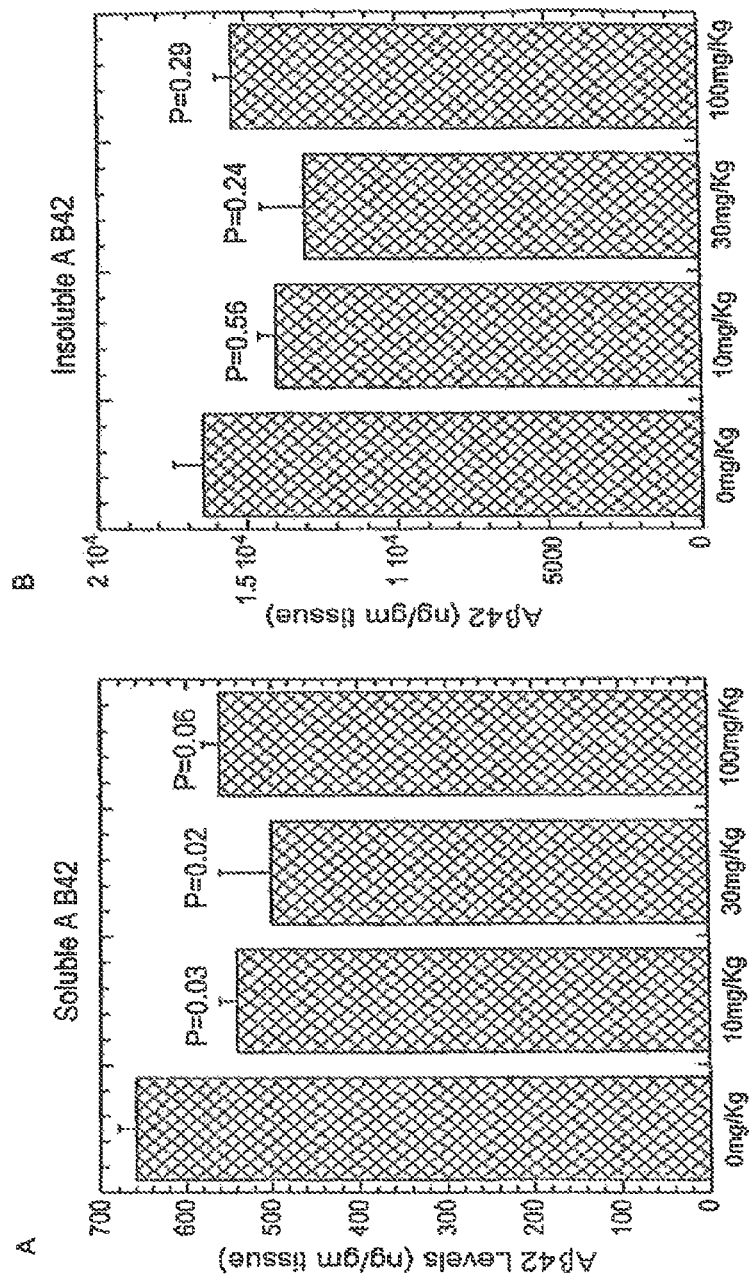

FIGS. 13A and B show A$\beta$ levels within the CNS after administration of various doses of scyllo-inositol were administered once daily for one month to five month old TgCRND8 mice. Soluble A$\beta$42 levels were decreased at all doses and were significantly different from untreated controls (A). In contrast, insoluble A$\beta$42 was not significantly different under all conditions (B). Vertical bars represent S.E.M.

Figures 14A, 14B:
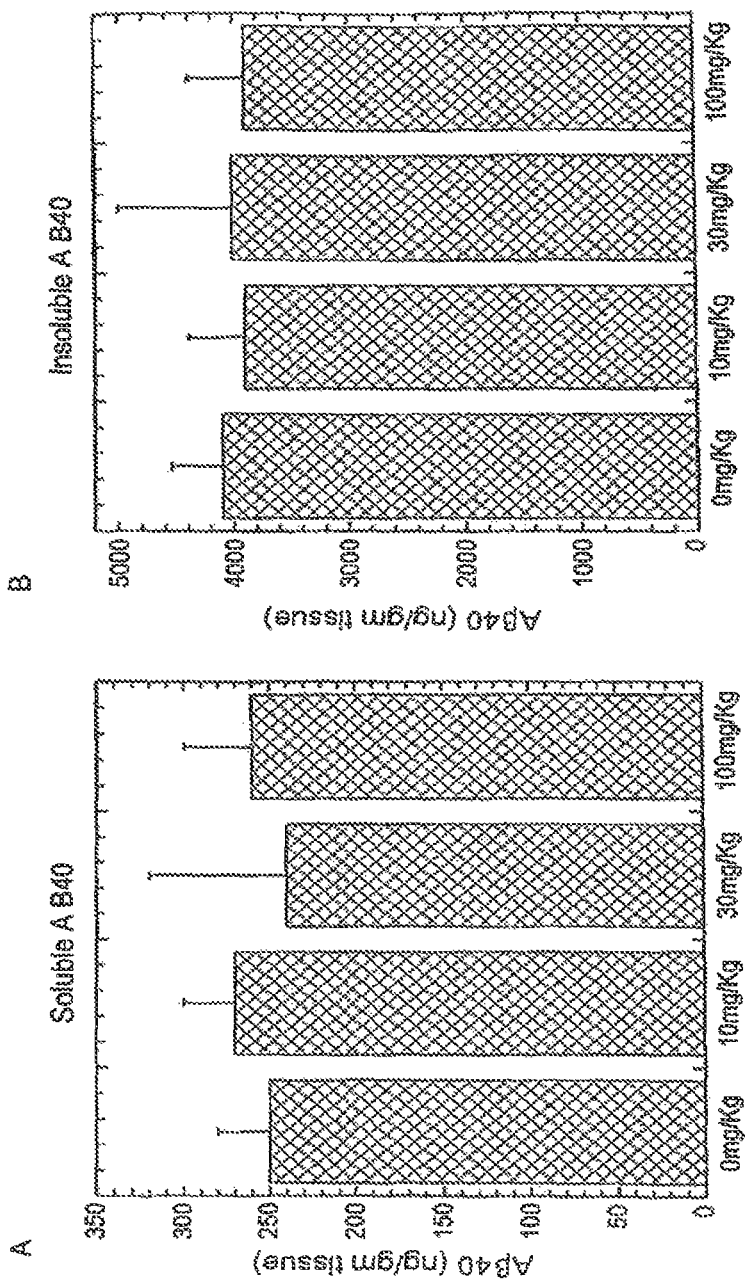

FIGS. 14A and B. TgCRND8 mice administered various doses of scyllo-inositol once daily for one month were analyzed for levels of brain A$\beta$40. No difference was detected in soluble (A) and insoluble (B) levels of A$\beta$40 of untreated and scyllo-inositol treated TgCRND8 mice at all doses examined.

Figure 15:
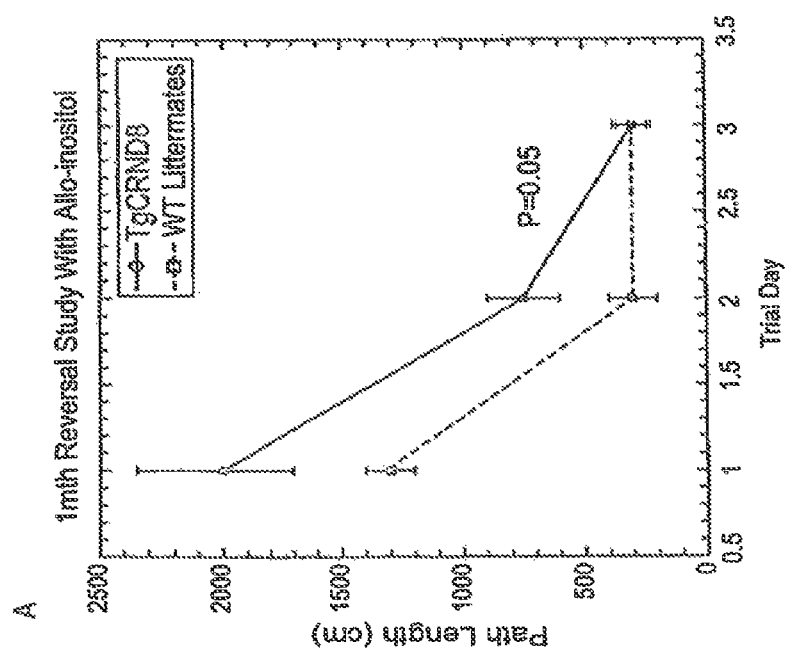
Figure 16B:
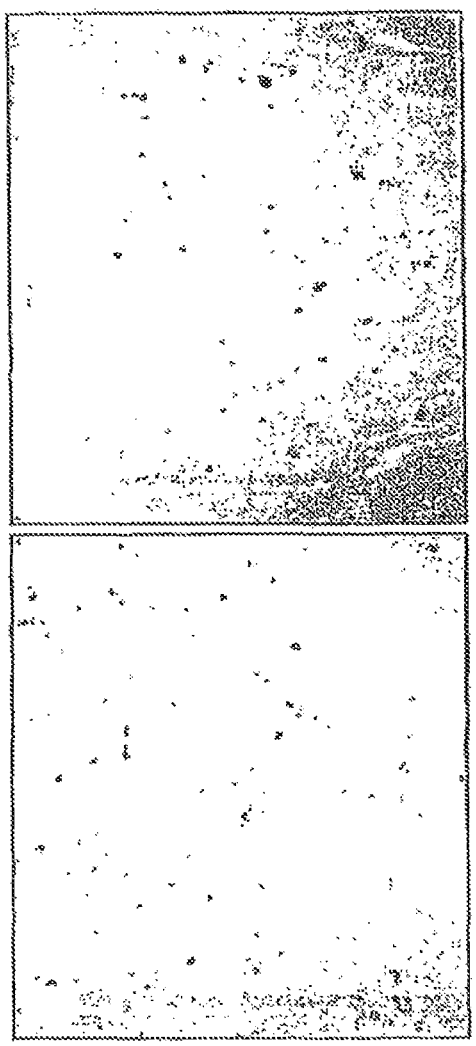
Figure 16D:
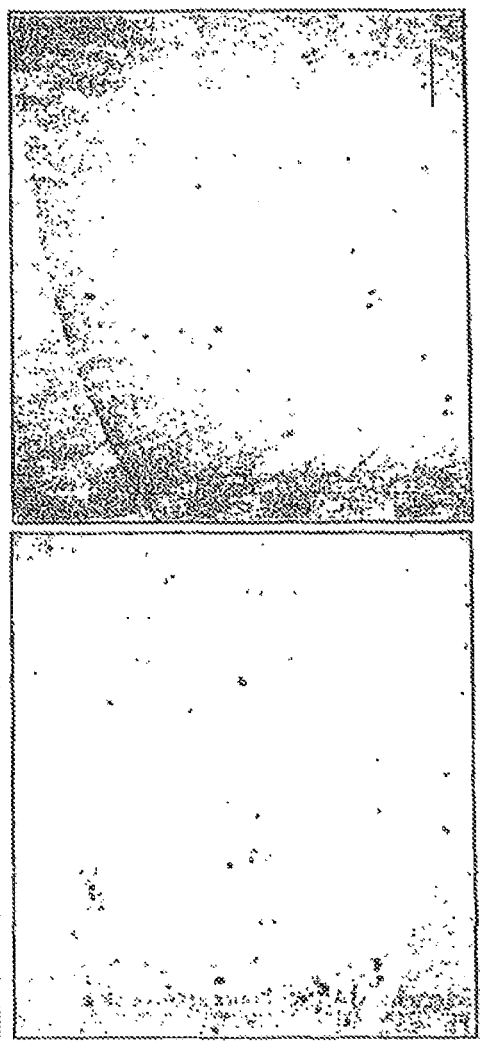
Figure 16A:
Figure 16C:

FIG. 15 shows the cognitive performance of 6-month old allo-inositol-treated TgCRND8 mice compared with that of their non-transgenic littermates.

FIGS. 16A-D show that at 2 months of age, the plaque burden in TgPS1×APP mice is decreased in scyllo-inositol treated mice. Control animals have a high plaque load in the hippocampus (A) and cerebral cortex (B). Scyllo-inositol treatment significantly decreased amyloid burden (C. D). Plaque burden identified using anti-A$\beta$ antibody (brown). Scale Bar 300 µm.

Figures 17A, 17B, 17C:
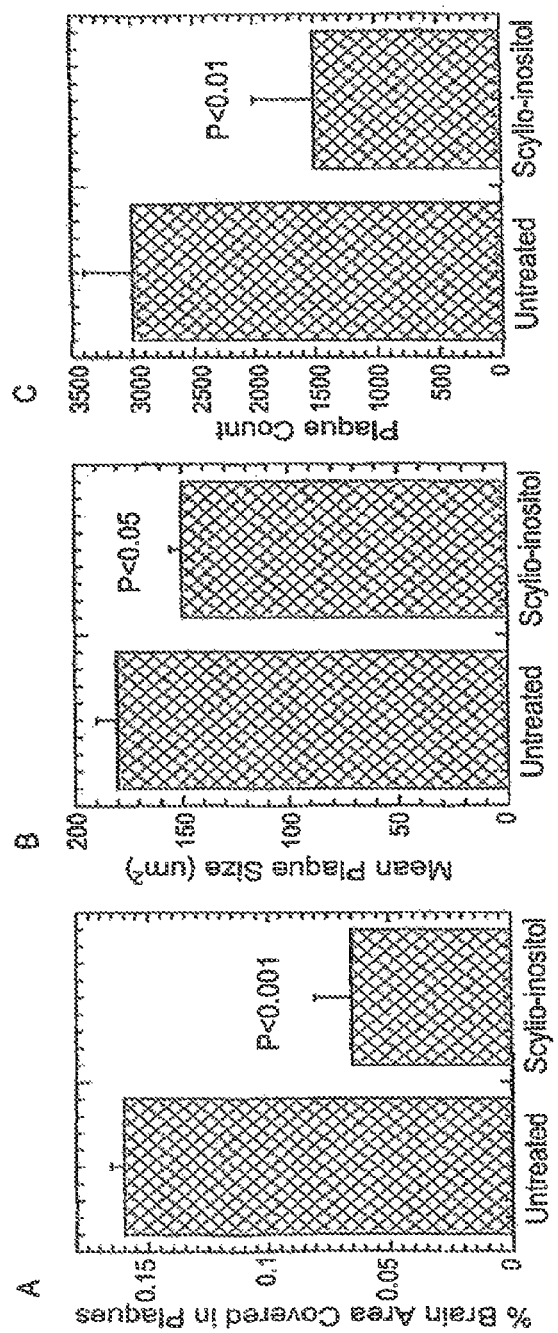

FIGS. 17A-C show the quantification of the plaque burden in TgPS1×APP mice after scyllo-inositol treatment. The percent brain area covered in plaques (A), mean plaque size (B) and plaque count (C) were significantly reduced. Vertical bars are S.E.M.

DETAILED DESCRIPTION OF THE INVENTION

The present invention discloses novel, unpredictable and unexpected properties of certain inositol stereoisomers in relation to the treatment of amyloid-related disorders such as Alzheimer's Disease.

It has been surprisingly discovered that certain stereoisomers of inositol and related compounds block A$\beta$-induced progressive cognitive decline and cerebral amyloid plaque pathology, and improve survival when given to a transgenic mouse model of human Alzheimer Disease during the nascent phase of A$\beta$ deposition.

As disclosed above, previous data suggested that some, but not all, inositol stereoisomers might have an effect on amyloid aggregation in cultured neuronal cells in vitro (McLaurin et al., *J. Biol. Chem.* 275(24): 18495-18502 (2000)). Those observations did not provide any method to predict which, if any, of the studied stereoisomers (myo-, epi-, scyllo- and chiro-inositols) would have such effects, nor whether any other stereoisomers would have such effects. Also, those studies could not predict if any inositol stereoisomers would have effects on amyloid deposition, cognitive defects or lifespan in vivo. The present invention describes the unpredictable results that only certain inositol stereoisomers, in particular scyllo- and allo-inositols reduce amyloid plaque burden, improve cognition and increase lifespan in animal models of amyloid-related disorders, whereas others studied did not have such effects.

Previous studies also suggested only that certain inositol stereoisomers (e.g. epi- and scyllo-inositols) might inhibit de novo amyloid aggregation in vitro. The present invention describes the unexpected results that scyllo-inositol inhibits already established cerebral amyloid deposition, and does so in the living brain. This is not implied by the previously published in vitro data which considered only certain neuronal cell types in culture, not the complex tissues of the living brain, and only suggested that inositols might inhibit de novo aggregation, thereby having no relevance to established disease.

Previous in vitro data also suggested that epi- and scyllo-inositol administration affects amyloid A$\beta$40 levels as well as Aβ42 levels. The in vivo dosing study of the present invention revealed the unpredictable result that administration of allo- or scyllo-inositol specifically reduced Aβ42 levels, whereas insoluble Aβ42 and either soluble or insoluble Aβ40 levels were unaffected.

The observation of the present invention showing changes in glial activity and inflammation is novel and surprising, and could not have been predicted by the in vitro data previously published.

The observation of the present invention demonstrating that scyllo-inositol improves lifespan in transgenic model animals is also novel and surprising, since no drug for Alzheimer's Disease has previously been shown to increase survival and extend lifespan in vivo.

Preferably, the compounds of the present invention are 1,2,3,4,5,6-cyclo-hexanehexols, more preferably selected from the group of cis-, epi-, allo-, muco-, neo-, scyllo-, D-chiro- and L-chiro-inositols.

Also preferably, these compounds are 1,2,3,4,5-cyclo-hexanepentols (quercitols), more preferably selected from the group of epi-, vibo-, scyllo-, allo-, talo-, gala-, cis-, muco-, neo-, proto-quercitols and enantiomers thereof.

Also preferably, these compounds are selected from the group of a cyclohexanetetrol, a cyclohexanetriol, stereoisomer of cyclohexanetetrol, stereoisimer of cyclohexanetriol, enantiomer of cyclohexanetetrol, and enantiomer of cyclohexanetriol.

These compounds may also be compound is pentahydxy-cyclohexanones or stereoisomers or enantiomers thereof.

Yet again preferably, these compounds are inosose compounds selected from the group of scyllo-inosose, L-chiro-inosose-1 and L-epi-inosose.

Also preferably, these compounds are trihydroxyxcyclohexanones, or stereoisomers or enantiomers thereof. More preferably, (–)-1-deoxy-scyllo-inosose.

Also preferably, these compounds are pentahydxycyclohexanones (inosose), or stereoisomers or enantiomers thereof, more preferably selected from the group of scyllo-inosose, L-chiro-inosose-1 and L-epi-inosose.

Optionally, these compounds are trihydroxyxcyclohexanones or stereoisomers or enantiomers thereof such as (–)-1-deoxy-scyllo-inosose.

Also preferably, these compounds are O-monomethyl-cyclohexanehexols or stereoisomers or enantiomers thereof; more preferably selected from the group of D-pinitol, L-quebrachitol and D-bornesitol.

Again, these compounds may be selected from the group of monoaminocyclohexanepentols (inosamines), diaminocyclohexanetetrols (inosadiamines), diaminocyclohexanetriols, stereoisomers thereof; and enantiomers thereof, and pharmaceutically acceptable salts thereof such as L-neo-inosamine, D,L-epi-inosamine-2, streptamine and deoxystreptamine.

Yet again preferably, these compounds are monomercapto-cyclohexanepentols or stereoisomers or enantiomers thereof, more preferably 1L-1-deoxy-1-mercapto-8-O-methyl-chiro-inositol.

The most preferred compounds of the present invention are allo-inositol and scyllo-inositol, with scyllo-inositol being the most preferred. As indicated above, the inositol stereoisomers of the present invention exclude myo-inositol and may also exclude epi-inositol.

Even when given after the amyloid pathology has been well established for several months, these compounds effectively reverse cerebral Aβ accumulation and amyloid pathology.

Accordingly, these compounds are found to be useful in treating or preventing in a subject a condition of the central or peripheral nervous system or systemic organ associated with a disorder in protein folding or aggregation, or amyloid formation, deposition, accumulation, or persistence. These compounds are also found to be useful in preventing abnormal protein folding, abnormal protein aggregation, amyloid formation, deposition, accumulation, or persistence, or amyloid lipid interactions as well as causing the dissociation of abnormally aggregated proteins and/or dissolving or disrupting pre-formed or pre-deposited amyloid fibril or amyloid in a subject.

Preferably, the condition of the central or peripheral nervous system or systemic organ results in the deposition of proteins, protein fragments and peptides in beta-pleated sheats and/or fibrils and/or aggregates. More preferably, the condition of the central or peripheral nervous system or systemic organ is selected from the group of: Alzheimer's disease, presenile and senile forms; amyloid angiopathy; mild cognitive impairment; Alzheimer's disease-related dementia; tauopathy; α-synucleinopathy; Parkinson's disease; Amyotrophic Lateral Sclerosis; motor neuron Disease; Spastic paraplagia; Huntington's Disease, spinocerebellar ataxia, Freidrich's Ataxia; neurodegenerative diseases associated with intracellular and/or intraneuronal aggregates of proteins with polyglutamine, polyalanine or other repeats arising from pathological expansions of tri- or tetra-nucleotide elements within corresponding genes; cerebrovascular diseases; Down's syndrome; head trauma with post-traumatic accumulation of amyloid beta peptide; Prion related disease; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy; Inclusion Body myositis due to amyloid beta peptide; Familial and Finnish Type Amyloidosis; Systemic amyloidosis associated with multiple myeloma; Familial Mediterranean Fever; chronic infections and inflammations; and Type II Diabetes Mellitus associate with islet amyloid polypeptide (IAPP).

Also preferably, the Alzheimer's disease-related dementias are vascular or Alzheimer dementia and tauopathy selected from the group of argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia.

Also preferably, the α-synucleinopathy is selected from the group of dementia with Lewy bodies, multiple system atrophy with glial cytoplasmic inclusions, Shy-Drager syndrome, striatonigral degeneration, olivopontocerebellar atrophy, neurodegeneration with brain iron accumulation type I, olfactory dysfunction, and amyotrophic lateral sclerosis.

Again preferably, the Motor Neuron Disease is associated with filaments and aggregates of neurofilament and/or superoxide dismutase proteins, the Spastic paraplegia is associated with defective function of chaperones and/or triple A proteins and the spinocerebellar ataxia is DRPLA or Machado-Joseph Disease.

Also preferably, the Prion related disease is selected from the group of Creutzfeldt-Jakob disease, Gerstmann-Straussler-Scheinker disease, and variant Creutzfeldt-Jakob disease and the Amyloid Polyneuropathy is Senile amyloid polyneuropathy or Systemic Amyloidosis.

More preferably, the condition of the central or peripheral nervous system or systemic organ is Parkinson's disease including familial and non-familial types. Most preferably, said condition of the central or peripheral nervous system or systemic organ is Alzheimer's disease.

Preferably, the compound is administered to the subject at a dose of about 1 mg to about 1 g per kg, preferably 1 mg to about 200 mg per kg, more preferably about 10 mg to about 100 mg per kg and most preferably about 30 mg to 70 mg per kg of the weight of said subject. The administration can be accomplished by a variety of ways such as orally (oral pill, oral liquid or suspension), intravenously, intramuscularly, intraperitoneally, intradermally, transcutaneously, subcutaneously, intranasally, sublingually, by rectal suppository or inhalation, with the oral administration being the most preferred. The administration of the compounds of the present invention can be undertaken at various intervals such as once a day, twice per day, once per week, once a month or continuously.

Preferably, the compounds of the present invention are administered in combination with other treatments such as beta-secretase inhibitors, gamma-secretase inhibitors (APP-specific or non-specific), epsilon-secretase inhibitors (APP-specific or non-specific), other inhibitors of beta-sheet aggregation/fibrillogenesis/ADDL formation (e.g. Alzhemed), NMDA antagonists (e.g. memantine), non-steroidal anti-inflammatory compounds (e.g. Ibuprofen, Celebrex), anti-oxidants (e.g. Vitamin E), hormones (e.g. estrogens), nutrients and food supplements (e.g. *Gingko biloba*); acetylcholinesterase inhibitors (e.g. donezepil), muscarinic agonists (e.g. AF102B (Cevimeline, EVOXAC). AF150(S), and AF267B), anti-psychotics (e.g. haloperidol, clozapine, olanzapine); anti-depressants including tricyclics and serotonin reuptake inhibitors (e.g. Sertraline and Citalopram Hbr), gene therapy and/or drug based approaches to upregulate neprilysin (an enzyme which degrades $A\beta$); gene therapy and/or drug based approaches to upregulate insulin degrading enzyme (an enzyme which degrades $A\beta$), vaccines, immunotherapeutics and antibodies to $A\beta$ (e.g. ELAN AN-1792), statins and other cholesterol lowering drugs (e.g. Lovastatin and Simvastatin), stem cell and other cell-based therapies, inhibitors of kinases (CDK5, GSK3$\alpha$, GSK3$\beta$) that phosphorylate TAU protein (e.g. Lithium chloride), or inhibitors of kinases that modulate AR production (GSK3$\alpha$, GSK3$\beta$, Rho/ROCK kinases) (e.g. lithium Chloride and Ibuprofen).

It is believed that these other therapies act via a different mechanism and may have additive/synergistic effects with the present invention. In addition, many of these other therapies will have mechanism-based and/or other side effects which limit the dose or duration at which they can be administered alone.

Because of their ability to bind amyloids in vivo as discussed hereinbelow in more detail, the compounds of the present invention are also useful in diagnosing the presence of abnormally folded or aggregated protein and/or amyloid fibril or amyloid in a subject using a method that comprises administering to said subject a radioactive compound or compound tagged with a substance that emits a detectable signal in a quantity sufficient and under conditions to allow for the binding of said compound to the abnormally folded or aggregated protein and/or fibrils or amyloid, if present; and detecting the radioactivity or the signal from the compound bound to the abnormally folded or aggregated protein and/or fibrils or amyloid or amyloid, thus diagnosing the presence of abnormally folded or aggregated protein and/or amyloid fibril or amyloid.

Alternatively, a sample suspected of containing abnormally folded or aggregated protein and/or amyloid fibril or amyloid is collected from a subject and is contacted with a radioactive compound or compound tagged with a substance that emits a detectable signal under conditions to allow the binding of said compound to the abnormally folded or aggregated protein and/or amyloid fibril or amyloid if present; and thereafter detect the radioactivity or the signal from the compound bound to the abnormally folded or aggregated protein and/or fibrils or amyloid, thus diagnosing the presence of abnormally folded or aggregated protein and/or amyloid fibril or amyloid in said subject.

Preferably, said detectable signal is a fluorescent or an enzyme-linked immunosorbent assay signal and said sample is whole blood (including all cellular constituents) or plasma.

As shown hereinbelow, the compounds of the present invention can abrogate the cerebral accumulation of $A\beta$, the deposition of cerebral amyloid plaques, and cognitive decline in a transgenic mouse model of Alzheimer Disease when given during the "late presymptomatic" phase, prior to the onset of overt cognitive deficits and amyloid neuropathology in these mice. Furthermore, even when these compounds are given after the onset of cognitive deficits and amyloid plaque neuropathology, they can effectively reverse the amyloid deposition and neuropathology. Importantly, the mechanism of action of these compounds follows a rational design based upon their capacity to modulate the assembly of $A\beta$ monomers into neurotoxic oligomers and/or protofibrils.

Other advantages of the compounds of the present invention include the fact that they are transported into the CNS by both known transporters and by passive diffusion, and therefore provide ready CNS bioavailablility. Second, these compounds are catabolized to glucose. Third, as a class, these compounds generally have low toxicity profiles, and some of them have previously been given to humans albeit for a different purpose.

Example 1—Development of Alzheimer's Mouse Model and Methods of Administering Compounds of the Present Invention TgCRND8 mice are a robust murine model of Alzheimer's disease as described by Janus et al. (*Nature* 408:979-982 (2000). They express a human amyloid precursor protein (APP695) transgene under the regulation of the Syrian hamster prion promoter on a C3H/B6 outbred background. The human APP695 transgene bears two mutations that cause AD in humans (K670N/M671 L and V717F). Beginning at about 3 months of age, TgCRND8 mice have progressive spatial learning deficits that are accompanied by rising cerebral $A\beta$ levels and by increasing number of cerebral extracellular amyloid plaques that are similar to those seen in the brains of humans with AD (C. Janus et al., *Nature* 408:979-982 (2000)).

Age and sex-matched cohorts of TgCRND8 mice and non-transgenic littermates (n=35 in each cohort) were either untreated, or were given a compound of the present invention as indicated below at 30 mg/day/mouse beginning at age of about 6 weeks. The mice were followed for outcome measures cognitive function, brain Aβ levels, brain pathology, and survival at 4 months and 6 months of age.

Prevention Studies Methods

Mice—

Experimental groups of TgCRND8 mice were fed myo-, epi- and scyllo-inositol at 30 mg/mouse/day. Two cohorts entered the study at 6 weeks of age and outcomes were analyzed at 4- and 6-months of age. The body weight, coat characteristics and in cage behavior was monitored. All experiments were performed according to the Canadian Council on Animal Care guidelines.

Behavioral Tests—

After non-spatial pre-training, mice underwent place discrimination training for 5 days with 4 trials per day. Behavioral data was analyzed using a mixed model of factorial analysis of variance (ANOVA) with drug or genotype and training sessions as repeated measure factors.

Cerebral Amyloid Burden—

Brains were removed and one hemisphere was fixed in 4% paraformaldehyde and embedded in paraffin wax in the mid saggital plane. To generate sets of systematic uniform random sections, 5 μm serial sections were collected across the entire hemisphere. Sets of sections at 50 mm intervals were used for analyses (10-14 sections/set). Plaque were identified after antigen retrieval with formic acid, and incubated with primary anti-Aβ antibody (Dako M-0872), followed by secondary antibody (Dako StreptABCcomplex/horseradish kit). End products were visualized with DAB counter-stained with hematoxylin. Amyloid plaque burden was assessed using Leco IA-3001 image analysis software interfaced with Leica microscope and Hitachi KP-M1U CCD video camera. Vascular burden was analyzed similarly and a dissector was used to measure the diameter of affected vessels.

Plasma and Cerebral AD Content—

Hemi-brain samples were homogenized in a buffered sucrose solution, followed by either 0.4% diethylamine/100 mM NaCl for soluble Aβ levels or cold formic acid for the isolation of total Aβ. After neutralization the samples were diluted and analyzed for Aβ40 and Aβ42 using commercially available kits (BIOSOURCE International). Each hemisphere was analyzed in triplicate with the mean±SEM reported. Western blot analyses were performed on all fractions using urea gels for Aβ species analyses. Aβ was detected using 6E10 (BIOSOURCE International) and Enhanced Chemiluminenscence (Amersham).

Analysis of APP in Brain—

Mouse hemi-brain samples were homogenized in 20 mM Tris pH7.4, 0.25M sucrose, 1 mM EDTA and 1 mM EGTA, and a protease inhibitor cocktail, mixed with 0.4% DEA (diethylamine)/100 mM NaCl and spun at 109,000×g. The supernatants were analysed for APPs levels by Western blotting using mAb 22C11, while the pellets were analysed for APP holoprotein using mAb C1/6.1.

Gliosis Quantitation—

Five randomly selected, evenly spaced, sagittal sections were collected from paraformaldehyde-fixed and frozen hemispheres of treated and control mice. Sections were immunolabelled for astrocytes with anti-rat GFAP IgG2a (Dako; diluted 1:50) and for microglia with anti-rat CD68 IgG2b (Dako; 1:50). Digital images were captured using a Coolsnap digital camera (Photometrics. Tucson, Ariz.) mounted to a Zeiss Axioscope 2 Plus microscope. Images were analysed using Openlab 3.08 imaging software (Improvision, Lexington Mass.).

Survival Census—

The probability of survival was assessed by the Kaplan-Meier technique, computing the probability of survival at every occurrence of death, thus making it suitable for small sample sizes. For the analyses of survival, 35 mice were used for each treatment group. The comparison between treatments was reported using the Tarone-Ware test.

Example 2—Prevention of Cognitive Deficits

Figure 1A:
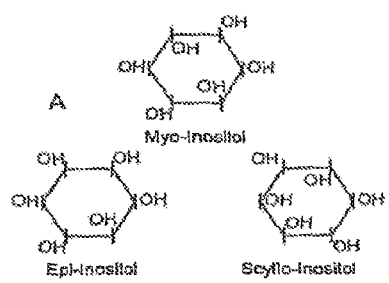
Figure 1B:
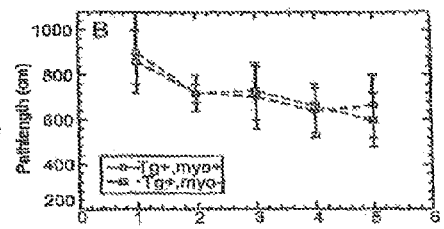
FIGS. 1B-1H show the spatial reference memory version of the Morris water maze test in TgCRND8 mice. Myo-inositol treatment did not alter cognitive function (1B). At 6 months of age, non-treated TgCRND8 (n=10) show cognitive impairment relative to non-Tg controls and epi- (1C) and scyllo-inositol (1D) treated mice (n=10 per group, p<0.02 untreated vs. treated). The performance of epi-inositol treated TgCRND8 mice remained impaired with respect to non-Tg littermates (1E) whereas the performance of scyllo-inositol TgCRND8 approached that of non-Tg littermates (1F). Non-Tg littermate behavior was not effected by either epi- (1G) or scyllo-inositol (1H) treatment. Vertical bars represent S.E.M.
Figure 1C:
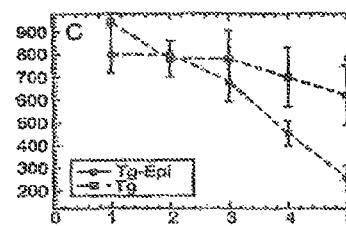
Figure 1D:
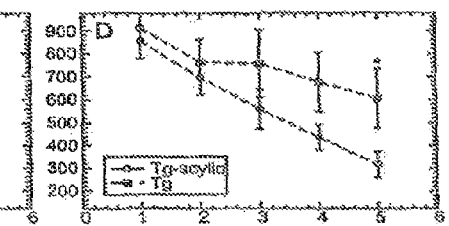
Figure 1E:
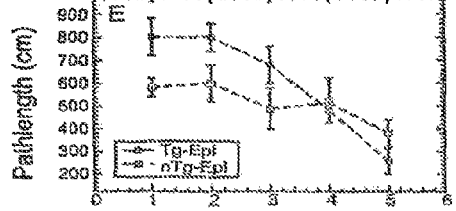
Figure 1F:
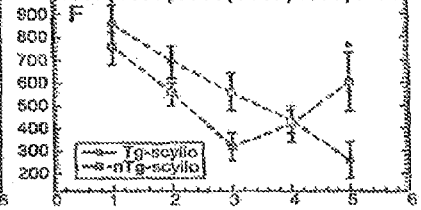
Figure 1G:
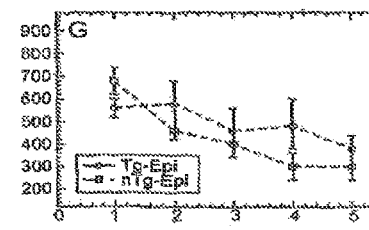
Figure 1H:
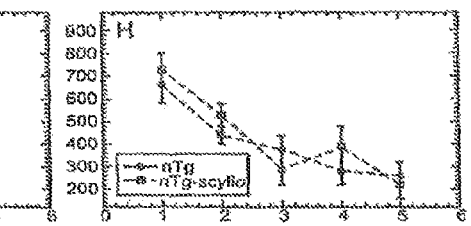

The cognitive function of TgCRND8 mice was assessed using the spatial reference memory version of the Morris Water Maze using a five-day trial paradigm (FIGS. 1C-1H). Data from treated and non-treated TgCRND8 mice, and from treated and non-treated non-Tg littermates (n=10 for all combinations) were analyzed using a mixed model of analysis of variance (ANOVA) with treatment (untreated, epi- or scyllo-inositol) and genotype (TgCRND8 versus non-Tg) as 'between-subject' factors. TgCRND8 mice treated with either epi- or scyllo-inositol performed significantly better than untreated TgCRND8 mice ($p<0.02$; FIGS. 1C and D). When compared to treated or non-treated non-Tg littermates, epi-inositol treated TgCRND8 mice had a slightly slower learning curve during the first three days of training. However, after 4 days of training, epi-inositol treated TgCRND8 mice were not statistically different from their non-Tg littermates (FIG. 2E). In contrast, scyllo-inositol treated TgCRND8 mice were indistinguishable from non-Tg littermates on all days. Thus both stereoisomers inhibited the development of cognitive deficits, and scyllo-inositol actually prevented the deficits to such a degree that the scyllo-inositol treated TgCRND8 mice were indistinguishable from normal mice. This improved performance was not due to a non-specific effect on behavioral, motoric, or perceptual systems because epi- and scyllo-inositol treatment had no effect on the performance of non-Tg mice (FIGS. 2G and 2H). The improved performance was also not due to nutritional or caloric effects because body weight, activity, and coat condition were not different between treated and untreated cohorts. Furthermore, treatment with mannitol (a sugar of similar molecular weight) had no effect on behavior. Gender effects were not significant between any treatment group ($p=0.85$).

Example 3—Reduction of Cerebral Aβ Burden and Amyloid Neuropathology

At four months of age, untreated TgCRND8 mice have a robust expression of both Aβ40 and Aβ42 (Table 1). Epi-inositol treatment as described in Example 1 reduced both Aβ40 (43±12% reduction in both soluble and insoluble pools; p0.0.05) and Aβ42 levels (69% reduction in soluble pool, $p=0.005$; 28% reduction in insoluble pool, $p=0.02$) at 4-months of age. However, these improvements were not sustained, and by 6 months of age, brain Aβ levels rose to levels similar to those observed in untreated TgCRND8 mice (Table 1).

In contrast, at four months of age, scyllo-inositol treatment decreased total brain Aβ40 by 62% ($p=0.0002$) and total brain Aβ42 by 22% ($p=0.0096$; Table 1). At 6 months of age, scyllo-inositol treatment caused a 32% reduction in Aβ40 levels ($p=0.04$) and 20% reduction in Aβ42 ($p=0.02$) compared to untreated TgCRND8 mice.

Because the decreased Aβ concentrations detected after inositol treatment could have resulted from altered efflux of Aβ into the plasma, Aβ-β levels in the plasma were examined at 4- and 6-months of age (Table 1). TgCRND8 mice have high plasma Aβ concentrations at 4-months of age and remain constant at 6 months of age even though CNS plaque load is still rising at 6-months of age (Table 1). Neither epi-inositol nor scyllo-inositol treatment had any effect on plasma Aβ levels in comparison to untreated TgCRND8 mice (p=0.89). The most parsimonious explanation for this observation is that the inositols have selectively altered the fibrillization of Aβ in the CNS, but have not affected β- or γ-secretase activity, or the normal mechanisms for clearance of Aβ into plasma. Nevertheless, this observation is significant for two reasons. First, a drop in plasma and CSF Aβ levels is usually detected as the clinical course progresses in untreated Aβ patients (Mayeux, et al., *Ann. Neurol* 46, 412, that at modest Aβ levels, epi-inositol prevents Aβ oligomerization but once initiated at higher Aβ concentrations, epi-inositol is unable to inhibit fibrillogenesis. Scyllo-inositol treatment decreased the mean plaque size from $136\pm15$ $\mu m^2$ to $103\pm4$ $\mu m^2$ (p=0.01) at 4 months of age. In scyllo-inositol treated TgCRND8 mice at 6 months of age, the decrease in Aβ peptide levels was accompanied by a 20% reduction in plaque number (p=0.005), a 35% decrease in brain area covered with plaques (p=0.015) and a decreased mean plaque size ($339\pm10$ vs. $423\pm21$ $\mu m^2$, p=0.009). These results demonstrate that by every measure there was a reduction in plaque burden after scyllo-inositol treatment.

TABLE 1

Inositol treatment decreases Aβ40 and Aβ42 Levels

| | Aβ40 (ng/gm wet brain ± sem) | | Aβ42 (ng/gm wet brain ± sem) | | Total Aβ | Plaque Count | Plaque Area ($\mu m^2$) | Total Plaque Area/Total Brain Area (%) |
|---|---|---|---|---|---|---|---|---|
| | Soluble | Insoluble | Soluble | Insoluble | | | | |
| 4 month prevention | | | | | | | | |
| Control | 75 ± 6 | 1163 ± 9 | 273 ± 18 | 5658 ± 248 | 7169 ± 284 | 696 ± 25 | 100766 ± 7564 | 0.026 ± 0.004 |
| Epi-Inositol | 43 ± 7* | 615 ± 32† | 85 ± 7† | 4059 ± 179* | 4802 ± 176 | 678 ± 64 | 65042 ± 5199 | 0.020 ± 0.001 |
| Scyllo-Inositol | 37 ± 5* | 437 ± 80† | 206 ± 8* | 4409 ± 135* | 5089 ± 173 | 598 ± 19* | 63847 ± 2895 | 0.015 ± 0.001* |
| 6 month prevention | | | | | | | | |
| Control | 187 ± 29 | 3576 ± 172 | 626 ± 87 | 15802 ± 237 | 20191 ± 211 | 960 ± 44 | 411288 ± 11912 | 0.120 ± 0.001 |
| Epi-Inositol | 188 ± 24 | 3668 ± 149 | 665 ± 39 | 13943 ± 277† | 18464 ± 229 | 979 ± 32 | 380456 ± 13498 | 0.096 ± 0.04 |
| Scyllo-Inositol | 105 ± 8* | 2453 ± 251*† | 475 ± 26* | 12588 ± 82† | 15621 ± 151 | 774 ± 10*† | 262379 ± 5373† | 0.079 ± 0.013† |

| Plasma Aβ Levels (pg/ml) | | |
|---|---|---|
| | 4 month prevention | 6 month prevention |
| Control | 1018 ± 27 | 915 ± 59 |
| Epi-Inositol | 1082 ± 164 | 952 ± 56 |
| Scyllo-Inositol | 952 ± 49 | 905 ± 55 |

Anova with Fisher's PLSD,
†p < 0.001 and
*p < 0.05

2001). Secondly, patients in the AN1792 immunization study who developed a strong antibody response and an apparent clinical response did not have altered plasma Aβ-β levels (Hock et al., Neuron 38, 547 2003). Therefore, these results indicate that it is not necessary to change plasma Aβ levels to obtain an effective therapeutic outcome.

To confirm that inositol stereoisomers had no effect on either the expression or proteolytic processing of APP, the levels of APP holo-protein, sAPP-α, and various Aβ species were examined within the brain of inositol-treated and untreated TgCRND8 mice. Consistent with our previously reported data (McLaurin, et al., *Nat. Med.* 8, 1263, 2002), Aβ42, Aβ40 and Aβ38 are the predominant species in the brain of TgCRND8 mice (FIG. 3A), and the CNS levels of immature and mature glycolyslated APP (FIG. 3B), and of sAPP-α were indistinguishable regardless of treatment. In combination, these results indicate that epi- and scyllo-inositol have a direct and selective effect on Aβ oligomerization and not the processing of APP.

The changes in Aβ-β peptide load were accompanied by a significant decrease in plaque burden (Table 1; FIGS. 2A-2I). In epi-inositol treated TgCRND8 mice, there was a significant decrease in the mean plaque size at 4- but not 6-months of age compared with untreated TgCRND8 mice ($95\pm4.3$ $\mu m^2$ versus $136\pm15$ $\mu m^2$, p=0.04; $370\pm9$ $\mu m^2$ versus $423\pm221\mu^2$, p=0.06, respectively). These results indicate Example 4—Reduction of Glial Reactivity and Inflammation Astroglial and microglial reactions are neuropathological features both of human AD and of all amyloid mouse models (Irizarry et al., *J Neuropathol Exp Neurol.* 56, 965, 1997; K. D. Bornemann et al. *Ann N Y Acad Sci.* 908, 260, 2000). Therefore, the effect of epi- and scyllo-inositol treatment was investigated on astrogliosis and microgliosis in the brains of TgCRND8 mice (FIGS. 3A-3D). Serial sagittal sections were stained with the astrocytic marker glial fibrillary acidic protein (GFAP) and quantitated for percent brain area covered by astrogliosis. TgCRND8 mice have a high basal astrogliosis at 4-months of age ($0.459\pm0.048\%$), which increases slightly by 6-months of age ($0.584\pm0.089\%$), and which is not restricted to plaque areas (FIGS. 2A-C). Epi-inositol decreased the astrogliotic response to $0.388\pm0.039\%$ at 6-months of age (p=0.04; FIG. 2D-F). Scyllo-inositol, on the other hand, decreased astrogliosis much more efficiently to $0.269\pm0.028\%$ at 6-months of age, (p:=0.006) (FIG. 2G-I). Microglial activation was also significantly attenuated in scyllo-inositol treated TgCRND8 mice ($0.20\pm0.008\%$ brain area) when compared to age- and sex-matched untreated TgCRND8 mice ($0.31\pm0.01\%$; p<0.001). However, epi-inositol treated mice demonstrated no significant reduction in microglial activation at 6 months (0.248±0.02%; p=NS). Taken together these data indicate that scyllo-inositol treatment decreases the Aβ-induced inflammatory response within the CNS.

Example 5—Reduction of Vascular Amyloid Load

Alzheimer's disease is characterized by the presence of both parenchymal and vascular amyloid deposits. In untreated 6 month old TgCRND8 mice approximately 0.03% of the brain area is associated with vascular amyloid. No difference could be detected in the vascular amyloid burden after epi-inositol treatment at 6 months of age (FIG. 3C). In contrast, scyllo-inositol treatment significantly decreased the vascular amyloid burden (p=0.05) (FIG. 3C), and the amyloid deposition was predominantly localized to smaller vessels, <25 m$^2$ in diameter (56±2% versus 70±8% in small vessels in untreated TgCRND8 mice). The mean size of cerebrovascular plaques was significantly decreased in the scyllo-inositol treated mice in comparison to untreated mice (154.416 vs. 363±34, p=0.008; FIG. 3D).

Example 6—Survival Improvement

TgCRND8 mice have a 50% survival at 175 days, which after treatment was improved to 72% with scyllo-inositol (n=35 per group, p<0.02 for scyllo-inositol vs. control, FIG. 10B). Treatment with myo-inositol did not affect overall survival significantly (FIG. 10A). Control experiments confirmed that the enhanced survival of scyllo-inositol treated mice was not an indirect effect of increased caloric intake. Thus, treatment of wild type mice with scyllo-inositol had no effect either on survival or on other parameters such as weight, fur condition or cage behavior. Furthermore, the weight, fur condition and home-cage behavior of the inositol-treated TgCRND8 mice did not vary from untreated TgCRND8 mice. Simultaneous experiments with mannitol, a simple sugar of similar molecular weight, also had no effect on survival of TgCRND8 mice.

Example 7—Treatment and Reversal of Amyloid Deposition

Taken together, the prevention studies demonstrate that scyllo-inositol inhibits both parenchymal and cerebrovascular amyloid deposition and results in improved survival and cognitive function in the TgCRND8 mouse model of Alzheimer disease. However, most Alzheimer's disease patients will likely seek treatment only once symptomatic, and when Aβ oligomerization, deposition, toxicity and plaque formation are already well advanced within the CNS. A pilot study was therefore initiated on 5 month old TgCRND8 mice. These mice have significant Aβ and plaque burdens that are comparable to those in the brain of humans with AD.

Treatment Study Methods
Mice—
Experimental groups of TgCRND8 mice were fed myo-, epi- and scyllo-inositol at 30 mg/mouse/day. A cohort entered the study at 5 months of age and outcomes were analyzed at 6-months of age. The body weight, coat characteristics and in cage behavior was monitored. All experiments were performed according to the Canadian Council on Animal Care guidelines.

Survival Census—
The probability of survival was assessed by the Kaplan-Meier technique, computing the probability of survival at every occurrence of death, thus making it suitable for small sample sizes. For the analyses of survival, 35 mice were used for each treatment group. The comparison between treatments was reported using the Tarone-Ware test.

Behavioral Test—
Reversal Study—Mice entered the Morris water maze test with a hidden platform on day one without pretraining. Mice were tested for 3 days with six trials per day. On the fourth day, the platform was removed from the pool and each mouse received one 30-s swim probe trial. On the last day the animals underwent a cue test in order to evaluate swimming ability, eye sight and general cognition. The cue test is composed at the platform being placed in a different quadrant than that used for testing and is tagged with a flag. Animals are allowed 60 s to find the platform. Animals that do not find the platform are not used in the final analyses of spatial memory. Behavioural data was analysed using a mixed model of factorial analysis of variance (ANOVA) with drug or genotype and training sessions as repeated measure factors.

Cerebral Amyloid Burden—
Brains were removed and one hemisphere was fixed in 4% paraformaldehyde and embedded in paraffin wax in the mid saggital plane. To generate sets of systematic uniform random sections, 5 μm serial sections were collected across the entire hemisphere. Sets of sections at 50 mm intervals were used for analyses (10-14 sections/set). Plaque were identified after antigen retrieval with formic acid, and incubated with primary anti-Aβ antibody (Dako M-0872), followed by secondary antibody (Dako StreptABCcomplex/ horseradish kit). End products were visualized with DAB counter-stained with hematoxylin. Amyloid plaque burden was assessed using Leco IA-3001 image analysis software interfaced with Leica microscope and Hitachi KP-M1U CCD video camera.

Plasma and Cerebral Aβ Content—
Hemi-brain samples were homogenized in a buffered sucrose solution, followed by either 0.4% diethylamine/100 mM NaCl for soluble Aβ levels or cold formic acid for the isolation of total Aβ. After neutralization the samples were diluted and analyzed for Aβ40 and Aβ42 using commercially available kits (BIOSOURCE International). Each hemisphere was analyzed in triplicate with the mean±SEM reported.

Results and Significance—
All animals that entered the reversal study survived and did not display outward signs of distress or toxicity. The cognitive function of TgCRND8 mice was assessed using the spatial reference memory version of the Morris Water Maze using a three day trial paradigm (FIGS. 4-8). Data from treated and non-treated TgCRND8 mice, and from treated and non-treated non-Tg littermates (n=10 for all combinations) were analyzed using a mixed model of analysis of variance (ANOVA) with treatment (untreated, myo-, epi- or scyllo-inositol) and genotype (TgCRND8 versus non-Tg) as 'between-subject' factors. In this paradigm TgCRND8 mice were significantly impaired in comparison to wild type littermates (FIG. 4). In contrast, scyllo-inositol treated TgCRND8 mice were indistinguishable from non-Tg littermates on all days. (p=0.38; FIG. 5). When compared to treated non-Tg littermates, epi-inositol treated TgCRND8 mice were almost significantly different (p=0.07; FIG. 6). Similarly, myo-inositol treated TgCRND8 mice were significantly different from treated non-Tg littermates (p=0.05. FIG. 7). When the learning phase of the Morris water maze test is compared between treatments, all mice behaved similarly (FIG. 8). In contrast, only scyllo-inositol was indistinguishable from non-Tg littermates (FIG. 8). Thus, scyllo-inositol actually reversed the cognitive deficits to such a degree that the scyllo-inositol treated TgCRND8 mice were indistinguishable from normal mice. This improved performance was not due to a non-specific effect on behavioral, motoric, or perceptual systems because epi- and scyllo-inositol treatment had no effect on the performance of non-Tg mice. The improved performance was also not due to nutritional or caloric effects because body weight, activity, and coat condition were not different between treated and untreated cohorts.

In order to determine if the improved cognition was associated with decreased plaque burden and Aβ load, brain tissue was examined post-mortem. The changes in cognition were accompanied by a corresponding change in plaque burden and Aβ load (FIG. 9 and Table 2). Myo-inositol treatment did not affect the plaque burden or Aβ load (FIG. 9 and Table 2). In epi-inositol treated TgCRND8 mice, there was not a significant decrease in the mean plaque size compared with untreated TgCRND8 mice (FIG. 9), yet the Aβ load was significantly decreased (Table 2). These results suggest that at modest Aβ levels, epi-inositol prevents Aβ oligomerization but at higher Aβ concentrations, epi-inositol is unable to inhibit fibrillogenesis completely. Scyllo-inositol treatment significantly decreased the plaque burden and the Aβ load. These results demonstrate that by every measure there was a reduction in plaque burden after scyllo-inositol treatment. These results are comparable in effect size to the 6-month prophylactic studies, and further support the potential for scyllo-inositol.

Because the decreased Aβ concentrations detected after inositol treatment could have resulted from altered efflux of Aβ into the plasma, we examined Aβ levels in the plasma (Table 2). TgCRND8 mice have high plasma Aβ concentrations at 6 months of age. Neither myo-inositol, epi-inositol nor scyllo-inositol treatment had any effect on plasma Aβ levels in comparison to untreated TgCRND8 mice (p=0.89). The most parsimonious explanation for this observation is that the inositols have selectively altered the fibrillization of Aβ in the CNS, but have not affected β- or γ-secretase activity, or the normal mechanisms for clearance of Aβ into plasma. Nevertheless, this observation is significant for two reasons. First, a drop in plasma and CSF Aβ levels is usually detected as the clinical course progresses in untreated AD patients. Secondly, patients in the AN1792 immunization study who developed a strong antibody response and an apparent clinical response did not have altered plasma Aβ levels. Therefore, these results further indicate that it is not necessary to change plasma Aβ levels to obtain an effective therapeutic outcome.

Taken together, these data reveal that selected scyllo-inositol can abrogate the cerebral accumulation of Aβ, the deposition of cerebral amyloid plaques, and cognitive decline in a transgenic mouse model of Alzheimer Disease when given during the "late presymptomatic" phase, prior to the onset of overt cognitive deficits and amyloid neuropathology in these mice. Furthermore, even when scyllo-inositol is given after the onset of cognitive deficits and amyloid plaque neuropathology, these compounds can effectively reverse the amyloid deposition, neuropathology and cognitive deficits. Therefore, these results indicate that scyllo-inositol is effective at both prevention of disease and in the treatment of existing disease in patients already diagnosed with AD.

TABLE 2

Inositol treatment decreases Aβ40 and Aβ42 Levels

| | Aβ40 (ng/gm wet brain ± sem) | | Aβ42 (ng/gm wet brain ± sem) | | Total | Plaque | Plaque | Total Plaque Area/Total |
|---|---|---|---|---|---|---|---|---|
| | Soluble | Insoluble | Soluble | Insoluble | Aβ | Count | Area ($\mu m^2$) | Brain Area (%) |
| | | | | 4 month prevention | | | | |
| Control | 75 ± 6 | 1163 ± 9 | 273 ± 18 | 5658 ± 248 | 7169 ± 284 | 696 ± 25 | 100766 ± 7564 | 0.026 ± 0.004 |
| Myo-Inositol | 42 ± 6 | 485 ± 143 | 174 ± 9 | 4268 ± 308 | 4969 ± 434 | 649 ± 50 | 91902 ± 7453 | 0.023 ± 0.004 |
| Epi-Inositol | 43 ± 7* | 615 ± 32† | 85 ± 7† | 4059 ± 179* | 4802 ± 176 | 678 ± 64 | 65042 ± 5199 | 0.020 ± 0.001 |
| Scyllo-Inositol | 37 ± 5* | 437 ± 80† | 206 ± 8* | 4409 ± 135* | 5089 ± 173 | 598 ± 19* | 63847 ± 2895 | 0.015 ± 0.001* |
| | | | | 6 month prevention | | | | |
| Control | 187 ± 29 | 3576 ± 172 | 626 ± 87 | 15802 ± 237 | 20191 ± 211 | 960 ± 44 | 411288 ± 11912 | 0.120 ± 0.001 |
| Myo-Inositol | 221 ± 19 | 3436 ± 189 | 543 ± 71 | 13219 ± 535 | 17489 ± 354 | 927 ± 78 | 400013 ± 19638 | 0.100 ± 0.005 |
| Epi-Inositol | 188 ± 24 | 3668 ± 149 | 665 ± 39 | 13943 ± 277† | 18464 ± 229 | 979 ± 32 | 380456 ± 13498 | 0.096 ± 0.04 |
| Scyllo-Inositol | 105 ± 8* | 2453 ± 251*† | 475 ± 26* | 12588 ± 82† | 15621 ± 151 | 774 ± 10*† | 262379 ± 5373† | 0.079 ± 0.013† |
| | | | | 1 month treatment | | | | |
| Control | 207 ± 16 | 4965 ± 457 | 426 ± 14 | 14503 ± 1071 | 20101 ± 854 | 1441 ± 29 | 486002 ± 16156 | 0.159 ± 0.014 |
| Myo-Inositol | 194 ± 12 | 4187 ± 226 | 487 ± 25 | 15622 ± 675 | 20490 ± 526 | 1324 ± 69 | 469968 ± 35664 | 0.153 ± 0.088 |
| Epi-Inositol | 264 ± 11 | 3637 ± 113 | 540 ± 14 | 12830 ± 330 | 17271 ± 415 | 1342 ± 114 | 459706 ± 49966 | 0.134 ± 0.017 |
| Scyllo-Inositol | 178 ± 11 | 3527 ± 241 | 374 ± 23 | 11115 ± 647 | 15194 ± 579 | 1260 ± 27* | 420027 ± 14986* | 0.119 ± 0.010* |

| Plasma Aβ Levels (pg/ml) | | | |
|---|---|---|---|
| | 4 month prevention | 6 month prevention | 1 month treatment |
| Control | 1018 ± 27 | 915 ± 59 | 2287 ± 151 |
| Myo-Inositol | 942 ± 30 | 969 ± 67 | 2110 ± 174 |
| Epi-Inositol | 1082 ± 164 | 952 ± 56 | 2158 ± 157 |
| Scyllo-Inositol | 952 ± 49 | 905 ± 55 | 1980 ± 146 |

Anova with Fisher's PLSD,
†p < 0.001 and
*p < 0.05; IP = in progress.

Example 8—Two-Month Treatment Study with Scyllo-Inositol

In order to determine longer efficacy ranges of scyllo-inositol for the treatment of disease, 5-month old TgCRND8 mice were fed scyllo-inositol or untreated for two months (n=10 per group). The cognitive function of 7-month old TgCRND8 mice treated with scyllo-inositol was compared to untreated TgCRND8 and treated non-Tg littermates in the three-day paradigm of the Morris Water Maze. Behavioural data was analysed using a mixed model of factorial analysis of variance (ANOVA) with drug and genotype as between subject variables and training sessions as within subject variable. As was seen with the 1-month treatment of scyllo-inositol (FIG. 12A), TgCRND8 mice treated for two months with scyllo-inositol were indistinguishable from scyllo-inositol treated non-Tg littermates (FIG. 12B). In order to correlate the improved cognition with pathology, Aβ40 and Aβ42 levels were analysed in the brain (Table 3). Both insoluble Aβ40 and Aβ42 levels were decreased 20% after scyllo-inositol treatment. These results demonstrate that scyllo-inositol effects persist during disease progression.

Example 10—Efficacy of Allo-Inositol for the Treatment of Disease Bearing TgCRND8 Mice To assess whether allo-inositol might also be effective in preventing further progression and/or might partially reverse a well-established AD-like phenotype, the start of treatment of the TgCRND8 mice was delayed until 5 months of age. Cohorts of TgCRND8 and non-transgenic littermates were either treated for 28 days with allo-inositol, or were untreated. In these experiments, the dosage and oral administration of compounds, and the behavioral and neurochemical assays were the same as those employed in the above treatment experiments.

The cohort of 6-month old allo-inositol-treated TgCRND8 mice performed significantly better than untreated TgCRND8 mice ($F_{1,13}$=0.45, p=0.05; data not shown). The cognitive performance of 6-month old allo-inositol-treated TgCRND8 mice was still significantly different from that of their non-transgenic littermates ($F_{1,13}$=5.9, p=0.05; FIG. 15). The beneficial effect of inositol treatment was not due to non-specific effects on behavioral, motor, or perceptual systems because inositol treatment had no effect on the cognitive performance of non-Tg mice ($F_{1,12}$=0.98; p=0.49). Cerebral Aβ levels were analyzed for treated versus untreated TgCRND8 mice to determine whether improved behavior could be correlated with changes in Aβ (Table 4). Allo-inositol treatment reduced soluble Aβ42 (20% reduction, p<0.05) an effect similar to that seen for scyllo-inositol. Allo-inositol did not significantly alter insoluble Aβ42 or Aβ40 (soluble and insoluble pools). One possible explanation for the decrease in Aβ42 is clearance of Aβ42 in the periphery with a subsequent increase in plasma Aβ42. The levels of Aβ42 in plasma after allo-inositol treatment were indistinguishable from untreated TgCRND8 plasma levels (Table 5). In agreement with the other inositol stereoisomers, these results demonstrate that plasma Aβ levels are unaffected by allo-inositol treatment.

TABLE 3

Inositol treatment decreases Aβ40 and Aβ42 Levels

| | Brain Aβ40 (ng/gm wet brain ± sem) | | Brain Aβ42 (ng/gm wet brain ± sem) | | Plasma Aβ Levels (pg/ml) | |
|---|---|---|---|---|---|---|
| | Soluble | Insoluble | Soluble | Insoluble | Aβ40 | Aβ42 |
| | | | 2 month treatment | | | |
| Control | 487 ± 14 | 6924 ± 287 | 764 ± 51 | 25827 ± 1238 | 5212 ± 219 | 3455 ± 331 |
| Scyllo-inositol | 395 ± 60 | 5703 ± 612* | 688 ± 28 | 20818 ± 1404* | 4507 ± 207 | 3035 ± 236 |

ANOVA with Fisher's PLSD,
*p < 0.05.

Example 9—Effect of Dose on Pathological Outcome in Disease Bearing TgCRND8 Mice 5-month old TgCRND8 mice were gavaged once daily with scyllo-inositol in water at doses of 10 mg/Kg, 30 mg/Kg, 100 mg/Kg or untreated. Animals were sacrificed after one month of treatment and analysed for pathological outcomes. Analysis of the levels of Aβ within the brain of all the cohorts demonstrates that all drug doses were effective to the same extent on lowering soluble Aβ42 levels in comparison to untreated TgCRND8 mice (20% reduction, $F_{3,15}$=3.1, p=0.07; FIG. 13A). Analyses of individual doses demonstrate that 10 mg/Kg and 30 mg/Kg doses were significantly different from untreated controls (p=0.03 and p=0.02, respectively). None of the doses chosen were significantly different from each other ($F_{2,11}$=0.6, p=0.57; FIG. 13A). Gavage dosing had no significant effect on insoluble Aβ42 ($F_{3,15}$=0.69, p=0.58; FIG. 13B) or soluble and insoluble Aβ40 ($F_{3,15}$=0.04, p=0.99 and $F_{3,15}$=0.36, p=0.79, respectively; FIGS. 14A and 14B).

TABLE 4

Allo-Inositol treatment decreases Aβ42 levels

| | Brain Aβ40 (ng/gm wet brain ± sem) | | Brain Aβ42 (ng/gm wet brain ± sem) | | Plasma Aβ Levels (pg/ml) |
|---|---|---|---|---|---|
| | Soluble | Insoluble | Soluble | Insoluble | |
| 1 month treatment | | | | | |
| Control | 252 ± 48 | 4105 ± 851 | 666 ± 39 | 16448 ± 2120 | 2359 ± 147 |
| Allo-inositol | 281 ± 21 | 3787 ± 342 | 547 ± 47* | 16336 ± 910 | 2458 ± 95 |

ANOVA with Fisher's PLSD,
*p < 0.05.

TABLE 5

Blood Biochemistry - scyllo-inositol Dose Study

| | Untreated n = 4 | 100 mg/Kg n = 4 | 30 mg/Kg n = 3 | 10 mg/Kg n = 5 | Reference Levels (Vita-Tech & CCAC) |
|---|---|---|---|---|---|
| Biochemistry | | | | | |
| Total protein | 46 ± 2 g/L | 49 ± 2 | 50 ± 2.6 | 50 ± 3 | 35-72 |
| Albumin | 35 ± 0 g/L | 31 ± 1 | 33 ± 2 | 33 ± 4 | 25-48 |
| Globulin | 12 ± 1 g/L | 19 ± 2 | 17 ± 1 | 17 ± 2 | 18-82 |
| Bilirubin | 2.4 ± 1 umol/L | 1.9 ± 0 | 2.0 ± 1 | 1.9 ± 0.6 | 2-15 |
| ALP | 81 ± 10 U/L | 76 ± 11 | 81 ± 10 | 73 ± 22 | 28-94 |
| ALT | 42 ± 4 U/L | 38 ± 4 | 42 ± 4 | 51 ± 20 | 28-184 |
| Glucose | 11 ± 2 mmol/L | 11 ± 2 | 12 ± 2 | 7 ± 2 | 9.7-18.6 |
| Urea | 9 ± 3 mmol/L | 7.4 ± 1 | 9 ± 3 | 10 ± 2 | 12.1-20.6 |
| Creatinine | 36 ± 5 umol/L | 31 ± 4 | 35 ± 5 | 40 ± 5 | 26-88 |
| Hemolysis | Normal | Normal | Normal | Normal | |
| Icteria | Normal | Normal | Normal | Normal | |
| Lipemia | Normal | Normal | Normal | Normal | |

Example 11—Inositol Treatment does not Affect Blood Chemistry

In order to rule out any deleterious effects of inositol treatment on blood chemistry and organ function, blood was analyzed after one month treatment with both scyllo- and allo-inositol (Table 5,6). The total protein, albumin, globulin, bilirubin, alkaline phosphatase, glucose, urea and creatinine were not significantly different between treatment groups or from untreated TgCRND8 mice. All levels fell within the normal range as determined for non-transgenic wild type mice. In addition hemolysis, icteria and lipemia were all normal. These results suggest that allo- and scyllo-inositol do not exhibit obvious deleterious effects on blood chemistry or organ function.

TABLE 6

Blood Biochemistry - 1 Month Treatment Study

| | Untreated n = 4 | Allo-Inositol n = 4 | Reference Levels (Vita-Tech & CCAC) |
|---|---|---|---|
| Biochemistry | | | |
| Total protein | 46 ± 2 g/L | 48 ± 2 | 35-72 |
| Albumin | 35 ± 0 g/L | 32 ± 2 | 25-48 |
| Globulin | 12 ± 1 g/L | 17 ± 3 | 18-82 |
| Bilirubin | 2.4 ± 1 umol/L | 2.9 ± 3 | 2-15 |
| ALP | 81 ± 10 U/L | 95 ± 16 | 28-94 |
| ALT | 42 ± 4 U/L | 44 ± 4 | 28-184 |
| Glucose | 11 ± 2 mmol/L | 10 ± 3 | 9.7-18.6 |
| Urea | 9 ± 3 mmol/L | 18.6 ± 13 | 12.1-20.6 |
| Creatinine | 36 ± 5 umol/L | 69 ± 64 | 26-88 |
| Hemolysis | Normal | Normal | |
| Icteria | Normal | Normal | |
| Lipemia | Normal | Normal | |

Example 12—Efficacy of Scyllo-Inositol in Preventing AD-Like Patholog in a Double Transeenic Mouse Model of Alzheimer's Disease, PS1×APP Tg PS1×APP mice are an enhanced model of Alzheimer's disease which express a mutant human PS1 transgene encoding two familial mutations (M46L and L286V) in conjunction with the human APP transgene encoding the Indiana and Swedish familial mutations. These animals develop robust expression of cerebral Aβ levels and amyloid deposition by 30-45 days of age. In a prophylactic trial, TgPS1×APP mice were treated with scyllo-inositol from weaning and were assessed for effects on neuropathology at 2 months of age (FIGS. 16 and 17). Compared with untreated TgPS1×APP mice, scyllo-inositol treated TgPS1× APP mice displayed a significant decrease in all measures of plaque burden at 2 months of age (% brain area covered in plaques=0.157±0.007 vs. 0.065±0.016, p<0.001; mean plaque size=177±8 $\mu m^2$ vs. 149±5 $\mu m^2$, p<0.05; plaque count 3054±324 vs. 1514±510, p<0.01; (FIG. 17). These results demonstrate that scyllo-inositol prevents amyloid deposition in two robust models of Alzheimer's disease.

Example 13—Effect of Increased Caloric Intake on TgCRND8 Mice

In order to rule out the contribution of increased caloric intake or non-specific effects, TgCRND8 mice were treated with a simple sugar of similar molecular weight, mannitol. At 6 months of age, mannitol treated TgCRND8 mice were indistinguishable from untreated TgCRND8 mice (FIG. 11A) and were significantly different from mannitol treated non-Tg littermates (FIG. 11B). Mannitol had no effect on the behaviour of non-Tg mice, since mannitol treated non-Tg mice were indistinguishable from untreated non-Tg mice. These results correlate with the pathological studies that indicate mannitol did not alter the plaque load in TgCRND8 mice (FIG. 11C). Simultaneous monitoring of survival demonstrated that mannitol had no effect on the survival of TgCRND8 mice (FIG. 11D).

Although the present invention has been described in relation to particular embodiments thereof, many other variations and modifications and other uses will become apparent to those skilled in the art. The present invention therefore is not limited by the specific disclosure herein, but only by the appended claims.

What is claimed is:

1. A method of treating Alzheimer's symptoms in a subject having Down's syndrome comprising administering to said subject about 1 to about 70 mg/kg/day of scyllo-inositol.

2. The method of claim 1 wherein said amount is about 1 to about 10 mg/kg/day.

3. The method of claim 2 wherein the administration is orally.

4. The method of claim 3 wherein the administration is once or twice a day.

5. The method of claim 2 comprising administering scyllo-inositol in a pharmaceutical composition.

6. The method of claim 2 wherein scyllo-inositol is administered in an oral pill, liquid or suspension.

7. The method of claim 2 further comprising administering a second agent which is an anti-depressant.

* * * * *